US011840730B1

(12) United States Patent
Porreca et al.

(10) Patent No.: US 11,840,730 B1
(45) Date of Patent: Dec. 12, 2023

(54) METHODS AND COMPOSITIONS FOR EVALUATING GENETIC MARKERS

(71) Applicant: Molecular Loop Biosciences, Inc., Cambridge, MA (US)

(72) Inventors: Gregory Porreca, Cambridge, MA (US); Uri Laserson, Boston, MA (US)

(73) Assignee: MOLECULAR LOOP BIOSCIENCES, INC., Cambridge, MA (US)

( * ) Notice: Subject to any disclaimer, the term of this patent is extended or adjusted under 35 U.S.C. 154(b) by 516 days.

(21) Appl. No.: 16/952,764

(22) Filed: Nov. 19, 2020

Related U.S. Application Data

(63) Continuation of application No. 15/231,687, filed on Aug. 8, 2016, now abandoned, which is a continuation of application No. 13/266,862, filed as application No. PCT/US2010/001293 on Apr. 30, 2010.

(60) Provisional application No. 61/182,089, filed on May 28, 2009, provisional application No. 61/179,358, filed on May 18, 2009, provisional application No. 61/178,923, filed on May 15, 2009, provisional application No. 61/174,470, filed on Apr. 30, 2009.

(51) Int. Cl.
  *C12Q 1/6874* (2018.01)
  *C12Q 1/6827* (2018.01)
  *C12Q 1/6883* (2018.01)

(52) U.S. Cl.
  CPC ......... *C12Q 1/6874* (2013.01); *C12Q 1/6827* (2013.01); *C12Q 1/6883* (2013.01)

(58) Field of Classification Search
  CPC ... C12Q 1/6874; C12Q 1/6827; C12Q 1/6883
  See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,348,853 A | 9/1994 | Wang et al. |
| 5,434,049 A | 7/1995 | Okano et al. |
| 5,459,307 A | 10/1995 | Klotz, Jr. |
| 5,486,686 A | 1/1996 | Zdybel, Jr. et al. |
| 5,491,224 A | 2/1996 | Bittner et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,971,921 A | 10/1999 | Timbel |
| 5,993,611 A | 11/1999 | Moroney et al. |
| 5,994,056 A | 11/1999 | Higuchi |
| 6,020,127 A | 2/2000 | MacKenzie et al. |
| 6,033,854 A | 3/2000 | Kurnit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |
| 6,197,508 B1 | 3/2001 | Stanley |
| 6,197,574 B1 | 3/2001 | Miyamoto et al. |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |

(Continued)

FOREIGN PATENT DOCUMENTS

| | | |
|---|---|---|
| EP | 1 321 477 A1 | 6/2003 |
| EP | 1 564 306 A2 | 8/2005 |

(Continued)

OTHER PUBLICATIONS

Porecca(Nature methods (2007) vol. 4, pp. 931-936).*

(Continued)

*Primary Examiner* — Steven Pohnert
(74) *Attorney, Agent, or Firm* — Withers Bergman LLP; Thomas C. Meyers

(57) ABSTRACT

Aspects of the invention relates to methods and compositions that are useful to reduce bias and increase the reproducibility of multiplex analysis of genetic loci. In some configurations, predetermined preparative steps and/or nucleic acid sequence analysis techniques are used in multiplex analyses for a plurality of genetic loci in a plurality of samples.

9 Claims, 16 Drawing Sheets

Specification includes a Sequence Listing.

(56) References Cited

U.S. PATENT DOCUMENTS

| | | |
|---|---|---|
| 6,714,874 B1 | 3/2004 | Myers et al. |
| 6,716,580 B2 | 4/2004 | Gold et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,738,300 B2 | 5/2014 | Porreca et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,066,259 B2 | 9/2018 | Gore et al. |
| 10,202,637 B2 | 2/2019 | Umbarger |
| 10,227,635 B2 | 3/2019 | Umbarger et al. |
| 10,604,799 B2 | 3/2020 | Porreca et al. |
| 10,683,533 B2 | 6/2020 | Umbarger et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0042052 A1 | 4/2002 | Nilsen et al. |
| 2002/0091666 A1 | 7/2002 | Rice et al. |
| 2002/0164629 A1 | 11/2002 | Quake et al. |
| 2002/0172954 A1 | 11/2002 | Mao et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0053275 A1 | 3/2004 | Shafer |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0161773 A1 | 8/2004 | Rogan et al. |
| 2004/0170965 A1 | 9/2004 | Scholl et al. |
| 2004/0171051 A1 | 9/2004 | Holloway |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0250147 A1 | 11/2005 | Macevicz |
| 2005/0272065 A1 | 12/2005 | Lakey et al. |
| 2006/0008824 A1 | 1/2006 | Ronaghi et al. |
| 2006/0019304 A1 | 1/2006 | Hardenbol et al. |
| 2006/0024681 A1 | 2/2006 | Smith et al. |
| 2006/0030536 A1 | 2/2006 | Yu et al. |
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0246500 A1 | 11/2006 | Browne |
| 2006/0263789 A1 | 11/2006 | Kincaid |
| 2006/0281098 A1 | 12/2006 | Miao et al. |
| 2006/0286577 A1 | 12/2006 | Jia |
| 2006/0292585 A1 | 12/2006 | Nautiyal et al. |
| 2006/0292611 A1 | 12/2006 | Berka et al. |
| 2007/0009925 A1 | 1/2007 | Fang et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0212704 A1 | 9/2007 | Dong et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |

(56) References Cited

U.S. PATENT DOCUMENTS

| | | |
|---|---|---|
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0125324 A1 | 5/2008 | Petersdorf et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0035777 A1 | 2/2009 | Kokoris et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0220955 A1 | 9/2009 | Verrant |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0076185 A1 | 3/2010 | Adey et al. |
| 2010/0086914 A1 | 4/2010 | Bentley et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kum et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0129755 A1 | 5/2013 | Song |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268206 A1 | 10/2013 | Porreca et al. |
| 2013/0268474 A1 | 10/2013 | Nizzari et al. |
| 2013/0274146 A1 | 10/2013 | Umbarger et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0337447 A1 | 12/2013 | Porreca et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0255931 A1 | 9/2014 | Porreca et al. |
| 2014/0308667 A1 | 10/2014 | Umbarger |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0111208 A1 | 4/2015 | Umbarger et al. |
| 2015/0178445 A1 | 6/2015 | Cibulskis et al. |
| 2015/0258170 A1 | 9/2015 | McCabe et al. |
| 2015/0299767 A1 | 10/2015 | Armour et al. |
| 2015/0310163 A1 | 10/2015 | Kingsmore et al. |
| 2015/0354003 A1 | 12/2015 | Umbarger |
| 2016/0003812 A1 | 1/2016 | Porreca et al. |
| 2016/0034638 A1 | 2/2016 | Spence et al. |
| 2016/0068889 A1 | 3/2016 | Gole et al. |
| 2016/0210486 A1 | 7/2016 | Porreca et al. |
| 2016/0251719 A1 | 9/2016 | Umbarger |
| 2017/0044610 A1 | 2/2017 | Johnson |
| 2017/0129964 A1 | 5/2017 | Cheung |
| 2017/0183731 A1 | 6/2017 | Mann et al. |
| 2017/0275676 A1 | 9/2017 | Umbarger |
| 2018/0371533 A1 | 12/2018 | Gore et al. |
| 2019/0233881 A1 | 8/2019 | Umbarger et al. |
| 2020/0181696 A1 | 6/2020 | Porreca et al. |

FOREIGN PATENT DOCUMENTS

| | | |
|---|---|---|
| EP | 10770071.8 | 11/2010 |
| EP | 2425240 A2 | 3/2012 |
| EP | 2 437 191 A2 | 4/2012 |
| EP | 2716766 A1 | 4/2014 |
| WO | 95/011995 A1 | 5/1995 |
| WO | 1996/019586 A1 | 6/1996 |
| WO | 98/014275 A1 | 4/1998 |
| WO | 98/044151 A1 | 10/1998 |
| WO | 00/018957 A1 | 4/2000 |

(56) References Cited

FOREIGN PATENT DOCUMENTS

| | | |
|---|---|---|
| WO | 02/093453 A2 | 11/2002 |
| WO | 2004/018497 A2 | 3/2004 |
| WO | 2004/083819 A2 | 9/2004 |
| WO | 2005/003304 A2 | 1/2005 |
| WO | 2006/084132 A2 | 8/2006 |
| WO | 2007/010251 A2 | 1/2007 |
| WO | 2007/061284 A1 | 5/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2009/036525 A2 | 3/2009 |
| WO | 2009/076238 A2 | 6/2009 |
| WO | 2010/024894 A1 | 3/2010 |
| WO | 2010/115154 A1 | 10/2010 |
| WO | 2010/126614 A2 | 11/2010 |
| WO | 2011/006020 A1 | 1/2011 |
| WO | 2011066476 A1 | 6/2011 |
| WO | 2011067378 A1 | 6/2011 |
| WO | 2011/102998 A2 | 8/2011 |
| WO | 2011/155833 A2 | 12/2011 |
| WO | 2012/006291 A2 | 1/2012 |
| WO | 2012040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2012/149171 A1 | 11/2012 |
| WO | 2012/170725 A2 | 12/2012 |
| WO | 2013/058907 A1 | 4/2013 |
| WO | 2013/148496 A1 | 10/2013 |
| WO | 2013/177086 A1 | 11/2013 |
| WO | 2013/191775 A2 | 12/2013 |
| WO | 2014/052909 A2 | 4/2014 |
| WO | 2014/074246 A1 | 5/2014 |
| WO | 2015/119941 A2 | 8/2015 |

OTHER PUBLICATIONS

Wang (Genome Biology (2007) vol. 8, R246.1-246.14).*
Schiffman (Journal of Clinical Oncology (2007) vol. 25, p. 530).*
Tan, 2014, Clinical outcome of preimplantation genetic diagnosis and screening using next generation sequencing, GigaScience 3(30):1-9.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217.
Thorstenson, 1998, An Automated Hydrodynamic Process for Controlled, Unbiased DNA Shearing, Genome Res 8(8): 848-855.
Thorvaldsdottir, 2012, Integrative Genomics Viewer (IGV): high-performance genomics data visualization and exploration, Brief Bioinform 24(2):178-92.
Tkachuk, 1990, Detection of bcr-abl Fusion in Chronic Myelogeneous Leukemia by in Situ Hybridization, Science 250:559.
Tobler, 2005, The SNPlex Genotyping System: A Flexible and Scalable Platform for SNP Genotyping, J Biomol Tech 16(4):398.
Tokino, 1996, Characterization of the human p57 KIP2 gene: alternative splicing, insertion/deletion polymorphisms in VNTR sequences in the coding region, and mutational analysis, Human Genetics 96:625-31.
Treangen, 2011, Repetitive DNA and next-generation sequencing: computational challenges and solutions, Nat Rev Gen 13(1):36-46.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013.
Umbarger, 2014, Next-generation carrier screening, Gen Med 16(2):132-140.
Veeneman, 2012, Oculus: faster sequence alignment by streaming read compression, BMC Bioinformatics 13:297.
Wahl, 1979, Efficient transfer of large DNA fragments from agarose gels to diazobenzyloxymethyl-paper and rapid hybridization by using dextran sulfate, PNAS 76:3683-3687.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Wang, 2005, Allele quantification using molecular inversion probes (MIP), Nucleic Acids Res 33(21):e183.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988.
Watson, 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Wirth, 1999, Quantitative analysis of survival motor neuron copies, Am J Hum Genet 64:1340-1356.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18 (5):821-829.
Zhang, 2011, Is Mitochondrial tRNAphe Variant m.593T.Ca Synergistically Pathogenic Mutation in Chinese LHON Families with m.11778G.A? PLoS ONE 6(10) e26511.
Zhao, 2009, PGA4genomics for comparative genome assembly based on genetic algorithm optimization, Genomics 94 (4):284-6.

(56) References Cited

OTHER PUBLICATIONS

Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30 (8):1073-1080.
Zhulidov, 2004, Simple cDNA normalization using kamchatka crab duplex-specific nuclease, Nucl Acids Res 32(3):e37.
Zimmerman, 2010, A novel custom resequencing array for dilated cardiomyopathy, Gen Med 12(5):268-78.
Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic bligodeoxyribonucleotides, Nucl Acid Res 15(13):5305-5321.
Craig, 1997, Removal of repetitive sequences from FISH probes, Hum Genet 100:472.
Cremers, 1998, Autosomal Recessive Retinitis Pigmentosa and Cone-Rod Dystrophy Caused by Splice Site Mutations In the Stargardt's Disease Gene ABCR, Hum Mol Gen 7(3):355.
Cronin, 1996, Cystic Fibrosis Mutation Detection by Hybridization to Light-Generated DNA Probe Arrays Human Mutation 7:244.
Dahl, 2005, Multiplex amplification enabled by selective circularization of large sets of genomic DNA fragments, Nucleic Acids Res 33(8):e71.
Danecek, 2011, The variant call format and VCFtools, Bioinformatics 27(15):2156-2158.
De la Bastide, 2007, Assembling genome DNA sequences with PHRAP, Current Protocols in Bioinformatics 17:11.4.1-11.4.15.
Delcher, 1999, Alignment of whole genomes, Nuc Acids Res 27(11):2369-2376.
Den Dunnen, 2003, Mutation Nomenclature, Curr Prot Hum Genet 7.13.1-7.13.8.
Deng et al., 2012, Supplementary Material, Nature Biotechnology, S1-1-S1-1 1, Retrieved from the Internet on Oct. 24, 2012.
Deng, 2009, targeted bisulfite sequencing reveals changes in DNA methylation, Nat Biotech 27(4):353-360.
Deorowicz, 2013, Data compression for sequencing data, Alg for Mole Bio 8:25.
Diep, 2012, Library-free methylation sequencing with bisulfite padlock probes, Nature Methods 9:270-272 (and supplemental information).
DiGuistini, 2009, De novo sequence assembly of a filamentous fungus using Sanger, 454 and Illumina sequence data, Genome Biology, 10:R94.
Dolinsek, 2013, Depletion of unwanted nucleic acid templates by selection cleavage: LNAzymes, catalytically active bligonucleotides containing locked nucleic acids, open a new window for detecting rare microbial community members, App Env Microbiol 79(5):1534-1544.
Dong, 2011, Mutation surveyor: An in silico tool for sequencing analysis, Methods Mol Biol 760:223-37.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12): e1000589.
Ericsson, 2008, A dual-tag microarray platform for high-performance nucleic acid and protein analyses, Nucl Acids Res 36:e45.
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014.
Fitch, 1970, Distinguishing homologs from analogous proteins, Syst Biol 19(2):99-113.

Flaschker, 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f'-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke, 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan (106 pages).
Goto, 2010, BioRuby: bioinformatics software for the Ruby programming language, Bioinformatics 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154.
Gustincich, 1991, A fast method for high-quality genomic DNA extraction from whole human blood, BioTechniques 11 (3):298-302.
Gut, 1995, A procedure for selective DNA alkylation and detection by mass spectrometry, Nucl Acids Res 23 (8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harris, 2006, Defects can increase the melting temperature of DNA-nanoparticle assemblies, J Phys Chem B 110 (33):16393-6.
Harris, 2008, Helicos True Single Molecule Sequencing (tSMS) Science 320:106-109.
Harris, 2008, Single-molecule DNA sequencing of a viral genome, Science 320(5872):106-9.
Heger, 2006, Protonation of Cresol Red in Acidic Aqueous Solutions Caused by Freezing, J Phys Chem B 110 (3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Abravaya, 1995, Detection of point mutations with a modified ligase chain reaction (GAP-LCR), Nucleic Acids Research, 23(4): 675-682.

(56) References Cited

OTHER PUBLICATIONS

Adey, 2010, Rapid, low-input, low-bias construction of shotgun fragment libraries by high-density in vitro transposition, Genome Biol 11:R119.
Ageno, 1969, The alkaline denaturation of DNA, Biophys J 9(11):1281-1311.
Agrawal, 1990, Site-specific functionalization of oligodeoxynucleotides for non-radioactive labelling, Tetrahedron Let 31:1543-1546.
Akhras, 2007, Connector inversion probe technology: A powerful one-primer multiplex DNA amplification system for numerous scientific applications, PLoSOne 9:e915.
Akhras, 2007, PathogenMip Assay: a multiplex pathogen detection assay, PLOS One 2:e2230.
Alazard, 2002, Sequencing of production-scale synthetic oligonucleotides by enriching for coupling failures using matrix-assisted laser desorption/ionization time of-flight mass spectrometry, Anal Biochem 301:57-64.
Alazard, 2006, Sequencing oligonucleotides by enrichment of coupling failures using matrix-assisted laser desorption/ionization time-of-flight mass spectrometry, Curr Protoc Nucleic Acid Chem, Chapter 10, Unit 10:1-7.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401.
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3 (65ra4).
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted aser desorption ionization analysis, Anal Biochem 258:31-37.
Bhangale, 2006, Automating resequencing-based detection of insertion-deletion polymorphisms, Nature Genetics 38:1457-1462.
Bickle, 1993, Biology of DNA Restriction, Microbiol Rev 57(2):434-50.
Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brinkman, 2004, Splice Variants as Cancer Biomarkers, Clin Biochem 37:584.
Brison, 1982, General method for cloning amplified DNA by differential screening, Mol Cell Biol 2(5):578-587.
Brown, 1979, Chemical synthesis and cloning of a tyrosine tRNA gene, Methods Enzymol 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA. (24 pages).
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.
Chan, 2011, Natural and engineered nicking endonucleases-from cleavage mechanism to engineering of strand- specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013.
Chevreux, 1999, Genome sequence assembly using trace signals and additional sequence information, Proc GCB 99:45-56.
Chirgwin, 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Ciotti, 2004, Triplet repeat prmied PCR (TP PCR) in molecular diagnostic testing for Friedrich ataxia, J Mol Diag 6 (4):285-9.
Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment strategies for next-generation sequencing, Nat Meth 7(2):111-118.
Margulies, 2005, Genome sequencing in micro-fabricated high-density picotiter reactors, Nature, 437:376-380.
Marras, 1999, Multiplex detection of single-nucleotide variations using molecular beacons, Genetic Analysis: Biomolecular Engineering 14:151.
Maxam, 1977, A new method for sequencing DNA, PNAS, 74:560-564.
May 1988, How Many Species Are There on Earth?, Science 241(4872):1441-9.
McDonnell, 2007, Antisepsis, disinfection, and sterilization: types, action, and resistance, p. 239.
McKenna, 2010, The Genome Analysis Toolkit: A MapReduce framework for analyzing next-generation DNA sequencing data, Genome Research 20:1297-1303.

(56) References Cited

OTHER PUBLICATIONS

Messiaen, 1999, Exon 10b of the NF1 gene represents a mutational hotspot and harbors a recurrent missense mutation Y489C associated with aberrant splicing, Genetics in Medicine, 1(6):248-253.
Meyer, 2007, Targeted high-throughput sequencing of tagged nucleic acid samples, Nucleic Acids Research 35(15): e97 (5 pages).
Meyer, 2008, Parallel tagged sequencing on the 454 platform, Nat Protocol 3(2):267-278.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32 (17):e135.
Minton, 2011, Mutation Surveyor: software for DNA sequence analysis, Meth Mol Biol 688:143-53.
Miyake, 2009, PIK3CA gene mutations and umplification in uterine cancers, Canc Lett 261:120-126.
Miyazaki, 2009, Characterization of deletion breakpoints in patients with dystrophinopathy carrying a deletion of exons 15-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, Deliminate—a fast and efficient methods for loss-less compression of genomice sequences, Bioinformatics 28(19):2527-2529.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment—the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen, 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Okou, 2007, Microarray-based genomic selection for high-throughput reseugencing, Nat Meth 4(11):907-909.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bio-informatics 16(6):548-57.
Pearson, 1988, Improved tools for biological sequence comparison, PNAS 85(8):2444-8.
Holland, 2008, BioJava: an open-source framework for bioinformatics, Bioinformatics 24(18):2096-2097.
Homer, 2008, Resolving Individuals Contributing Trace Amounts of DNA to Highly Complex Mixtures Using High-Density SNP Genotyping Microarrays. PLoS One 4(8):e1000167.
Homer, 2009, BFAST: An alignment tool for large scale genome resequencing, PLoS ONE 4(11):e7767.
Housley, 2009, SNP discovery and haplotype analysis in the segmentally duplicated DRD5 coding region, Ann Hum Genet 73(3):274-282.
Huang, 2008, Comparative analysis of common CFTR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, pp. 145-156, Salzberg & Warnow, Eds. Springer-Verlag, Berlin, Heidelberg.
Illumina, 2010, De Novo assembly using Illumina reads, Technical Note (8 pages).
International Human Genome Sequencing Consortium, 2004, Finishing the euchromatic sequence of the human genome, Nature 431:931-945.
Iqbal, 2012, De novo assembly and genotyping of variants using colored de Bruijn graphs, Nature Genetics 44:226-232.
Isosomppi, 2009, Disease-causing mutations in the CLRN1 gene alter normal CLRN1 protien trafficking to the plasma membrane, Mol Vis 15:1806-1818.
Jaijo, 2010, Microarray-based mutation analysis of 183 Spanish families with Usher syndrome, Invest Ophthalmol Vis Sci 51(3):1311-7.
Jensen, 2001, Orthologs and paralogs—we need to get it right, Genome Biol 2(8):1002-1002.3.
Jones, 2008, Core signaling pathways in human pancreatic cancers revealed by global genomic analyses, Science 321(5897):1801-1806.
Kambara, 1988, Optimization of Parameters in a DNA Sequenator Using Fluorescence Detection, Nature Biotechnology 6:816-821.
Kennedy, 2013, Accessing more human genetic variation with short sequencing reads, American Society of Human Genetics 63rd Annual Meeting, Abstract, Oct. 22, 2013.

(56) References Cited

OTHER PUBLICATIONS

Kent, 2002, BLAT—The BLAST-like alignment tool, Genome Res 12(4): 656-664.
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162.
Kircher, 2010, High-througput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLoS One 6(8):e23455.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125 (2):219-229.
Krishnakumar, 2008, A comprehensive assay for targeted multiplex amplification of human DNA sequences, PNAS 105:9296-301.
Kumar, 2010, Comparing de novo assemblers for 454 transcriptome data, Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.
Li, 2003, DNA binding and cleavage by the periplasmic nuclease Vvn: a novel structure with a known active site, EMBO J 22(15):4014-4025.
Li, 2008, SOAP: short oligonucleotide alignment program, Bioinformatics 24(5):713-14.
Li, 2009, Fast and accurate short read alignment with Burrows-Wheeler transform, Bioinformatics, 25 (14):1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, Fast and accurate long-read alignment with Burrows-Wheeler transform, Bioinformatics 26(5):589-95.
Li, 2011, Improving SNP discovery by base alignment quality, Bioinformatics 27:1157.
Li, 2011, Single nucleotide polymorphism genotyping and point mutation detection by ligation on microarrays, J Nanosci Nanotechnol 11(2):994-1003.
Li, 2012, A new approach to detecting low-level mutations in next-generation sequence data, Genome Biol 13:1-15.
Li, 2014, HUGO: Hierarchical mUlti-reference Genome compression for aligned reads, JAMIA 21:363-373.
Lin, 2008, ZOOM! Zillions of Oligos Mapped, Bioinformatics, 24:2431.
Lin, 2010, A molecular inversion prove assay for detecting alternative splicing, BMC Genomics 11(712):1-14.
Lin, 2012, Development and evaluation of a reverse dot blot assay for the simultaneous detection of common alpha and beta thalassemia in Chinese, Blood Cells Molecules, and Diseases 48(2):86-90.
Lipman, 1985, Rapid and sensitive protein similarity searches, Science 227(4693):1435-41.
Liu, 2012, Comparison of next-generation sequencing systems, J Biomed Biotech 2012:251364.
Llopis, 1998, Measurement of cytosolic, mitochondrial, and Golgi pH in single living cells with green fluorescent proteins, PNAS 95(12):6803-08.
Ma, 2006, Application of real-time polymerase chain reaction (RT-PCR), J Am Soc 1-15.
MacArthur, 2014, Guidelines for investigating causality of sequence variants in human disease, Nature 508:469-76.
Pertea, 2003, TIGR gene indices clustering tools (TGICL), Bioinformatics 19(5):651-52.
Pieles, 1993, Matrix-assisted laser desorption ionization time of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplificaiton of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013.
Pourmand, 2006, PathgoenMIPer: a tool for the design of molecular inversion probes, BMC informatics 7:500.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed. (72 pages).
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS ONE 3:e3373.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl, 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Baihan, 2009, Update on Usher syndrome, Curr Op Neurology 22(1):19-24.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1987, Isolation of differentially expressed genes, Meth Enzym 152:423-432.
Sauro, 2004, How Do You Calculate a Z-Score/ Sigma Level?, https://www.measuringusability.com/zcalc.htm (online publication).
Sauro, 2004, What's a Z-score and Why Use It in Usability Testing?, https://www.measuringusability.com/z.htm (online publication).
Schadt, 2010, A window into third-generation sequencing, Human Mol Genet 19(R2):R227-40.
Schatz, 2010, Assembly of large genomes using second-generation sequencing, Genome Res., 20:1165-1173.
Schiffman, 2009, Molecular inversion probes reveal patterns of 9p21 deletion and copy number aberrations in childhood leukemia, Cancer Genetics and Cytogenetics 193:9-18.

(56) References Cited

OTHER PUBLICATIONS

Schneeberger, 2011, Reference-guided assembly of four diverse *Arabidopsis thaliana* genomes, PNAS 108 (25):10249-10254.

Schouten, 2002, Relative Quantification of 40 Nucleic Acid Sequences by Multiplex Ligation-Dependent Probe Amplification, Nucle Acids Res 30 (12):257.

Schrijver, 2005, Diagnostic testing by CFTR gene mutation analysis in a large group of Hispanics, J Mol Diag 7 (2):289-299.

Schuette, 1995, Sequence analysis of phosphorothioate oligonucleotides via matrix-assisted laser desorption ionization time-of-flight mass spectrometry, J Pharm Biomed Anal 13:1195-1203.

Schwartz, 2009, Identification of cystic fibrosis variants by polymerase chain reaction/oligonucleotide ligation assay, J Mol Diag 11(3):211-15.

Schwartz, 2011, Clinical utility of single nucleotide polymorphism arrays, Clin Lab Med 31(4):581-94.

Sequeira, 1997, Implementing generic, object-oriented models in biology, Ecological Modeling 94.1:17-31.

Shagin, 2002, A novel method for SNP detection, Genome Res 12:1935.

Shen, 2011, High quality DNA sequence capture of 524 disease candidate genes, PNAS 108(16):6549-6554.

Shen, 2013, Multiplex capture with double-stranded DNA probes, Genome Medicine 5(50):1-8.

Sievers, 2011, Fast, scalable generation of high-quality protein multiple sequence alignments using Clustal Omega, Mol Syst Biol 7:539.

Simpson, 2009, ABySS: A parallel assembler for short read sequence data, Genome Res., 19(6):1117-23.

Slater, 2005, Automated generation of heuristics for biological sequence comparison, BMC Bioinformatics 6:31.

Smirnov, 1996, Sequencing oligonucleotides by exonuclease digestion and delayed extraction matrix-assisted laser desorption ionization time-of-flight mass spectrometry, Anal Biochem 238:19-25.

Smith, 1985, The synthesis of oligonucleotides containing an aliphatic amino group at the 5' terminus: synthesis of fluorescent DNA primers for use in DNA sequence analysis, Nucl Acid Res 13:2399-2412.

Smith, 2010, Highly-multiplexed barcode sequencing: an efficient method for parallel analysis of pooled samples, Nucleic Acids Research 38(13):e142 (8 pages).

Soni, 2007, Progress toward ultrafast DNA sequencing using solid-state nanopores, Clin Chem 53(11):1996-2001.

Spanu, 2010, Genome expansion and gene loss in powdery mildew fungi reveal tradeoffs in extreme parasitism, Science 330(6010):1543-46.

Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.

Streit, 2003, CFTR gene: molecular analysis in patients from South Brazil, Molecular Genetics and Metabolism 78:259-264.

Strom, 2005, Mutation detection, interpretation, and applications in the clinical laboratory setting, Mutat Res 673:160-67.

Summerer, 2009, Enabling technologies of genomic-scale sequence enrichment for targeted high-throughput sequencing, Genomics 94(6):363-8.

Summerer, 2010, Targeted High Throughput Sequencing of a Cancer-Related Exome Subset by Specific Sequence Capture With a Fully Automated Microarray Platform, Genomics 95(4):241-246.

Sunnucks, 1996, Microsatellite and chromosome evolution of parthenogenetic sitobion aphids in Australia, Genetics 144:747-756.

\* cited by examiner

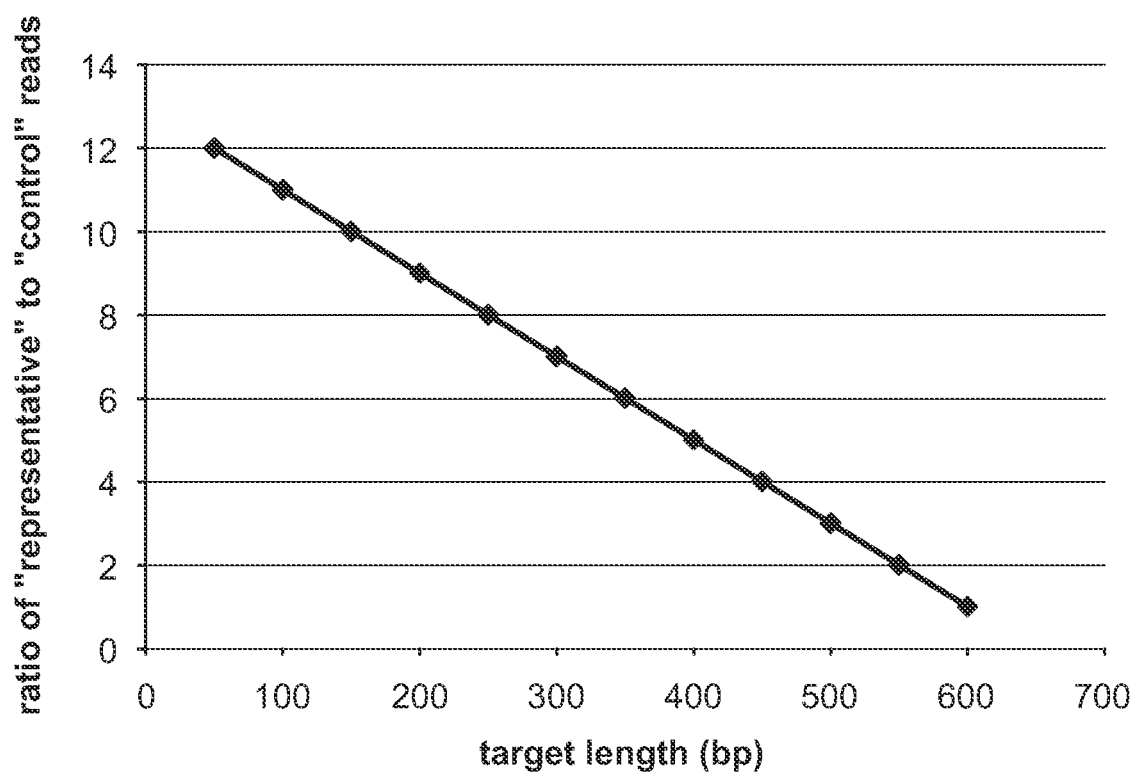

```
                        SEQUENCE LISTING

<160> NUMBER OF SEQ ID NOS: 184

<210> SEQ ID NO 1
<211> LENGTH: 52
<212> TYPE: DNA
<213> ORGANISM: Homo sapiens

<400> SEQUENCE: 1
tcacatcacc aagttaaaaa aaaaaarggg gcggggggc agaatgaaaa tt            52

<210> SEQ ID NO 2
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 2
aaacaaggat gaattaagtt ttttttttaaa aaagaaacat ttggtaaggg ga           52

<210> SEQ ID NO 3
<211> LENGTH: 52
<212> TYPE: DNA
<213> ORGANISM: Homo sapiens

<400> SEQUENCE: 3
atcaccaagt taaaaaaaaa aaagggrcgg ggggcagaa tgaaaattgc at            52

<210> SEQ ID NO 4
<211> LENGTH: 52
<212> TYPE: DNA
<213> ORGANISM: Homo sapiens

<400> SEQUENCE: 4
ctattgaacc agaaccaaac aggaatrcca tagcattttg taaactaaac tg           52
```

```
<210> SEQ ID NO 5
<211> LENGTH: 52
<212> TYPE: DNA
<213> ORGANISM: Homo sapiens

<400> SEQUENCE: 5
caggagttca agaccagcct actaaamcac acacacacac acacacacac ac            52

<210> SEQ ID NO 6
<211> LENGTH: 52
<212> TYPE: DNA
<213> ORGANISM: Homo sapiens

<400> SEQUENCE: 6
gattaaataa tagtgtttat gtacccsgct tataggagaa gagggtgtgt gt            52

<210> SEQ ID NO 7
<211> LENGTH: 52
<212> TYPE: DNA
<213> ORGANISM: Homo sapiens

<400> SEQUENCE: 7
attgttatct tttcatataa ggtaacwgag gcccagagag attaaataac at            52

<210> SEQ ID NO 8
<211> LENGTH: 52
<212> TYPE: DNA
<213> ORGANISM: Homo sapiens

<400> SEQUENCE: 8
taattttaat taagtaaatt taattgrtag ataaataagt agataaaaaa ta            52

<210> SEQ ID NO 9
<211> LENGTH: 52
<212> TYPE: DNA
<213> ORGANISM: Homo sapiens

<400> SEQUENCE: 9
gtataaaaaa aaaaaaaaaa aaagttwgaa tgttttcttg cattcagagc ct            52

<210> SEQ ID NO 10
<211> LENGTH: 52
<212> TYPE: DNA
<213> ORGANISM: Homo sapiens

<400> SEQUENCE: 10
atactaaaaa tttaaagttc tcttgcrata tattttctta atatcttaca tc            52

<210> SEQ ID NO 11
<211> LENGTH: 52
<212> TYPE: DNA
<213> ORGANISM: Homo sapiens

<400> SEQUENCE: 11
tgctgggatt acaggcgtga gccaccrcgc ctggcctgat gggacatatt tt            52

<210> SEQ ID NO 12
<211> LENGTH: 52
<212> TYPE: DNA
<213> ORGANISM: Homo sapiens

<400> SEQUENCE: 12
ctacaatata agtatagtat tgcaaamcca tcaggaaggg tgttaactat tt            52
```

<210> SEQ ID NO 13
<211> LENGTH: 54
<212> TYPE: DNA
<213> ORGANISM: Homo sapiens
<220> FEATURE:
<221> NAME/KEY: misc_feature
<222> LOCATION: (27)..(29)
<223> OTHER INFORMATION: This region may or may not be present in its
      entirety

<400> SEQUENCE: 13
gttgtctcca aacttttttt caggtgagaa ggtggccaac cgagcttcgg aaag         54

<210> SEQ ID NO 14
<211> LENGTH: 52
<212> TYPE: DNA
<213> ORGANISM: Homo sapiens

<400> SEQUENCE: 14 tttttcata aaagattata taaggmtat tgcttttgaa tcacaaacac ta             52

<210> SEQ ID NO 15
<211> LENGTH: 52
<212> TYPE: DNA
<213> ORGANISM: Homo sapiens

<400> SEQUENCE: 15
atctagtgag cagtcaggaa agagaayttc cagatcctgg aaatcagggt ta           52

<210> SEQ ID NO 16
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 16
tagagtataa aaaaaaaaaa aaaaaagtt tgaatgtttt cttgcattca ga            52

<210> SEQ ID NO 17
<211> LENGTH: 52
<212> TYPE: DNA
<213> ORGANISM: Homo sapiens

<400> SEQUENCE: 17
tgcaaatgcc aactatcaaa gatattsgag tatactgtca ataaacttca ta           52

<210> SEQ ID NO 18
<211> LENGTH: 52
<212> TYPE: DNA
<213> ORGANISM: Homo sapiens

<400> SEQUENCE: 18
tcctcaacag ttagaaacaa tattttsagt gatttcccat gccaacttta ct           52

<210> SEQ ID NO 19
<211> LENGTH: 52
<212> TYPE: DNA
<213> ORGANISM: Homo sapiens

<400> SEQUENCE: 19
tttttggtat tgttgttaaa taagtgrgaa ttcaatacag tataatgtct gt           52

<210> SEQ ID NO 20
<211> LENGTH: 87
<212> TYPE: DNA
<213> ORGANISM: Homo sapiens
<220> FEATURE:
<221> NAME/KEY: misc_feature
<222> LOCATION: (27)..(72)
<223> OTHER INFORMATION: This region may or may not be present in its
      entirety

<400> SEQUENCE: 20
cttgaaatcg gatatatata tatatatgta tatatatata tatatatata tatatatata    60
tagtattatc cctgttttca cagtttt                                       87

<210> SEQ ID NO 21
<211> LENGTH: 52
<212> TYPE: DNA
<213> ORGANISM: Homo sapiens

<400> SEQUENCE: 21 agagggctg tgaaggacac caaggargag actaagagcc aggagggaaa ac            52

<210> SEQ ID NO 22
<211> LENGTH: 52
<212> TYPE: DNA
<213> ORGANISM: Homo sapiens

<400> SEQUENCE: 22
tagagtttat tagcttttac tactctrctt agttactttg tgttacagaa ta           52

<210> SEQ ID NO 23
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 23
actagtgatg atgagcttct tttcatatgt ttgttggctg cataaatgtc ttc          53

<210> SEQ ID NO 24
<211> LENGTH: 52
<212> TYPE: DNA
<213> ORGANISM: Homo sapiens

<400> SEQUENCE: 24
gcagagaaaa gaggggctgt gaaggasacc aaggaggaga ctaagagcca gg           52

<210> SEQ ID NO 25
<211> LENGTH: 52
<212> TYPE: DNA
<213> ORGANISM: Homo sapiens

<400> SEQUENCE: 25
ttcagaggtc taccactggt gcatackcta atcacagtgt cgaaaatttt ac           52

<210> SEQ ID NO 26
<211> LENGTH: 52
<212> TYPE: DNA
<213> ORGANISM: Homo sapiens

<400> SEQUENCE: 26
aagaaagagc aaaagagggc aaacttytca tacatttttg atgtcgaaac ca    52

<210> SEQ ID NO 27
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 27
cctaaagttt aaaagaaaa aaaaaaagga agaaggaatt aaaaatccaa ag    52

<210> SEQ ID NO 28
<211> LENGTH: 52
<212> TYPE: DNA
<213> ORGANISM: Homo sapiens

<400> SEQUENCE: 28
gtgtgtgtgt gtatatatat atatatwtat atatttttt tttcctgagc ca    52

<210> SEQ ID NO 29
<211> LENGTH: 52
<212> TYPE: DNA
<213> ORGANISM: Homo sapiens

<400> SEQUENCE: 29
aaactgttga tgttttcatt tatttasatc attggaaaac tttagattct ag    52

<210> SEQ ID NO 30
<211> LENGTH: 52
<212> TYPE: DNA
<213> ORGANISM: Homo sapiens

<400> SEQUENCE: 30
tttatccatt cttaaccaga acagacrttt tttcagagct ggtccaggaa aa    52

<210> SEQ ID NO 31
<211> LENGTH: 52
<212> TYPE: DNA
<213> ORGANISM: Homo sapiens

<400> SEQUENCE: 31
ttgaaatcgg atatatatat atatatrtat atatatatat atatatatat at    52

<210> SEQ ID NO 32
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 32 tagttttta tttcctcata ttattttcag tggctttttc ttccacatct tt    52

<210> SEQ ID NO 33
<211> LENGTH: 52
<212> TYPE: DNA
<213> ORGANISM: Homo sapiens

<400> SEQUENCE: 33
acatagttct cagtggtaca actacargtg atttctcttt tcttatttct gg                52

<210> SEQ ID NO 34
<211> LENGTH: 52
<212> TYPE: DNA
<213> ORGANISM: Homo sapiens

<400> SEQUENCE: 34
agagcaatgg catcccttgt cttgtgytat acaggatgca gcaatttata gg                52

<210> SEQ ID NO 35
<211> LENGTH: 52
<212> TYPE: DNA
<213> ORGANISM: Homo sapiens

<400> SEQUENCE: 35
ttctgtctac ataagatgtc atactaratt atcttttcca gcatgcattc ag                52

<210> SEQ ID NO 36
<211> LENGTH: 52
<212> TYPE: DNA
<213> ORGANISM: Homo sapiens

<400> SEQUENCE: 36
cagggtggca tgttaggcag tgcttaraat aaatgagttg gttatacaag ta                52

<210> SEQ ID NO 37
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 37
aggacacaca cacacacaca cacacacatg cacacacatt taaatagatg cat               53

<210> SEQ ID NO 38
<211> LENGTH: 52
<212> TYPE: DNA
<213> ORGANISM: Homo sapiens

<400> SEQUENCE: 38
taaaaaattg gtataatgaa attgcayttg tagtctttgg acatttaaat cc                52

<210> SEQ ID NO 39
<211> LENGTH: 52
<212> TYPE: DNA
<213> ORGANISM: Homo sapiens

<400> SEQUENCE: 39
tttcaatact taagaggtac gcagagraaa gagggctgt gaaggacacc aa                 52

<210> SEQ ID NO 40
<211> LENGTH: 52
<212> TYPE: DNA
<213> ORGANISM: Homo sapiens

<400> SEQUENCE: 40
cagcaatgaa tattttgagg ctgaggygct gaggggtaaa attgcagcct gg                52

<210> SEQ ID NO 41

```
<211> LENGTH: 55
<212> TYPE: DNA
<213> ORGANISM: Homo sapiens
<220> FEATURE:
<221> NAME/KEY: misc_feature
<222> LOCATION: (27)..(30)
<223> OTHER INFORMATION: This region may or may not be present in its
      entirety

<400> SEQUENCE: 41
ttatggttta tattttgtg tcttctcttt aacacatctt ttctagcaga attca         55

<210> SEQ ID NO 42
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 42 gtatttagt ttttttttt tgtttgtttt gttttgtttt gttttgtttt tg             52

<210> SEQ ID NO 43
<211> LENGTH: 52
<212> TYPE: DNA
<213> ORGANISM: Homo sapiens

<400> SEQUENCE: 43
tgggtgactc catttttact tttagtytgg tctgttgagg cctcgtgaga ga           52

<210> SEQ ID NO 44
<211> LENGTH: 55
<212> TYPE: DNA
<213> ORGANISM: Homo sapiens
<220> FEATURE:
<221> NAME/KEY: misc_feature
<222> LOCATION: (27)..(30)
<223> OTHER INFORMATION: This region may or may not be present in its
      entirety

<400> SEQUENCE: 44
tattttcatg tattttagtt ttttttttt gtttgttttg ttttgttttg ttttg         55

<210> SEQ ID NO 45
<211> LENGTH: 52
<212> TYPE: DNA
<213> ORGANISM: Homo sapiens

<400> SEQUENCE: 45
gtgtgtgtgt atatatatat atatatwtat attttttttt tcctgagcca aa           52

<210> SEQ ID NO 46
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 46
aacctattag catgtctggc agaaaaatag atacttaata aatttcttaa at           52

<210> SEQ ID NO 47
<211> LENGTH: 52
```

<212> TYPE: DNA
<213> ORGANISM: Homo sapiens

<400> SEQUENCE: 47
gaggcttaga cagtttaagt aactcargca tggttacaca actagctagg gc      52

<210> SEQ ID NO 48
<211> LENGTH: 52
<212> TYPE: DNA
<213> ORGANISM: Homo sapiens

<400> SEQUENCE: 48
gtgtgagtat tatgagacca tatgttrgga gattttattt ggtattgagg at      52

<210> SEQ ID NO 49
<211> LENGTH: 52
<212> TYPE: DNA
<213> ORGANISM: Homo sapiens

<400> SEQUENCE: 49
gaaaccccac cccttctata gttttcyctt taatatttac aatggaacca tt      52

<210> SEQ ID NO 50
<211> LENGTH: 52
<212> TYPE: DNA
<213> ORGANISM: Homo sapiens

<400> SEQUENCE: 50
catatatata tagtgtgtgt gtgtgtrtat atatatatat atatatattt tt      52

<210> SEQ ID NO 51
<211> LENGTH: 53
<212> TYPE: DNA
<213> ORGANISM: Homo sapiens

<400> SEQUENCE: 51
cgagcgagag agagagagag agagagagga gccggcgcga gaactacgca tgc      53

<210> SEQ ID NO 52
<211> LENGTH: 52
<212> TYPE: DNA
<213> ORGANISM: Homo sapiens

<400> SEQUENCE: 52
ggcaggtaat atctagtacc ttacttwtat ttcctgagca cattctacat tt      52

<210> SEQ ID NO 53
<211> LENGTH: 52
<212> TYPE: DNA
<213> ORGANISM: Homo sapiens

<400> SEQUENCE: 53
ggccaggaat gggagtgctt aggtgcrgag gtggcactgt tcccgcagct gc      52

<210> SEQ ID NO 54
<211> LENGTH: 52
<212> TYPE: DNA
<213> ORGANISM: Homo sapiens

<400> SEQUENCE: 54
tgaaaactcc atcccctcag ggtcatyaga tgaagagaag accacagggg tt      52

<210> SEQ ID NO 55

```
<211> LENGTH: 52
<212> TYPE: DNA
<213> ORGANISM: Homo sapiens

<400> SEQUENCE: 55
tgtaggtaag ggtcacatgt gggagasgca gctgtgggta ggtcagccct gt        52

<210> SEQ ID NO 56
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 56
ccaagaaggc gccattacac tccagcctgg gcgacagggc gagactccct ca        52

<210> SEQ ID NO 57
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 57
tgccacaccc agctaatttg tgtgtggtat gtgtgtgtat gtatgtgtgt gt        52

<210> SEQ ID NO 58
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 58
gttcctccag taatttttt tttttttggt tttgagacag agtcttgccc tg        52

<210> SEQ ID NO 59
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 59
atcatgccca gataatttt tttttttgta ttttagtaga cacagggttt ca        52

<210> SEQ ID NO 60
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 60
cgagcgagag agagagagag agagagagga gccggcgcga gaactacgca tgc       53
```

<210> SEQ ID NO 61
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 61
cctgtgaggg gcacattcct tagtagctaa ggagttgggg gtgtgaagat cc            52

<210> SEQ ID NO 62
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 62
acaggctact ggctgggccc aggcaaaggg ggccttggca ggaaaagttc ct            52

<210> SEQ ID NO 63
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 63
gcgagagaga gagagagaga gagaggagag ccggcgcgag aactacgcat gcg           53

<210> SEQ ID NO 64
<211> LENGTH: 52
<212> TYPE: DNA
<213> ORGANISM: Homo sapiens

<400> SEQUENCE: 64
aagaagaaaa ataaaaagaa agtgggycag accgagagaa caggaagcct ga            52

<210> SEQ ID NO 65
<211> LENGTH: 52
<212> TYPE: DNA
<213> ORGANISM: Homo sapiens

<400> SEQUENCE: 65
aaggacaaag gcaaagagac aaaggckcaa cactgggggt ccccagagag tg            52

<210> SEQ ID NO 66
<211> LENGTH: 52
<212> TYPE: DNA
<213> ORGANISM: Homo sapiens

<400> SEQUENCE: 66
tacctagtca cttcctgcct ccatggygca aaggggatg ggtgtgcctc tt             52

<210> SEQ ID NO 67
<211> LENGTH: 52
<212> TYPE: DNA
<213> ORGANISM: Homo sapiens -continued

<400> SEQUENCE: 67
ctcttccgag gttccaccct gaacacyttc ctgctccctc gtggtgtaga gt    52

<210> SEQ ID NO 68
<211> LENGTH: 52
<212> TYPE: DNA
<213> ORGANISM: Homo sapiens

<400> SEQUENCE: 68
ttctgactgg caaccagccc cactctytgg gagccctcag gaatgaactt gc    52

<210> SEQ ID NO 69
<211> LENGTH: 52
<212> TYPE: DNA
<213> ORGANISM: Homo sapiens

<400> SEQUENCE: 69
gctcagcctc ccaggctgga gtgcagwggc gcgatctcgg ctcaccgcaa cc    52

<210> SEQ ID NO 70
<211> LENGTH: 52
<212> TYPE: DNA
<213> ORGANISM: Homo sapiens

<400> SEQUENCE: 70
catgaaccac atcaaatgag atttagyggg agtggcacac acagtcatga cc    52

<210> SEQ ID NO 71
<211> LENGTH: 52
<212> TYPE: DNA
<213> ORGANISM: Homo sapiens

<400> SEQUENCE: 71
aagcagccct ggggagtcgg ggcgggrcct ggattggaaa agagacggtc ac    52

<210> SEQ ID NO 72
<211> LENGTH: 52
<212> TYPE: DNA
<213> ORGANISM: Homo sapiens

<400> SEQUENCE: 72
ctccaagttc tgggagcaga gtgtgcrgct aggctcctgg gatcgaggga tg    52

<210> SEQ ID NO 73
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 73
gttcctccag taatttttt tttttkgtt ttgagacaga gtcttgccct gt    52

<210> SEQ ID NO 74
<211> LENGTH: 52
<212> TYPE: DNA
<213> ORGANISM: Homo sapiens

<400> SEQUENCE: 74
ctagtacctt acttccctca agttcawtca tctcacagat atttcctgag ca    52

```
<210> SEQ ID NO 75
<211> LENGTH: 52
<212> TYPE: DNA
<213> ORGANISM: Homo sapiens

<400> SEQUENCE: 75
aattagccgt gcgtggtggc gggtgcytgt aatcccacgt acttgggagg ct          52

<210> SEQ ID NO 76
<211> LENGTH: 52
<212> TYPE: DNA
<213> ORGANISM: Homo sapiens

<400> SEQUENCE: 76
ccatggccag ccggggaggg gacgggmaca cacagaccca cacagagact ca          52

<210> SEQ ID NO 77
<211> LENGTH: 52
<212> TYPE: DNA
<213> ORGANISM: Homo sapiens
<220> FEATURE:
<221> NAME/KEY: misc_feature
<222> LOCATION: (77)..(77)
<223> OTHER INFORMATION: May or may not be present

<400> SEQUENCE: 77
agcgagagag agagagagag agagagrgag ccggcgcgag aactacgcat gc          52

<210> SEQ ID NO 78
<211> LENGTH: 52
<212> TYPE: DNA
<213> ORGANISM: Homo sapiens

<400> SEQUENCE: 78
cgtagcagtt agcagatgat aggcggbgaa atcttatttc acagggcatt aa          52

<210> SEQ ID NO 79
<211> LENGTH: 52
<212> TYPE: DNA
<213> ORGANISM: Homo sapiens

<400> SEQUENCE: 79
ctggccctgg tgacagtggg gctgtgygtg gggccagagc cttctcagag gt          52

<210> SEQ ID NO 80
<211> LENGTH: 52
<212> TYPE: DNA
<213> ORGANISM: Homo sapiens

<400> SEQUENCE: 80
cagatactgg ccctggtgac agtgggrctg tgcgtggggc cagagccttc tc          52

<210> SEQ ID NO 81
<211> LENGTH: 52
<212> TYPE: DNA
<213> ORGANISM: Homo sapiens

<400> SEQUENCE: 81
gacagatact ggccctggtg acagtgkggc tgtgcgtggg gccagagcct tc          52

<210> SEQ ID NO 82
<211> LENGTH: 53
<212> TYPE: DNA
<213> ORGANISM: Homo sapiens
<220> FEATURE:
```

```
<221> NAME/KEY: misc_feature
<222> LOCATION: (27)..(28)
<223> OTHER INFORMATION: This region may or may not be present in its
      entirety

<400> SEQUENCE: 82
ggctcctctc tctctctctc tctctctcgc tcgctctctc gctctctcgc tct           53

<210> SEQ ID NO 83
<211> LENGTH: 52
<212> TYPE: DNA
<213> ORGANISM: Homo sapiens

<400> SEQUENCE: 83
gtttcagacc agcctggcca acatagygaa accccatctc tactaaaaat aa            52

<210> SEQ ID NO 84
<211> LENGTH: 52
<212> TYPE: DNA
<213> ORGANISM: Homo sapiens

<400> SEQUENCE: 84
agtgggcgat tggatggagc tgagtayggg gcccatccag gctaatcaca cc            52

<210> SEQ ID NO 85
<211> LENGTH: 52
<212> TYPE: DNA
<213> ORGANISM: Homo sapiens

<400> SEQUENCE: 85
ccgggctccg tgaatgtttg tcacatstct gaagaacgta tgaattacat aa            52

<210> SEQ ID NO 86
<211> LENGTH: 52
<212> TYPE: DNA
<213> ORGANISM: Homo sapiens

<400> SEQUENCE: 86
gaatcccaac cccgacgctc gtcgccsggc tccgtgaatg tttgtcacat gt            52

<210> SEQ ID NO 87
<211> LENGTH: 52
<212> TYPE: DNA
<213> ORGANISM: Homo sapiens

<400> SEQUENCE: 87
gcgaatccca accccgacgc tcgtcgycgg gctccgtgaa tgtttgtcac at            52

<210> SEQ ID NO 88
<211> LENGTH: 52
<212> TYPE: DNA
<213> ORGANISM: Homo sapiens

<400> SEQUENCE: 88
tgggcagaag tcagggtcca agaaakggc aaagaaaagt gtcagtggct ca             52

<210> SEQ ID NO 89
<211> LENGTH: 52
<212> TYPE: DNA
<213> ORGANISM: Homo sapiens

<400> SEQUENCE: 89
taagaaagac gttttgatt tttttcrgac ttctctggct ccactaccct gc             52
```

```
<210> SEQ ID NO 90
<211> LENGTH: 52
<212> TYPE: DNA
<213> ORGANISM: Homo sapiens

<400> SEQUENCE: 90
ctgattcctg gccaggagcg gtggctyacg cctgtaatcc cagcgctttg gg          52

<210> SEQ ID NO 91
<211> LENGTH: 52
<212> TYPE: DNA
<213> ORGANISM: Homo sapiens

<400> SEQUENCE: 91
taaaaatgct gattcctggc caggagyggt ggctcacgcc tgtaatccca gc          52

<210> SEQ ID NO 92
<211> LENGTH: 52
<212> TYPE: DNA
<213> ORGANISM: Homo sapiens

<400> SEQUENCE: 92
tttaaaaatg ctgattcctg gccaggmgcg gtggctcacg cctgtaatcc ca          52

<210> SEQ ID NO 93
<211> LENGTH: 52
<212> TYPE: DNA
<213> ORGANISM: Homo sapiens

<400> SEQUENCE: 93
caagacctgt caaagatctg agaaatwtta cccgacttac aagctaacca tt          52

<210> SEQ ID NO 94
<211> LENGTH: 52
<212> TYPE: DNA
<213> ORGANISM: Homo sapiens

<400> SEQUENCE: 94
actgtaataa gtgctgtaaa agaaatrcac aaaataatat agcagagggt at          52

<210> SEQ ID NO 95
<211> LENGTH: 52
<212> TYPE: DNA
<213> ORGANISM: Homo sapiens

<400> SEQUENCE: 95
cttgaggtca ggagttcaag accagtytgg gcaacatggg gaaaaccttg tc          52

<210> SEQ ID NO 96
<211> LENGTH: 52
<212> TYPE: DNA
<213> ORGANISM: Homo sapiens

<400> SEQUENCE: 96
aggttgcagt gagccgagat catgccrttg cactccagcc ggggcaacaa aa          52

<210> SEQ ID NO 97
<211> LENGTH: 52
<212> TYPE: DNA
<213> ORGANISM: Homo sapiens

<400> SEQUENCE: 97
acaagtgtct tgaaattatc tgtgatytgc tatagagcaa tacttttgta aa          52
```

<210> SEQ ID NO 98
<211> LENGTH: 52
<212> TYPE: DNA
<213> ORGANISM: Homo sapiens

<400> SEQUENCE: 98
gtgggtatat gcagctctat gcactayctg ctcatttatt tggtaaatct aa        52

<210> SEQ ID NO 99
<211> LENGTH: 59
<212> TYPE: DNA
<213> ORGANISM: Homo sapiens
<220> FEATURE:
<221> NAME/KEY: misc_feature
<222> LOCATION: (27)..(34)
<223> OTHER INFORMATION: This region may or may not be present in its
      entirety

<400> SEQUENCE: 99
tgtgtgtgtg tgcgtgtgtg tgtgtgtgtg tgtgatcata agagtggctg cagcaaact        59

<210> SEQ ID NO 100
<211> LENGTH: 52
<212> TYPE: DNA
<213> ORGANISM: Homo sapiens

<400> SEQUENCE: 100
agtctggagt gcaatggtgc aatctcrgct cactgcagcc tccacctccg gg        52

<210> SEQ ID NO 101
<211> LENGTH: 52
<212> TYPE: DNA
<213> ORGANISM: Homo sapiens

<400> SEQUENCE: 101
ctcctaatgg atatttccta aattttkctg aacagaattt aacttgagct gg        52

<210> SEQ ID NO 102
<211> LENGTH: 52
<212> TYPE: DNA
<213> ORGANISM: Homo sapiens

<400> SEQUENCE: 102
atttaaaaat ggatttctag aaaaacratc acatacttga atattttagc aa        52

<210> SEQ ID NO 103
<211> LENGTH: 52
<212> TYPE: DNA
<213> ORGANISM: Homo sapiens

<400> SEQUENCE: 103
ctataaatgg gtagcatgag ggattcragg aggtggctga agaagcacg ta        52

<210> SEQ ID NO 104
<211> LENGTH: 52
<212> TYPE: DNA
<213> ORGANISM: Homo sapiens

<400> SEQUENCE: 104
aagaaaccaa gcatagtaga gtgttaraaa accaaagcaa ctaaacaact gt        52

<210> SEQ ID NO 105
<211> LENGTH: 52

-continued

<212> TYPE: DNA
<213> ORGANISM: Homo sapiens

<400> SEQUENCE: 105
cggggctcag aacttgtaac agaaaawtaa aatatactcc actcaaggga at            52

<210> SEQ ID NO 106
<211> LENGTH: 57
<212> TYPE: DNA
<213> ORGANISM: Homo sapiens
<220> FEATURE:
<221> NAME/KEY: misc_feature
<222> LOCATION: (27)..(32)
<223> OTHER INFORMATION: This region may or may not be present in its
      entirety

<400> SEQUENCE: 106
tactacactt cacggatact gtacttgtac tttttttcca aattgaaggt ttttggc       57

<210> SEQ ID NO 107
<211> LENGTH: 63
<212> TYPE: DNA
<213> ORGANISM: Homo sapiens
<220> FEATURE:
<221> NAME/KEY: misc_feature
<222> LOCATION: (27)..(38)
<223> OTHER INFORMATION: This region may or may not be present in its
      entirety

<400> SEQUENCE: 107 ttgttttttgt ttttgttttt gtttttgttt ttgtttttttg agatggagtc tcgctctgtc   60
gcc                                                                  63

<210> SEQ ID NO 108
<211> LENGTH: 57
<212> TYPE: DNA
<213> ORGANISM: Homo sapiens
<220> FEATURE:
<221> NAME/KEY: misc_feature
<222> LOCATION: (27)..(32)
<223> OTHER INFORMATION: This region may or may not be present in its
      entirety

<400> SEQUENCE: 108
tttgccttac tacacttcac ggatactgta cttgtacttt ttttccaaat tgaaggt       57

<210> SEQ ID NO 109
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 109
gaggtggctg aaagaagcac gtatccctga tggcatggtt gcgggttata tg            52

<210> SEQ ID NO 110
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 110
gagaaaagca gttcctggaa cacccccacc ccttaacccc ttatctctgc tt    52

<210> SEQ ID NO 111
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 111
ttacatatgt atacatgtgc catgtttggt gtgccgcacc cattaactcg tc    52

<210> SEQ ID NO 112
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 112 cttttccag atttttttt tttttttgag acagagtttc actcttgttg cc    52

<210> SEQ ID NO 113
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 113
tttggaaatc ttaagctttt atttgggtgt cacagagaaa caggatctgt at    52

<210> SEQ ID NO 114
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 114
tactttaagt tttagggtac atgtgcacca tgtgcaggtt tgttacatat gt    52

<210> SEQ ID NO 115
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 115
attcatgacc agccacataa atgcacagta ttacttcgca agcatgccaa tg    52

<210> SEQ ID NO 116
<211> LENGTH: 52
<212> TYPE: DNA
<213> ORGANISM: Homo sapiens
<220> FEATURE:

<221> NAME/KEY: misc_feature
<222> LOCATION: (27)..(27)
<223> OTHER INFORMATION: May or may not be present

<400> SEQUENCE: 116
gtgcactaga attagctaaa gtgggggaaa aaaagatgca tttgatggtc ta					52

<210> SEQ ID NO 117
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 117
aacctccacc tcccaggttc aagagaattc tcctgcctca gcctcccaag ta					52

<210> SEQ ID NO 118
<211> LENGTH: 52
<212> TYPE: DNA
<213> ORGANISM: Homo sapiens

<400> SEQUENCE: 118
cctccctgtg atccgaagta gcagacrtac ttaacttcca tggtggattg tt					52

<210> SEQ ID NO 119
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 119
aaaacattat tatatctaga aaaaaaatgt atcttaacca ttgtgggaag tg					52

<210> SEQ ID NO 120
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 120
ttgaaggtaa aatcataggg agttgggagc tgtcctcttg cgctgaatca gt					52

<210> SEQ ID NO 121
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 121
acttgtggcc tttttggaga ggttagcaac tctgaaaact ctgtccctgg acc					53

<210> SEQ ID NO 122
<211> LENGTH: 52
<212> TYPE: DNA

```
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 122
gaaggagaaa aagagaggaa ataagttaaa ataataaaca caattaataa ag      52

<210> SEQ ID NO 123
<211> LENGTH: 52
<212> TYPE: DNA
<213> ORGANISM: Homo sapiens

<400> SEQUENCE: 123
tgtatacatg tgccatgttg gtgtgcygca cccattaact cgtcatttag ca      52

<210> SEQ ID NO 124
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 124
tcacctgtca cctcctatag aactttcccc tgaccctcct ctatagcatt aa      52

<210> SEQ ID NO 125
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 125
ataaatgatc atcattcaca gtagggtttt tgttttgttt ttttctgga aa       52

<210> SEQ ID NO 126
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 126
acagacatat ctacaaacac acttttttcac atatttgtgt aagtcattta tg     52

<210> SEQ ID NO 127
<211> LENGTH: 52
<212> TYPE: DNA
<213> ORGANISM: Homo sapiens

<400> SEQUENCE: 127
aaagacaact aaactaacgc tcaatgmaaa aagtattcgc tgctgtttac at      52

<210> SEQ ID NO 128
<211> LENGTH: 52
<212> TYPE: DNA
<213> ORGANISM: Homo sapiens

<400> SEQUENCE: 128
```

```
taccgtgtac cccgtgtttg tgaatgmggc cgcatattac gaaaagaaag aa            52
```

<210> SEQ ID NO 129
<211> LENGTH: 52
<212> TYPE: DNA
<213> ORGANISM: Homo sapiens

<400> SEQUENCE: 129

```
cagggctgga ggtaaaacca tttattrcta accccagagc agtgaagaag tg            52
```

<210> SEQ ID NO 130
<211> LENGTH: 52
<212> TYPE: DNA
<213> ORGANISM: Homo sapiens

<400> SEQUENCE: 130

```
ttcttcattg cctattgaag agagagygga atgctttggt tgccagatat gg            52
```

<210> SEQ ID NO 131
<211> LENGTH: 52
<212> TYPE: DNA
<213> ORGANISM: Homo sapiens

<400> SEQUENCE: 131

```
cacaagatct cattactcag gagctgycca agtgtctaat gtacttagtt aa            52
```

<210> SEQ ID NO 132
<211> LENGTH: 52
<212> TYPE: DNA
<213> ORGANISM: Homo sapiens

<400> SEQUENCE: 132

```
ttctgtgtaa catttcattt aagcaargga ttcggcaaat caaaaattgt ca            52
```

<210> SEQ ID NO 133
<211> LENGTH: 52
<212> TYPE: DNA
<213> ORGANISM: Homo sapiens

<400> SEQUENCE: 133

```
taaaacgtat tgaaggtatt attgackctg ttgaagcaaa gagaacaaaa ca            52
```

<210> SEQ ID NO 134
<211> LENGTH: 52
<212> TYPE: DNA
<213> ORGANISM: Homo sapiens

<400> SEQUENCE: 134

```
atctgctctt ccagttggat gacaagyctt gctgtctaac acctgctgca ga            52
```

<210> SEQ ID NO 135
<211> LENGTH: 52
<212> TYPE: DNA
<213> ORGANISM: Homo sapiens

<400> SEQUENCE: 135

```
ccatttttg ttgtattttt tttttcytga atacttttta tcgcagttgg tt             52
```

<210> SEQ ID NO 136
<211> LENGTH: 52
<212> TYPE: DNA
<213> ORGANISM: Homo sapiens

<400> SEQUENCE: 136
ccctgtctct aaagaaaaa aaaaaaraaa aaaaaaagaa aacaaaaccc aa    52

<210> SEQ ID NO 137
<211> LENGTH: 52
<212> TYPE: DNA
<213> ORGANISM: Homo sapiens

<400> SEQUENCE: 137
agtggctcca aaaggtcat ggaaccyctt gaggatgatg caaattgact ct    52

<210> SEQ ID NO 138
<211> LENGTH: 52
<212> TYPE: DNA
<213> ORGANISM: Homo sapiens

<400> SEQUENCE: 138
taaagttact tttcttttat tgactttccc ttattttta accttatgct tt    52

<210> SEQ ID NO 139
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 139
cagagttaaa aaaaaaaaaa aaaaaaagga agtagcagca acagcttgga aa    52

<210> SEQ ID NO 140
<211> LENGTH: 52
<212> TYPE: DNA
<213> ORGANISM: Homo sapiens

<400> SEQUENCE: 140
gttgcccagg gttgagtgca gaggcayatc ttggctcaca gcaacctctg cc    52

<210> SEQ ID NO 141
<211> LENGTH: 55
<212> TYPE: DNA
<213> ORGANISM: Homo sapiens
<220> FEATURE:
<221> NAME/KEY: misc_feature
<222> LOCATION: (27)..(30)
<223> OTHER INFORMATION: This region may or may not be present in its
      entirety

<400> SEQUENCE: 141
aaggcttttt tttttttttt tttttttttt gagacagagt cttgctgtgt caccc    55

<210> SEQ ID NO 142
<211> LENGTH: 52
<212> TYPE: DNA
<213> ORGANISM: Homo sapiens

<400> SEQUENCE: 142
gcctacattc tgcaaagagg agggaasatt cacagctcca tacttgaacc ct    52

<210> SEQ ID NO 143
<211> LENGTH: 52
<212> TYPE: DNA
<213> ORGANISM: Homo sapiens -continued

<400> SEQUENCE: 143
ccaaaggaga atagctctag gggaggsagg tggatgagta tgcatggggg ag                52

<210> SEQ ID NO 144
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 144
gactccatct caaaaaaaaa aaaaaatgc agtctaatgg cagaattaga ct                52

<210> SEQ ID NO 145
<211> LENGTH: 52
<212> TYPE: DNA
<213> ORGANISM: Homo sapiens

<400> SEQUENCE: 145
ttatttattt atttatttat ttttgaraca gggtctctgt tgtccaggct gg                52

<210> SEQ ID NO 146
<211> LENGTH: 52
<212> TYPE: DNA
<213> ORGANISM: Homo sapiens

<400> SEQUENCE: 146
ttttgaggca gggtctcact ctgttgycca gggttgagtg cagaggcaca tc                52

<210> SEQ ID NO 147
<211> LENGTH: 52
<212> TYPE: DNA
<213> ORGANISM: Homo sapiens

<400> SEQUENCE: 147
cgccttgcga aggccccaca gcttgcytgt gacaaacgtt cataggcaaa tg                52

<210> SEQ ID NO 148
<211> LENGTH: 52
<212> TYPE: DNA
<213> ORGANISM: Homo sapiens

<400> SEQUENCE: 148
ggaggtctgt acaaagcacc acctacytca tgggtcagtt tccacagcag aa                52

<210> SEQ ID NO 149
<211> LENGTH: 55
<212> TYPE: DNA
<213> ORGANISM: Homo sapiens
<220> FEATURE:
<221> NAME/KEY: misc_feature
<222> LOCATION: (27)..(30)
<223> OTHER INFORMATION: This region may or may not be present in its
      entirety

<400> SEQUENCE: 149
gaatcttata attcactgtg tacctccctc tgtttcatat tttcgcaatt gaact            55

<210> SEQ ID NO 150
<211> LENGTH: 52
<212> TYPE: DNA
<213> ORGANISM: Homo sapiens

<400> SEQUENCE: 150
aacatagtat ctaatatagc tttacaycca aagccaaaat atgaatacac tg      52

<210> SEQ ID NO 151
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 151
ttgttttgtt ttgtttgggg ggggggttg tttttctgag agggagtctt gc        52

<210> SEQ ID NO 152
<211> LENGTH: 52
<212> TYPE: DNA
<213> ORGANISM: Homo sapiens

<400> SEQUENCE: 152
cataccaaag ggcagctgga gggatayaga cggaagtcat gtggagagtg aa       52

<210> SEQ ID NO 153
<211> LENGTH: 52
<212> TYPE: DNA
<213> ORGANISM: Homo sapiens

<400> SEQUENCE: 153
caggtgtgag ccaccacgac caccaawtta gctcttttta ctccttccct tc       52

<210> SEQ ID NO 154
<211> LENGTH: 52
<212> TYPE: DNA
<213> ORGANISM: Homo sapiens

<400> SEQUENCE: 154
agtggtagct gattttgctt ctggatmctt tgccaccttc ccactcttta at       52

<210> SEQ ID NO 155
<211> LENGTH: 64
<212> TYPE: DNA
<213> ORGANISM: Homo sapiens
<220> FEATURE:
<221> NAME/KEY: misc_feature
<222> LOCATION: (27)..(39)
<223> OTHER INFORMATION: This region may or may not be present in its
      entirety

<400> SEQUENCE: 155
aaagacctgt ttcttaaaaa aaaaaagaa aaaaaaaag aaagaaaaga aaagaaaaaa  60
acag                                                            64

<210> SEQ ID NO 156
<211> LENGTH: 52
<212> TYPE: DNA
<213> ORGANISM: Homo sapiens

<400> SEQUENCE: 156
taaaaaatct ttcaatgagg agatgtyccc agagcaagac agctgtagga tg        52

<210> SEQ ID NO 157
<211> LENGTH: 52
<212> TYPE: DNA

```
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 157 aaagaaaaa aaaaaaaaaa aaaaaagaa aacaaaaccc aaacccataa ag       52

<210> SEQ ID NO 158
<211> LENGTH: 52
<212> TYPE: DNA
<213> ORGANISM: Homo sapiens

<400> SEQUENCE: 158
cctgtctcta aagaaaaaa aaaaaaraaa aaaaagaaa acaaaaccca aa        52

<210> SEQ ID NO 159
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 159
gttatcatag aaaatatca cactctgtct gtatccccac ttccagaaac tgt      53

<210> SEQ ID NO 160
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 160
caggagctca tagaattaca tacaatcttt tttttttttt tttgagacag cg      52

<210> SEQ ID NO 161
<211> LENGTH: 55
<212> TYPE: DNA
<213> ORGANISM: Homo sapiens
<220> FEATURE:
<221> NAME/KEY: misc_feature
<222> LOCATION: (27)..(30)
<223> OTHER INFORMATION: This region may or may not be present in its
      entirety

<400> SEQUENCE: 161
ttgagaatct tataattcac tgtgtacctc cctctgtttc atattttcgc aattg    55

<210> SEQ ID NO 162
<211> LENGTH: 52
<212> TYPE: DNA
<213> ORGANISM: Homo sapiens

<400> SEQUENCE: 162
ccactaccac agtgcctaga gaacaayatg tgtttaataa tatttaaata at       52

<210> SEQ ID NO 163
<211> LENGTH: 52
<212> TYPE: DNA
<213> ORGANISM: Homo sapiens
```

```
<220> FEATURE:
<221> NAME/KEY: misc_feature
<222> LOCATION: (27)..(27)
<223> OTHER INFORMATION: May or may not be present

<400> SEQUENCE: 163
ccctgtctct aaagaaaaa aaaaaaaaaa aaaaaagaa acaaaaccc aa         52

<210> SEQ ID NO 164
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 164
ccattatatc attcatttcc cactcatttt cttcattcca accaagatat at       52

<210> SEQ ID NO 165
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 165
tccgtctcaa aaaaaaaaa aaaaagagaa aggaattatt ctcatgtata ca        52

<210> SEQ ID NO 166
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 166
ctggggcagt taaaaagaaa acaaacccc tggtccctgc ccttgaggag at        52

<210> SEQ ID NO 167
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 167
ctccagggtc ccattccagg accacacgcc tgctacctct gcagctcact ca       52

<210> SEQ ID NO 168
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 168
ggattgacat ataccagtta gacggatttt tttttccat aaaccaggct ca        52
```

```
<210> SEQ ID NO 169
<211> LENGTH: 52
<212> TYPE: DNA
<213> ORGANISM: Homo sapiens

<400> SEQUENCE: 169
acaaataatt actacatatc tacaacrttc cagatacaga agaaatggcc aa          52

<210> SEQ ID NO 170
<211> LENGTH: 54
<212> TYPE: DNA
<213> ORGANISM: Homo sapiens
<220> FEATURE:
<221> NAME/KEY: misc_feature
<222> LOCATION: (27)..(29)
<223> OTHER INFORMATION: This region may or may not be present in its
      entirety

<400> SEQUENCE: 170
taaacacact tgaaacatca tataaaatga tattactaca agacttaacc gtaa        54

<210> SEQ ID NO 171
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 171
acacaggtaa tccatgttta ttatagaaaa atgccacatt actctttatt ga          52

<210> SEQ ID NO 172
<211> LENGTH: 53
<212> TYPE: DNA
<213> ORGANISM: Homo sapiens
<220> FEATURE:
<221> NAME/KEY: misc_feature
<222> LOCATION: (27)..(28)
<223> OTHER INFORMATION: This region may or may not be present in its
      entirety

<400> SEQUENCE: 172
agttatcata gaaaaatatc acactctgtc tgtatcccca cttccagaaa ctg         53

<210> SEQ ID NO 173
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 173
aatgaactta caggaaggta atatatggga aataaacatc ttattgaatt ta          52

<210> SEQ ID NO 174
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 174
```
ggacccctga aaggcacaag acacccttc aggttcacac ttcctgaaag ct    52

<210> SEQ ID NO 175
<211> LENGTH: 52
<212> TYPE: DNA
<213> ORGANISM: Homo sapiens

<400> SEQUENCE: 175
ccaccaatca ccagagcctt ctgctcrggg gtacctgagg gaaaacaagc aa    52

<210> SEQ ID NO 176
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 176
aaagactgaa aaaacattca taactatttt tcttgttatc ctcggaaatg tc    52

<210> SEQ ID NO 177
<211> LENGTH: 52
<212> TYPE: DNA
<213> ORGANISM: Homo sapiens

<400> SEQUENCE: 177
tatcttcatc ttggaggaga tgaggtygat ttcacctgct ggaagtccaa cc    52

<210> SEQ ID NO 178
<211> LENGTH: 52
<212> TYPE: DNA
<213> ORGANISM: Homo sapiens

<400> SEQUENCE: 178
ttgcctatga acgtttgtca cacttcygct gtgagttgct gaggcgaggt gt    52

<210> SEQ ID NO 179
<211> LENGTH: 52
<212> TYPE: DNA
<213> ORGANISM: Homo sapiens

<400> SEQUENCE: 179
gcttgctgtt ggatacatct cgccatyacc tgccactctc tagcatcctg ga    52

<210> SEQ ID NO 180
<211> LENGTH: 52
<212> TYPE: DNA
<213> ORGANISM: Homo sapiens

<400> SEQUENCE: 180
ccggggcttg ctgttggata catctckcca ttacctgcca ctctctagca tc    52

<210> SEQ ID NO 181
<211> LENGTH: 20
<212> TYPE: DNA
<213> ORGANISM: Homo sapiens

<400> SEQUENCE: 181
ctccgtttcg gtttcacttc    20

<210> SEQ ID NO 182

```
<211> LENGTH: 20
<212> TYPE: DNA
<213> ORGANISM: Homo sapiens

<400> SEQUENCE: 182
atcttctctt cagccctgct                                           20

<210> SEQ ID NO 183
<211> LENGTH: 20
<212> TYPE: DNA
<213> ORGANISM: Homo sapiens

<400> SEQUENCE: 183
gcacgatccg acggtagtgt                                           20

<210> SEQ ID NO 184
<211> LENGTH: 20
<212> TYPE: DNA
<213> ORGANISM: Homo sapiens

<400> SEQUENCE: 184
ccgtaatcgg gaagctgaag                                           20
```

METHODS AND COMPOSITIONS FOR EVALUATING GENETIC MARKERS

RELATED APPLICATIONS

This application is a continuation of U.S. application Ser. No. 15/231,687, filed Aug. 8, 2016, which is a continuation of U.S. application Ser. No. 13/266,862, filed Mar. 13, 2012, which is a national phase application that claims the benefit of, and priority to, international PCT Application No. PCT/US2010/001293, filed Apr. 30, 2010, which claims the benefit under 35 U.S.C. § 119(e) of U.S. Provisional Application No. 61/174,470, filed Apr. 30, 2009, U.S. Provisional Application No. 61/178,923, filed May 15, 2009, U.S. Provisional Application No. 61/179,358, filed May 18, 2009, and U.S. Provisional Application No. 61/182,089, filed May 28, 2009, the entire contents of each of which are incorporated herein by reference.

FIELD OF INVENTION

The invention relates to methods and compositions for determining genotypes in patient samples.

BACKGROUND OF THE INVENTION

Information about the genotype of a subject is becoming more important and relevant for a range of healthcare decisions as the genetic basis for many diseases, disorders, and physiological characteristics is further elucidated. Medical advice is increasingly personalized, with individual decisions and recommendations being based on specific genetic information. Information about the type and number of alleles at one or more genetic loci impacts disease risk, prognosis, therapeutic options, and genetic counseling amongst other healthcare considerations.

For cost-effective and reliable medical and reproductive counseling on a large scale, it is important to be able correctly and unambiguously identify the allelic status for many different genetic loci in many subjects.

Numerous technologies have been developed for detecting and analyzing nucleic acid sequences from biological samples. These technologies can be used to genotype subjects and determine the allelic status of any locus of interest. However, they are not sufficiently robust and cost-effective to be scaled up for reliable high throughput analysis of many genetic loci in large numbers of patients. The frequency of incorrect or ambiguous calls is too high for current technology to manage large numbers of patient samples without involving expensive and time-consuming steps to resolve uncertainties and provide confidence in the information output.

SUMMARY OF THE INVENTION

Aspects of the invention relate to preparative and analytical methods and compositions for evaluating genotypes, and in particular, for determining the allelic identity (or identities in a diploid organism) of one or more genetic loci in a subject.

Aspects of the invention are based, in part, on the identification of different sources of ambiguity and error in genetic analyses, and, in part, on the identification of one or more approaches to avoid, reduce, recognize, and/or resolve these errors and ambiguities at different stages in a genetic analysis.

According to aspects of the invention, certain types of genetic information can be under-represented or over-represented in a genetic analysis due to a combination of stochastic variation and systematic bias in any of the preparative stages (e.g., capture, amplification, etc.), determining stages (e.g., allele-specific detection, sequencing, etc.), data interpretation stages (e.g., determining whether the assay information is sufficient to identify a subject as homozygous or heterozygous), and/or other stages.

According to aspects of the invention, error or ambiguity may be apparent in a genetic analysis, but not readily resolved without running additional samples or more expensive assays (e.g., array-based assays may report no-calls due to noisy/low signal). According to further aspects of the invention, error or ambiguity may not be accounted for in a genetic analysis and incorrect base calls may be made even when the evidence for them is limited and/or not statistically significant (e.g., next-generation sequencing technologies may report base calls even if the evidence for them is not statistically significant). According to further aspects of the invention error or ambiguity may be problematic for a multi-step genetic analysis because it is apparent but not readily resolved in one or more steps of the analysis and not apparent or accounted for in other steps of the analysis.

In some embodiments, sources of error and ambiguity in one or more steps can be addressed by capturing and/or interrogating each target locus of interest with one or more sets of overlapping probes that are designed to overcome any systematic bias or stochastic effects that may impact the complexity and/or fidelity of the genetic information that is generated.

In some embodiments, sources of error and ambiguity in one or more steps can be addressed by capturing and/or interrogating each target locus of interest with at least one set of probes, wherein different probes are labeled with different identifiers that can be used to track the assay reactions and determine whether certain types of genetic information are under-represented or over-represented in the information that is generated.

In some embodiments, errors and ambiguities associated with the analysis of regions containing large numbers of sequence repeats are addressed by systematically analyzing frequencies of certain nucleic acids at particular stages in an assay (e.g., at a capture, sequencing, or detection stage). It should be appreciated that such techniques may be particularly useful in the context of a standardized protocol that is designed to allow many different loci to be evaluated in parallel without requiring different assay procedures for each locus. In some embodiments, the use of a single detection modality (e.g., sequencing) to assay multiple types of genetic lesions (e.g., point mutations, insertions/deletions, length polymorphisms) is advantageous in the clinical setting. In some embodiments of the invention, methods are provided that facilitate the use of multiple sample preparation steps in parallel, coupled with multiple analytical processes following sequence detection. Thus, in some embodiments of the invention, an improved workflow is provided that reduces error and uncertainty when simultaneously assaying different types of genetic lesions across multiple loci in multiple patients.

In some embodiments, aspects of the invention provide methods for overcoming preparative and/or analytical bias by combining two or more techniques, each having a different bias (e.g., a known bias towards under-representation or over-representation of one or more types of sequences), and using the resulting data to determine a genetic call for a subject with greater confidence.

It should be appreciated that in some embodiments, aspects of the invention relate to multiplex diagnostic methods. In some embodiments, multiplex diagnostic methods comprise capturing a plurality of genetic loci in parallel (e.g., one or more genetic loci from Table 1). In some embodiments, the genetic loci possess one or more polymorphisms (e.g., one or more polymorphisms from Table 2) the genotypes of which correspond to disease causing alleles. Accordingly, in some embodiments, the disclosure provides methods for assessing multiple heritable disorders in parallel. In some embodiments, methods are provided for diagnosing multiple heritable disorders in parallel at a pre-implantation, prenatal, perinatal, or postnatal stage. In some embodiments, the disclosure provides methods for analyzing multiple genetic loci (e.g., a plurality of target nucleic acids selected from Table 1) from a patient sample, such as a blood, pre-implantation embryo, chorionic villus or amniotic fluid sample, or other sample (e.g., other biological fluid or tissue sample such as a biopsy sample) as aspects of the invention are not limited in this respect.

Other samples may include tumor tissue or circulating tumor cells. In some embodiments, a patient sample (e.g., a tumor tissue or cell sample) is mosaic for one or more mutations of interest, and thus, may require higher sensitivity than is needed for a germline mutation analysis. In some embodiments, a sample comprises cells from a non-host organism (e.g., bacterial or viral infections in a human subject) or a sample for environmental monitoring (e.g., bacterial, viral, fungal composition of a soil, water, or air sample).

Accordingly, in some embodiments, aspects of the methods disclosed herein relate to genotyping a polymorphism of a target nucleic acid. In some embodiments, the genotyping may comprise determining that one or more alleles of the target nucleic acid are heterozygous or homozygous. In further embodiments, the genotyping may comprise determining the sequence of a polymorphism and comparing that sequence to a control sequence that is indicative of a disease risk. In some embodiments, the polymorphism is selected from a locus in Table 1 or Table 2. However, it should be appreciated that any locus associated with a disease or condition of interest may be used.

In some embodiments, a diagnosis, prognosis, or disease risk assessment is provided to a subject based on a genotype determined for that subject at one or more genetic loci (e.g., based on the analysis of a biological sample obtained from that subject). In some embodiments, an assessment is provided to a couple, based on their respective genotypes at one or more genetic loci, of the risk of their having one or more children having a genotype associated with a disease or condition (e.g., a homozygous or heterozygous genotype associated with a disease or condition). In some embodiments, a subject or a couple may seek genetic or reproductive counseling in connection with a genotype determined according to embodiments of the invention. In some embodiments, genetic information from a tumor or circulating tumor cells is used to determine prognosis and guide selection of appropriate drugs/treatments.

It should be appreciated that any of the methods or compositions described herein may be used in combination with any of the medical evaluations associated with one or more genetic loci as described herein.

In some embodiments, aspects of the invention provide effective methods for overcoming challenges associated with systematic errors (bias) and/or stochastic effects in multiplex genomic capture and/or analysis (including sequencing analysis). In some embodiments, aspects of the invention are useful to avoid, reduce and/or account for variability in one or more sampling and/or analytical steps. For example, in some embodiments, variability in target nucleic acid representation and unequal sampling of heterozygous alleles in pools of captured target nucleic acids can be overcome.

Accordingly, in some embodiments, the disclosure provides methods that reduce variability in the detection of target nucleic acids in multiplex capture methods. In other embodiments, methods improve allelic representation in a capture pool and, thus, improve variant detection outcomes. In certain embodiments, the disclosure provides preparative methods for capturing target nucleic acids (e.g., genetic loci) that involve the use of different sets of multiple probes (e.g., molecular inversion probes MIPs) that capture overlapping regions of a target nucleic acid to achieve a more uniform representation of the target nucleic acids in a capture pool compared with methods of the prior art. In other embodiments, methods reduce bias, or the risk of bias, associated with large scale parallel capture of genetic loci, e.g., for diagnostic purposes. In other embodiments, methods are provided for increasing reproducibility (e.g., by reducing the effect of polymorphisms on target nucleic acid capture) in the detection of a plurality of genetic loci in parallel. In further embodiments, methods are provided for reducing the effect of probe synthesis and/or probe amplification variability on the analysis of a plurality of genetic loci in parallel.

According to some aspects, methods of analyzing a plurality of genetic loci are provided. In some embodiments, the methods comprise contacting each of a plurality of target nucleic acids with a probe set, wherein each probe set comprises a plurality of different probes, each probe having a central region flanked by a 5' region and a 3' region that are complementary to nucleic acids flanking the same strand of one of a plurality of subregions of the target nucleic acid, wherein the subregions of the target nucleic acid are different, and wherein each subregion overlaps with at least one other subregion, isolating a plurality of nucleic acids each having a nucleic acid sequence of a different subregion for each of the plurality of target nucleic acids, and analyzing the isolated nucleic acids.

In other embodiments, methods comprise contacting each of a plurality of target nucleic acids with a probe set, wherein each probe set comprises a plurality of different probes, each probe having a central region flanked by a 5' region and a 3' region that are complementary to nucleic acids flanking the same strand of one of a plurality of subregions of the target nucleic acid, wherein the subregions of the target nucleic acid are different, and wherein a portion of the 5' region and a portion of the 3' region of a probe have, respectively, the sequence of the 5' region and the sequence of the 3' region of a different probe, isolating a plurality of nucleic acids each having a nucleic acid sequence of a different subregion for each of the plurality of target nucleic acids, and analyzing the isolated nucleic acids.

Aspects of the disclosure are based, in part, on the discovery of methods for overcoming problems associated with systematic and random errors (bias) in genome capture, amplification and sequencing methods, namely high variability in the capture and amplification of nucleic acids and disproportionate representation of heterozygous alleles in sequencing libraries. Accordingly, in some embodiments, the disclosure provides methods that reduce errors associated with the variability in the capture and amplification of nucleic acids. In other embodiments, the methods improve allelic representation in sequencing libraries and, thus, improve variant detection outcomes. In certain embodiments, the disclosure provides preparative methods for capturing target nucleic acids (e.g., genetic loci) that involve the use of differentiator tag sequences to uniquely tag individual nucleic acid molecules. In some embodiments, the differentiator tag sequence permit the detection of bias based on the occurrence of combinations of differentiator tag and target sequences observed in a sequencing reaction. In other embodiments, the methods reduce errors caused by bias, or the risk of bias, associated with the capture, amplification and sequencing of genetic loci, e.g., for diagnostic purposes.

Aspects of the invention relate to providing sequence tags (referred to as differentiator tags) that are useful to determine whether target nucleic acid sequences identified in an assay are from independently isolated target nucleic acids or from multiple copies of the same target nucleic acid molecule (e.g., due to bias in a preparative step, for example, amplification). This information can be used to help analyze a threshold number of independently isolated target nucleic acids from a biological sample in order to obtain sequence information that is reliable and can be used to make a genotype conclusion (e.g., call) with a desired degree of confidence. This information also can be used to detect bias in one or more nucleic acid preparative steps.

In some embodiments, the methods disclosed herein are useful for any application where reduction of bias, e.g., associated with genomic isolation, amplification, sequencing, is important. For example, detection of cancer mutations in a heterogeneous tissue sample, detection of mutations in maternally-circulating fetal DNA, and detection of mutations in cells isolated during a preimplantation genetic diagnostic procedure.

Accordingly, in some aspects, methods of genotyping a subject are provided. In some embodiments, the methods comprise determining the sequence of at least a threshold number of independently isolated nucleic acids, wherein the sequence of each isolated nucleic acid comprises a target nucleic acid sequence and a differentiator tag sequence, wherein the threshold number is a number of unique combinations of target nucleic acid and differentiator tag sequences, wherein the isolated nucleic acids are identified as independently isolated if they comprise unique combinations of target nucleic acid and differentiator tag sequences, and wherein the target nucleic acid sequence is the sequence of a genomic locus of a subject.

In some embodiments, the isolated nucleic acids are products of a circularization selection-based preparative method, e.g., molecular inversion probe capture products. In other embodiments, the isolated nucleic acids are products of an amplification-based preparative methods. In other embodiments, the isolated nucleic acids are products of hybridization-based preparative methods.

Circularization selection-based preparative methods selectively convert regions of interest (target nucleic acids) into a covalently-closed circular molecule which is then isolated typically by removal (usually enzymatic, e.g. with exonuclease) of any non-circularized linear nucleic acid. Oligonucleotide probes (e.g., molecular inversion probes) are designed which have ends that flank the region of interest (target nucleic acid) and, optionally, primer sites, e.g., sequencing primer sites. The probes are allowed to hybridize to the genomic target, and enzymes are used to first (optionally) fill in any gap between probe ends and second ligate the probe closed. Following circularization, any remaining (non-target) linear nucleic acid is typically removed, resulting in isolation (capture) of target nucleic acid. Circularization selection-based preparative methods include molecular inversion probe capture reactions and 'selector' capture reactions. In some embodiments, molecular inversion probe capture of a target nucleic acid is indicative of the presence of a polymorphism in the target nucleic acid.

In amplification-based (e.g., PCR-based or LCR-based, etc.) preparative methods, genomic loci (target nucleic acids) are isolated directly by means of a polymerase chain reaction or ligase chain reaction (or other amplification method) that selectively amplifies each locus using one or more oligonucleotide primers. It is to be understood that primers will be sufficiently complementary to the target sequence to hybridize with and prime amplification of the target nucleic acid. Any one of a variety of art known methods may be utilized for primer design and synthesis. One or more of the primers may be perfectly complementary to the target sequence. Degenerate primers may also be used. Primers may also include additional nucleic acids that are not complementary to target sequences but that facilitate downstream applications, including for example restriction sites and differentiator tag sequences. Amplification-based methods include amplification of a single target nucleic acid and multiplex amplification (amplification of multiple target nucleic acids in parallel).

Hybridization-based preparative methods involve selectively immobilizing target nucleic acids for further manipulation. It is to be understood that one or more oligonucleotides (immobilization oligonucleotides), which comprise differentiator tag sequences, and which may be from 15 to 170 nucleotides in length, are used which hybridize along the length of a target region of a genetic locus to immobilize it. In some embodiments, immobilization oligonucleotides, are either immobilized before hybridization is performed (e.g., Roche/Nimblegen 'sequence capture'), or are prepared such that they include a moiety (e.g. biotin) which can be used to selectively immobilize the target nucleic acid after hybridization by binding to e.g., streptavidin-coated microbeads (e.g. Agilent 'SureSelect').

It should be appreciated that any of the circularization, amplification, and/or hybridization based methods described herein may be used in connection with one or more of the tiling/staggering, tagging, size-detection, and/or sensitivity enhancing algorithms described herein.

In some embodiments, the methods disclosed herein comprise determining the sequence of molecular inversion probe capture products, each comprising a molecular inversion probe and a target nucleic acid, wherein the sequence of the molecular inversion probe comprises a differentiator tag sequence and, optionally, a primer sequence, and wherein the target nucleic acid is a captured genomic locus of a subject, and genotyping the subject at the captured genomic locus based on the sequence of at least a threshold number of unique combinations of target nucleic acid and differentiator tag sequences of molecular inversion probe capture products.

In some embodiments, the methods disclosed herein comprise obtaining molecular inversion probe capture products, each comprising a molecular inversion probe and a target nucleic acid, wherein the sequence of the molecular inversion probe comprises a differentiator tag sequence and, optionally, a primer sequence, wherein the target nucleic acid is a captured genomic locus of the subject, amplifying the molecular inversion probe capture products, and genotyping the subject by determining, for each target nucleic acid, the sequence of at least a threshold number of unique combinations of target nucleic acid and differentiator tag sequence of molecular inversion probe capture products. In certain embodiments, obtaining comprises capturing target nucleic acids from a genomic sample of the subject with molecular inversion probes, each comprising a unique differentiator tag sequence. In specific embodiments, capturing is performed under conditions wherein the likelihood of obtaining two or more molecular inversion probe capture products with identical combinations of target and differentiator tag sequences is equal to or less than a predetermined value, optionally wherein the predetermined value is about 0.05.

In one embodiment, the threshold number for a specific target nucleic acid sequence is selected based on a desired statistical confidence for the genotype. In some embodiments, the methods further comprising determining a statistical confidence for the genotype based on the number of unique combinations of target nucleic acid and differentiator tag sequences.

According to some aspects, methods of analyzing a plurality of genetic loci are provided. In some embodiments, the methods comprise obtaining a plurality of molecular inversion probe capture products each comprising a molecular inversion probe and a target nucleic acid, wherein the sequence of the molecular inversion probe comprises a differentiator tag sequence and, optionally, a primer sequence (e.g., a sequence that is complementary to the sequence of a nucleic acid that is used as a primer for sequencing or other extension reaction), amplifying the plurality of molecular inversion probe capture products, determining numbers of occurrence of combinations of target nucleic acid and differentiator tag sequence of molecular inversion probe capture products in the amplified plurality, and if the number of occurrence of a specific combination of target nucleic acid sequence and differentiator tag sequence exceeds a predetermined value, detecting bias in the amplification of the molecular inversion probe comprising the specific combination. In some embodiments, the methods further comprise genotyping target sequences in the plurality, wherein the genotyping comprises correcting for bias, if detected.

In some embodiments, the target nucleic acid is a gene (or portion thereof) selected from Table 1. In some embodiments, the genotyping comprises determining the sequence of a target nucleic acid (e.g., a polymorphic sequence) at one or more (both) alleles of a genome (a diploid genome) of a subject. In certain embodiments, the genotyping comprises determining the sequence of a target nucleic acid at both alleles of a diploid genome of a subject, wherein in the target nucleic acid comprises, or consists of, a sequence of Table 1, Table 2, or other locus of interest.

In some embodiments, aspects of the invention provide methods and compositions for identifying nucleic acid insertions or deletions in genomic regions of interest without determining the nucleotide sequences of these regions. Aspects of the invention are particularly useful for detecting nucleic acid insertions or deletions in genomic regions containing nucleic acid sequence repeats (e.g., di- or tri-nucleotide repeats). However, the invention is not limited to analyzing nucleic acid repeats and may be used to detect insertions or deletions in any target nucleic acid of interest. Aspects of the invention are particularly useful for analyzing multiple loci in a multiplex assay.

In some embodiments, aspects of the invention relate to determining whether an amount of target nucleic acid that is captured in a genomic capture assay is higher or lower than expected. In some embodiments, a statistically significant deviation from an expected amount (e.g., higher or lower) is indicative of the presence of a nucleic acid insertion or deletion in the genomic region of interest. In some embodiments, the amount is a number of nucleic acid molecules that are captured. In some embodiments, the amount is a number of independently captured nucleic acid molecules in a sample. It should be appreciated that the captured nucleic acids may be literally captured from a sample, or their sequences may be captured without actually capturing the original nucleic acids in the sample. For example, nucleic acid sequences may be captured in an assay that involves a template-based extension of nucleic acids having the region of interest, in the sample.

Aspects of the invention are based on the recognition that the efficiency of certain capture techniques is affected by the length of the nucleic acid being captured.

Accordingly, an increase or decrease in the length of a target nucleic acid (e.g., due to an insertion or deletion of a repeated sequence) can alter the capture efficiency of that nucleic acid. In some embodiments, a difference in the capture efficiency (e.g., a statistically significant difference in the capture efficiency) of a target nucleic acid is indicative of an insertion or deletion in the target nucleic acid. It should be appreciated that the capture efficiency for a target nucleic acid may be evaluated based on an amount of captured nucleic acid (e.g., number of captured nucleic acid molecules) relative to a control amount (e.g., based on an amount of control nucleic acid that is captured). However, the invention is not limited in this respect and other techniques for evaluating capture efficiency also may be used.

According to aspects of the invention, evaluating the capture efficiency as opposed to determining the sequence of the entire repeat region reduces errors associated with sequencing through repeat regions. Repeat sequences often give rise to stutters or skips in sequencing reactions that make it very difficult to accurately determine the number of repeats in a target region without running multiple sequencing reactions under different conditions and carefully analyzing the results. Such procedures are cumbersome and not readily scalable in a manner that is consistent with high throughput analyses of target nucleic acids. In some embodiments, repeat regions may be longer than the length of the individual sequence read, making length determination on the basis of a single read impossible. For example, when using next-generation sequencing the repeat regions may be longer than the length of the individual sequence read, making length determination on the basis of a single read impossible. Accordingly, aspects of the invention are useful to increase the sensitivity of detecting insertions or deletions in target regions, particularly target regions containing repeated sequences.

In some embodiments, aspects of the invention relate to capturing genomic nucleic acid sequences using a molecular inversion probe (e.g., MIP or Padlock probe) technique, and determining whether the amount (e.g., number) of captured sequences is higher or lower than expected. In some embodiments, the amount (e.g., number) of captured sequences is compared to an amount (e.g., number) of sequences captured in a control assay. The control assay may involve analyzing a control sample that contains a nucleic acid from the same genetic locus having a known sequence length (e.g., a known number of nucleic acid repeats). However, a control may involve analyzing a second (e.g., different) genetic locus that is not expected to contain any insertions or deletions. The second genetic locus may be analyzed in the same sample as the locus being interrogated or in a different sample where its length has been previously determined. The second genetic locus may be a locus that is not characterized by the presence of nucleic acid repeats (and thus not expected to contain insertions or deletions of the repeat sequence).

In some embodiments, a target nucleic acid region that is being evaluated may be determined by the identity of the targeting arms of a probe that is designed to capture the target region (or sequence thereof). For example, the targeting arms of a MIP probe may be designed to be complementary (e.g., sufficiently complementary for selective hybridization and//or polymerase extension and/or ligation) to genomic regions flanking a target region suspected of containing an insertion or deletion. It should be appreciated that two targeting arms may be designed to be complementary (e.g., sufficiently complementary for selective hybridization and/or polymerase extension and/or ligation) to the two flanking regions that are immediately adjacent (e.g., immediately 5' and 3', respectively) to a region of a sequence repeat on one strand of a genomic nucleic acid. However, one or both targeting arms may be designed to hybridize several bases (e.g., 1-5, 5-10, 10-25, 25-50, or more) upstream or downstream from the repeat region in such a way that the captured sequence includes a region of unique genomic sequence that on one or both sides of the repeat region. This unique region can then be used to identify the captured target (e.g., based on sequence or hybridization information).

In some embodiments, two or more (e.g., 2, 3, 4, 5, 6, 7, 8, 9, 10 or more) different loci may be interrogated in parallel in a single assay (e.g., in a multiplex assay). In some embodiments, the ratio of captured nucleic acids for each locus may be used to determine whether a nucleic acid insertion or deletion is present in one locus relative to the other. For example, the ratio may be compared to a control ratio that is representative of the two loci when neither one has an insertion or deletion relative to control sequences (e.g., sequences that are normal or known to be associated with healthy phenotypes for those loci). However, the amount of captured nucleic acids may be compared to any suitable control as discussed herein.

The locus of a captured sequence may be identified by determining a portion of unique sequence 5' and/or 3' to the repeat region in the target nucleic acid suspected of containing a deletion or insertion. This does not require sequencing the captured repeat region itself. However, some or all of the repeat region also could be sequenced as aspects of the invention are not limited in this respect.

Aspects of the invention may be combined with one or more sequence-based assays (e.g., SNP detection assays), for example in a multiplex format, to determine the genotype of one or more regions of a subject.

In some embodiments, methods of detecting a polymorphism in a nucleic acid in a biological sample are provided. In some embodiments, the methods comprise evaluating the efficiency of capture at one or more loci and determining whether one or both alleles at that locus contain an insertion or deletion relative to a control locus (e.g., a locus indicative of a length of repeat sequence that is associated with a healthy phenotype).

Accordingly, aspects of the invention relate to methods for determining whether a target nucleic acid has an abnormal length by evaluating the capture efficiency of a target nucleic acid in a biological sample from a subject, wherein a capture efficiency that is different from a reference capture efficiency is indicative of the presence, in the biological sample, of a target nucleic acid having an abnormal length. It should be appreciated that the term "abnormal" is a relative term based on a comparison to a "normal" length. In some embodiments, a normal length is a length that is associated with a normal (e.g., healthy or non-carrier phenotype). Accordingly, an abnormal length is a length that is either shorter or longer than the normal length. In some embodiments, the presence of an abnormal length is indicative of an increased risk that the locus is associated with a disease or a disease carrier phenotype. In some embodiments, the abnormal length is indicative that the subject is either has a disease or condition or is a carrier of a disease or condition (e.g., associated with the locus). However, it should be appreciated that the description of embodiments relating to detecting the presence of an abnormal length also support detecting the presence of a length that is different from an expected or control length.

In some embodiments, aspects of the invention relate to estimating the length of a target nucleic acid (e.g., of a sub-target region within a target nucleic acid). In some embodiments, aspects of the invention relate to methods for estimating the length of a target nucleic acid by contacting the target nucleic acid with a plurality of detection probes under conditions that permit hybridization of the detection probes to the target nucleic acid, wherein each detection probe is a polynucleotide that comprises a first arm that hybridizes to a first region of the target nucleic acid and a second arm that hybridizes to a second region of the target nucleic acid, wherein the first and second regions are on a common strand of the target nucleic acid, and wherein the nucleotide sequence of the target between the 5' end of the first region and the 3' end of the second region is the nucleotide sequence of a sub-target nucleic acid; and capturing a plurality of sub-target nucleic acids that are hybridized with the plurality of detection probes; and measuring the frequency of occurrence of a sub-target nucleic acid in the plurality of sub-target nucleic acids, wherein the frequency of occurrence of the sub-target nucleic acid in the plurality of sub-target nucleic acids is indicative of the length of the sub-target nucleic acid. It should be appreciated that methods for estimating a nucleic acid length may involve comparing a capture efficiency for a target nucleic acid region to two or more reference efficiencies for known nucleic acid lengths in order to determine whether the target nucleic acid region is smaller, intermediate, or larger in size than the known control lengths. In some embodiments, a series of nucleic acids of known different lengths may be used to provide a calibration curve for evaluating the length of a target nucleic acid region of interest.

In some embodiments, the capture efficiency of a target region suspected of having a deletion or insertion is determined by comparing the capture efficiency to a reference indicative of a normal capture efficiency. In some embodiments, the capture efficiency is lower than the reference capture efficiency. In some embodiments, the subject is identified as having an insertion in the target region. In some embodiments, the capture efficiency is higher than the reference capture efficiency. In some embodiments, the subject is identified as having a deletion in the target region. In some embodiments, the subject is identified as being heterozygous for the insertion. In some embodiments, the subject is identified as being heterozygous for the deletion.

In some embodiments of any of the methods described herein (e.g., tiling/staggering, tagging, size-detection, and/or sensitivity enhancement) aspects of the invention relate to capturing a sub-target nucleic acid (or a sequence of a sub-target nucleic acid). In some embodiments, a molecular inversion probe technique is used. In some embodiments, a molecular inversion probe is a single linear strand of nucleic acid that comprises a first targeting arm at its 5' end and a second targeting arm at its 3' end, wherein the first targeting arm is capable of specifically hybridizing to a first region flanking one end of the sub-target nucleic acid, and wherein the second targeting arm is capable of specifically hybridizing to a second region flanking the other end of the sub target nucleic acid on the same strand of the target nucleic acid. In some embodiments, the first and second targeting arms are between about 10 and about 100 nucleotides long. In some embodiments, the first and second targeting arms are about 10-20, 20-30, 30-40, or 40-50 nucleotides long. In some embodiments, the first and second targeting arms are about 20 nucleotides long. In some embodiments, the first and second targeting arms have the same length. In some embodiments, the first and second targeting arms have different lengths. In some embodiments, each pair of first and second targeting arms in a set of probes has the same length. Accordingly, if one of the targeting arms is longer, the other one is correspondingly shorter. This allows for a quality control step in some embodiments to confirm that all captured probe/target sequence products have the same length after a multiplexed plurality of capture reactions. In some embodiments, a set of probes may be designed to have the same length if the intervening region is varied to accommodate any differences in the length of either one or both of the first and second targeting arms.

In some embodiments, the hybridization Tms of the first and second targeting arms are similar. In some embodiments, the hybridization Tms of the first and second targeting arms are within 2-5° C. of each other. In some embodiments, the hybridization Tms of the first and second targeting arms are identical. In some embodiments, the hybridization Tms of the first and second targeting arms are close to empirically-determined optima but not necessarily identical.

In some embodiments, the first and second targeting arms of a molecular inversion probe have different Tms. For example, the Tm of the first targeting arm (at the 5' end of the molecular inversion probe) may be higher than the Tm of the second targeting arm (at the 3' end of the molecular inversion probe). According to aspects of the invention, and without wishing to be bound by theory, a relatively high Tm for the first targeting arm may help avoid or prevent the first targeting arm from being displaced after hybridization by the extension product of the 3' end of the second targeting arm. It should be appreciated that a reference to the Tm of a targeting arm as used herein relates to the Tm of hybridization of the targeting arm to a nucleic acid having the complementary sequence (e.g., the region of the target nucleic acid that has a sequence that is complementary to the sequence of the targeting arm). It also should be appreciated that the Tms of the targeting arms described herein may be calculated using any appropriate method. For example, in some embodiments an experimental method (e.g., a gel shift assay, a hybridization assay, a melting curve analysis, for example in a PCR machine with a SYBR dye by stepping through a temperature ramp while monitoring signal level from an intercalating dye, for example, bound to a double-stranded DNA, etc.) may be used to determine one or more Tms empirically. In some embodiments, an optimal Tm may be determined by evaluating the number of products formed (e.g., for each of a plurality of MIP probes), and determining the optimal Tm as the center point in a histogram of Tm for all targeting arms. In some embodiments, a predictive algorithm may be used to determine a Tm theoretically. In some embodiments, a relatively simple predictive algorithm may be used based on the number of G/C and A/T base pairs when the sequence is hybridized to its target and/or the length of the hybridized product (e.g., for example, 64.9+ 41*([G+C]−16.4)/(A+T+G+C), see for example, Wallace, R. B., Shaffer, J., Murphy, R. F., Bonner, J., Hirose, T., and Itakura, K. (1979) Nucleic Acids Res 6:3543-3557). In some embodiments, a more complex algorithm may be used to account for the effects of base stacking entropy and enthalpy, ion concentration, and primer concentration (see, for example, SantaLucia J (1998), Proc Natl Acad Sci USA, 95:1460-5). In some embodiments an algorithm may use modified parameters (e.g., nearest-neighbor parameters for basepair entropy/enthalpy values). It should be appreciated that any suitable algorithm may be used as aspects of the invention are not limited in this respect. However, it also should be appreciated that different methodologies may results in different calculated or predicted Tms for the same sequences. Accordingly, in some embodiments, the same empirical and/or theoretical method is used to determine the Tms of different sequences for a set of probes to avoid a negative impact of any systematic difference in the Tm determination or prediction when designing a set of probes with predetermined similarities or differences for different Tms.

In some embodiments, the Tm of the first targeting arm may be about 1° C., about 2° C., about 3° C., about 4° C., about 5° C., or more than about 5° C. higher than the Tm of the second targeting arm. In some embodiments, each probe in a plurality of probes (e.g., each probe in a set of 5-10, each probe in a set of at least 10, each probe in a set of 10-50, each probe in a set of 50-100, each probe in a set of 100-500, each probe in a set of 500-1,000, each probe in a set of 1,000-1,500, each probe in a set of 1,500-2,000, each probe in a set of 2,000-3,000, 3,000-5,000, 5,000-10,000 or each probe in a set of at least 5,000 different probes) has a unique first targeting arm (e.g., they all have different sequences) and a unique second targeting arm (e.g., they all have different sequences). In some embodiments, for at least 10% of the probes (e.g., at least 25%, 25%-50%, 50%-75%, 75%-90%, 90%-95% or over 95%, or all of the probes) the first targeting arm has a Tm for its complementary sequence that is higher (e.g., about 1° C., about 2° C., about 3° C., about 4° C., about 5° C., or more than about 5° C. higher) than the Tm of the second targeting arm for its complementary sequence. In some embodiments, each of the first targeting arms have similar or identical Tms for their respective complementary sequences and each of the second targeting arms have similar or identical Tms for their respective complementary sequences (and the first targeting arms have higher Tms than the second targeting arms). For example, in some embodiments, the Tm of the first arm(s) may be about 58° C. and the Tm of the second arm(s) may be about 56° C. In some embodiments, the Tm of the first arm(s) may be about 68° C., and the Tm of the second arm(s) may be about 65° C. It should be appreciated that in some embodiments the similarity (e.g., within a range of 1° C., 2° C., 3° C., 4° C., 5° C.) or identity of the Tms for the different targeting arms should be based either on empirical data for each arm or based on the same predictive algorithm for each arm (e.g., Wallace, R. B., Shaffer, J., Murphy, R. F., Bonner, J., Hirose, T., and Itakura, K. (1979) Nucleic Acids Res 6:3543-3557, SantaLucia J (1998), Proc Natl Acad Sci USA, 95:1460-5, or other algorithm).

In some embodiments, the Tm of the first targeting arm of a molecular inversion probe (at the 5' end of the molecular inversion probe) is selected to be sufficiently stable to prevent displacement of the first targeting arm from its complementary sequence on a target nucleic acid. In some embodiments, the Tm of the first targeting arm is 50-55° C., at least 55° C., 55-60° C., at least 60° C., 60-65° C., at least 65° C., at least 70° C., at least 75° C., or at least 80° C. As discussed above, it should be appreciated that the for a particular targeting arm may be determined empirically or theoretically. Different theoretical models may be used to determine a Tm and it should be appreciated that the predicted Tm for a particular sequence may be different depending on the algorithm used for the prediction. In some embodiments, each probe in a plurality of probes (e.g., each probe in a set of 5-10, each probe in a set of at least 10, each probe in a set of 10-50, each probe in a set of 50-100, each probe in a set of 100-500, or each probe in a set of at least 500 different probes) has a different first targeting arm (e.g., different sequences) but each different first targeting arm has a similar or identical Tm for its complementary sequence on a target nucleic acid. It should be appreciated that in some embodiments the similarity (e.g., within a range of I C, 2 C, 3 C, 4 C, 5 C) or identity of the Tms for the different targeting arms should be based either on empirical data for each arm or based on the same predictive algorithm for each arm (e.g., Wallace, R. B., Shaffer, J., Murphy, R. F., Bonner, J., Hirose, T., and Itakura, K. (1979) Nucleic Acids Res 6:3543-3557, SantaLucia J (1998), Proc Natl Acad Sci USA, 95:1460-5, or other algorithm).

In some embodiments, the sub-target nucleic acid contains a nucleic acid repeat. In some embodiments, the nucleic acid repeat is a dinucleotide or trinucleotide repeat. In some embodiments, the sub-target nucleic acid contains 10-100 copies of the nucleic acid repeat in the absence of an abnormal increase or decrease in nucleic acid repeats. In some embodiments, the sub-target nucleic acid is a region of the Fragile-X locus that contains a nucleic acid repeat. In some embodiments, one or both targeting arms hybridize to a region on the target nucleic acid that is immediately adjacent to a region of nucleic acid repeats. In some embodiments, one or both targeting arms hybridize to a region on the target nucleic acid that is separated from a region of nucleic acid repeats by a region that does not contain any nucleic acid repeats. In some embodiments, the molecular inversion probe further comprises a primer-binding region that can be used to sequence the captured sub-target nucleic acid and optionally the first and/or second targeting arm.

In some embodiments, aspects of the invention relate to evaluating the length of a plurality of different target nucleic acids in a biological sample. In some embodiments, the plurality of target nucleic acids are analyzed using a plurality of different molecular inversion probes. In some embodiments, each different molecular inversion probe comprises a different pair of first and second targeting arms at each of the 3' and 5' ends. In some embodiments, each different molecular inversion probe comprises the same primer-binding sequence.

In some embodiments, aspects of the invention relate to analyzing nucleic acid from a biological sample obtained from a subject. In some embodiments, the biological sample is a blood sample. In some embodiments, the biological sample is a tissue sample, specific cell population, tumor sample, circulating tumor cells, or environmental sample. In some embodiments, the biological sample is a single cell. In some embodiments, nucleic acids are analyzed in biological samples obtained from a plurality of different subjects. In some embodiments, nucleic acids from a biological sample are analyzed in multiplex reactions. It should be appreciated that a biological sample contains a plurality of copies of a genome derived from a plurality of cells in the sample. Accordingly, a sample may contain a plurality of independent copies of a target nucleic acid region of interest, the capture efficiency of which can be used to evaluate its size as described herein.

In some embodiments, aspects of the invention relate to evaluating a nucleic acid capture efficiency by determining an amount of target nucleic acid that is captured (e.g., an amount of sub-target nucleic acid sequences that are captured). In some embodiments, the amount of target nucleic acid that is captured is determined by determining a number of independently captured target nucleic acid molecules (e.g., the amount of independently captured molecules that have the sequence of the sub-target region). In some embodiments, the amount of target nucleic acid that is captured is compared to a reference amount of captured nucleic acid. In some embodiments, the reference amount is determined by determining a number of independently captured molecules of a reference nucleic acid. In some embodiments, the reference nucleic acid is a nucleic acid of a different locus in the biological sample that is not suspected of containing a deletion or insertion. In some embodiments, the reference nucleic acid is a nucleic acid of known size and amount that is added to the capture reaction. As described herein, a number of independently captured nucleic acid sequences can be determined by contacting a nucleic acid sample with a preparation of a probe (e.g., a MIP probe as described herein). It should be appreciated that the preparation may comprise a plurality of copies of the same probe and accordingly a plurality of independent copies of the target region may be captured by different probe molecules. The number of probe molecules that actually capture a sequence can be evaluated by determining an amount or number of captured molecules using any suitable technique. This number is a reflection of both the number of target molecules in the sample and the efficiency of capture of those target molecules, which in turn is related to the size of the target molecules as described herein. Accordingly, the capture efficiency can be evaluated by controlling for the abundance of the target nucleic acid, for example by comparing the number or amount of captured target molecules to an appropriate control (e.g., a known size and amount of control nucleic acid, or a different locus that should be present in the same amount in the biological sample and is not expected to contain any insertions or deletions). It should be appreciated that other factors may affect the capture efficiency of a particular target nucleic acid region (e.g., the sequence of the region, the GC content, the presence of secondary structures, etc.). However, these factors also can be accounted for by using appropriate controls (e.g., known sequences having similar properties, the same sequences, other genomic sequences expected to be present in the biological sample at the same frequency, etc., or any combination thereof).

In some embodiments, aspects of the invention relate to identifying a subject as having an insertion or deletion in one or more alleles of a genetic locus if the capture efficiency for that genetic locus is statistically significantly different than a reference capture efficiency.

It should be appreciated that hybridization conditions used for any of the capture techniques described herein (e.g., MIP capture techniques) can be based on known hybridization buffers and conditions.

In some embodiments, the methods disclosed herein are useful for any application where the detection of deletions or insertions is important.

In some embodiments, aspects of the invention relate to basing a nucleic acid sequence analysis on results from two or more different nucleic acid preparatory techniques that have different systematic biases in the types of nucleic acids that they sample. According to the invention, different techniques have different sequence biases that are systematic and not simply due to stochastic effects during nucleic acid capture or amplification. Accordingly, the degree of oversampling required to overcome variations in nucleic acid preparation needs to be sufficient to overcome the biases (e.g., an oversampling of 2-5 fold, 5-10 fold, 5-15 fold, 15-20 fold, 20-30 fold, 30-50 fold, or intermediate to higher fold).

According to some embodiments, different techniques have different characteristic or systematic biases. For example, one technique may bias a sample analysis towards one particular allele at a genetic locus of interest, whereas a different technique would bias the sample analysis towards a different allele at the same locus. Accordingly, the same sample may be identified as being different depending on the type of technique that is used to prepare nucleic acid for sequence analysis. This effectively represents a sensitivity limitation, because each technique has different relative sensitivities for polymorphic sequences of interest.

According to aspects of the invention, the sensitivity of a nucleic acid analysis can be increased by combining the sequences from different nucleic acid preparative steps and using the combined sequence information for a diagnostic assay (e.g., for a making a call as to whether a subject is homozygous or heterozygous at a genetic locus of interest).

In some embodiments, the invention provides a method of increasing the sensitivity of a nucleic acid detection assay by obtaining a first preparation of a target nucleic acid using a first preparative method on a biological sample, obtaining a second preparation of a target nucleic acid using a second preparative method on the biological sample, assaying the sequences obtained in both first and second nucleic acid preparations, and using the sequence information from both first and second nucleic acid preparations to determine the genotype of the target nucleic acid in the biological sample, wherein the first and second preparative methods have different systematic sequence biases. In some embodiments, the first and second nucleic acid preparations are combined prior to performing a sequence assay. In some embodiments, separate sequence assays are performed on the first and second nucleic acid preparations and the sequence information from both assays are combined to determine the genotype of the target nucleic acid in the biological sample. In some embodiments, the first preparative method is an amplification-based, a hybridization-based, or a circular probe-based preparative method. In some embodiments, the second method is an amplification-based, a hybridization-based, or a circular probe-based preparative method. In some embodiments, the first and second methods are of different types (e.g., only one of them is an amplification-based, a hybridization-based, or a circular probe-based preparative method, and the other one is one or the other two types of method). Accordingly, in some embodiments the second preparative method is an amplification-based, a hybridization-based, or a circular probe-based preparative method, provided that the second method is different from the first method. However, in some embodiments, both methods may be of the same type, provided they are different methods (e.g., both are amplification based or hybridization-based, but are different types of amplification or hybridization methods, e.g., with different relative biases).

In amplification-based (e.g., PCR-based or LCR-based, etc.) preparative methods, genomic loci (target nucleic acids) are isolated directly by means of a polymerase chain reaction or ligase chain reaction (or other amplification method) that selectively amplifies each locus using a pair of oligonucleotide primers. It is to be understood that primers will be sufficiently complementary to the target sequence to hybridize with and prime amplification of the target nucleic acid. Any one of a variety of art known methods may be utilized for primer design and synthesis. One or both of the primers may be perfectly complementary to the target sequence. Degenerate primers may also be used. Primers may also include additional nucleic acids that are not complementary to target sequences but that facilitate downstream applications, including for example restriction sites and identifier sequences (e.g., source sequences). PCR based methods may include amplification of a single target nucleic acid and multiplex amplification (amplification of multiple target nucleic acids in parallel).

Hybridization-based preparative may methods involve selectively immobilizing target nucleic acids for further manipulation. It is to be understood that one or more oligonucleotides (immobilization oligonucleotides), which in some embodiments may be from 10 to 200 nucleotides in length, are used which hybridize along the length of a target region of a genetic locus to immobilize it. In some embodiments, immobilization oligonucleotides are either immobilized before hybridization is performed (e.g., Roche/Nimblegen 'sequence capture'), or are prepared such that they include a moiety (e.g., biotin) which can be used to selectively immobilize the target nucleic acid after hybridization by binding to e.g., streptavidin-coated microbeads (e.g., Agilent 'SureSelect').

Circularization selection-based preparative methods selectively convert each region of interest into a covalently-closed circular molecule which is then isolated by removal (usually enzymatic, e.g., with exonuclease) of any non-circularized linear nucleic acid. Oligonucleotide probes are designed which have ends that flank the region of interest. The probes are allowed to hybridize to the genomic target, and enzymes are used to first (optionally) fill in any gap between probe ends and second ligate the probe closed. In some embodiments, following circularization, any remaining (non-target) linear nucleic acid can be removed, resulting in isolation (capture) of target nucleic acid. Circularization selection-based preparative methods include molecular inversion probe capture reactions and 'selector' capture reactions. However, other techniques may be used as aspects of the invention are not limited in this respect. In some embodiments, molecular inversion probe capture of a target nucleic acid is indicative of the presence of a polymorphism in the target nucleic acid.

A variety of methods may be used to evaluate and compare bias profiles of each preparative technique. Next-generation sequencing may be used to quantitatively measure the abundance of each isolated target nucleic acid obtained from a certain preparative method. This abundance may be compared to a control abundance value (e.g., a known starting abundance of the target nucleic acid) and/or with an abundance determined through the use of an alternative preparative method. For example, a set of target nucleic acids may be isolated by one or more of the three preparative methods; the target nucleic acid may be observed x times using the amplification technique, y times using the hybridization enrichment technique, and z times using the circularization selection technique. A pairwise correlation coefficient may be computed between each abundance value (e.g., x and y, x and z, and y and z) to assess bias in nucleic acid isolation between pairs of preparative methods. Since the mechanisms of isolation are different in each approach, the abundances will usually be different and largely uncorrelated with each other.

In some embodiments, the invention provides a method of obtaining a nucleic acid preparation that is representative of a target nucleic acid in a biological sample by obtaining a first preparation of a target nucleic acid using a first preparative method on a biological sample, obtaining a second preparation of a target nucleic acid using a second preparative method on the biological sample, and combining the first and second nucleic acid preparations to obtain a combined preparation that is representative of the target nucleic acid in the biological sample.

In some embodiments of any of the methods described herein, a third preparation of the target nucleic acid is obtained using a third preparative method that is different from the first and second preparative methods, wherein the first, second, and third preparative methods all have different systematic sequence biases. In some embodiments of any of the methods described herein, the different preparative methods are used for a plurality of different loci in the biological sample to increase the sensitivity of a multiplex nucleic acid analysis. In some embodiments, the target nucleic acid has a sequence of a gene selected from Table 1.

However, it should be appreciated that a genotyping method of the invention may include several steps, each of which independently may involve one or more different preparative techniques described herein. In some embodiments, a nucleic acid preparation may be obtained using one or more (e.g., 2, 3, 4, 5, or more) different techniques described herein (e.g., amplification, hybridization capture, circular probe capture, etc., or any combination thereof) and the nucleic acid preparation may be analyzed using one or more different techniques (e.g., amplification, hybridization capture, circular probe capture, etc., or any combination thereof) that are selected independently of the techniques used for the initial preparation.

In some embodiments, aspects of the invention also provide compositions, kits, devices, and analytical methods for increasing the sensitivity of nucleic acid assays. Aspects of the invention are particularly useful for increasing the confidence level of genotyping analyses. However, aspects of the invention may be used in the context of any suitable nucleic acid analysis, for example, but not limited to, a nucleic acid analysis that is designed to determine whether more than one sequence variant is present in a sample.

In some embodiments, aspects of the invention relate to a plurality of nucleic acid probes (e.g., 10-50, 50-100, 100-250, 250-500, 500-1,000, 1,000-2,000, 2,000-5,000, 5,000-7,500, 7,500-10,000, or lower, higher, or intermediate number of different probes).

In some embodiments, each probe or each of a subset of probes (e.g., 10-25%, 25-50%, 50-75%, 75-90%, or 90-99%) has a different first targeting arm. In some embodiments, each probe or each probe of a subset of probes (e.g., 10-25%, 25-50%, 50-75%, 75-90%, or 90-99%) has a different second targeting arm. In some embodiments, the first and second targeting arms are separated by the same intervening sequence. In some embodiments, the first and second targeting arms are complementary to target nucleic acid sequences that are separated by the same or a similar length (e.g., number of nucleic acids, for example, 0-25, 25-50, 50-100, 100-250, 250-500, 500-1,000, 1,000-2,500 or longer or intermediate number of nucleotides) on their respective target nucleic acids (e.g., genomic loci). In some embodiments, each probe or a subset of probes (e.g., 10-30 25%, 25-50%, 50-75%, 75-90%, or 90-99%) includes a first primer binding sequence. In some embodiments, the primer binding sequence is the same (e.g., it can be used to prime sequencing or other extension reaction). In some embodiments, each probe or a subset of probes (e.g., 10-25%, 25-50%, 50-75%, 75-90%, or 90-99%) includes a unique identifier sequence tag (e.g., that is predetermined and can be used to distinguish each probe).

In some embodiments, the methods disclosed herein are useful for any application where sensitivity is important. For example, detection of cancer mutations in a heterogenous tissue sample, detection of mutations in maternally-circulating fetal DNA, and detection of mutations in cells isolated during a preimplantation genetic diagnostic procedure.

According to some aspects of the invention, methods of detecting a polymorphism in a nucleic acid in a biological sample are provided. In some embodiments, the methods comprise obtaining a nucleic acid preparation using a preparative method (e.g., any of the preparative methods disclosed herein) on a biological sample, and performing a molecular inversion probe capture reaction on the nucleic acid preparation, wherein a molecular inversion probe capture (e.g., using a mutation-detection MIP) of a target nucleic acid of the nucleic acid preparation is indicative of the presence of a mutation (polymorphism) in the target nucleic acid, optionally wherein the polymorphism is selected from Table 2.

According to some aspects of the invention, methods of genotyping a nucleic acid in a biological sample are provided. In some embodiments, the methods comprise obtaining a nucleic acid preparation using a preparative method on a biological sample, sequencing a target nucleic acid of the nucleic acid preparation, and performing a molecular inversion probe capture reaction on the biological sample, wherein a molecular inversion probe capture of the target nucleic acid in the biological sample is indicative of the presence of a polymorphism in the target nucleic acid, genotyping the target nucleic acid based on the results of the sequencing and the capture reaction.

In some embodiments of the methods disclosed herein, the target nucleic acid has a sequence of a gene selected from Table 1.

It should be appreciated that any one or more embodiments described herein may be used for evaluating multiple genetic markers in parallel. Accordingly, in some embodiments, aspects of the invention relate to determining the presence of one or more markers (e.g., one or more alleles) at multiple different genetic loci in parallel.

Accordingly, the risk or presence of multiple heritable disorders may be evaluated in parallel. In some embodiments, the risk of having offspring with one or more heritable disorders may be evaluated. In some embodiments, an evaluation may be performed on a biological sample of a parent or a child (e.g., at a pre-implantation, prenatal, perinatal, or postnatal stage).

In some embodiments, the disclosure provides methods for analyzing multiple genetic loci (e.g., a plurality of target nucleic acids selected from Table 1 or 2) from a patient sample, such as a blood, pre-implantation embryo, chorionic villus or amniotic fluid sample. A patient or subject may be a human. However, aspects of the invention are not limited to humans and may be applied to other species (e.g., mammals, birds, reptiles, other vertebrates or invertebrates) as aspects of the invention are not limited in this respect. A subject or patient may be male or female. In some embodiments, in connection with reproductive genetic counseling, samples from a male and female member of a couple may be analyzed. In some embodiments, for example, in connection with an animal breeding program, samples from a plurality of male and female subjects may be analyzed to determine compatible or optimal breeding partners or strategies for particular traits or to avoid one or more diseases or conditions. Accordingly, reproductive risks may be determined and/or reproductive recommendations may be provided based on information derived from one or more embodiments of the invention.

However, it should be appreciated that aspects of the invention may be used in connection with any medical evaluation where the presence of one or more alleles at a genetic locus of interest is relevant to a medical determination (e.g., risk or detection of disease, disease prognosis, therapy selection, therapy monitoring, etc.). Further aspects of the invention may be used in connection with detection, in tumor tissue or circulating tumor cells, of mutations in cellular pathways that cause cancer or predict efficacy of treatment regimens, or with detection and identification of pathogenic organisms in the environment or a sample obtained from a subject, e.g., a human subject.

These and other aspects of the invention are described in more detail in the following description and non-limiting examples and drawings.

BRIEF DESCRIPTION OF DRAWINGS

FIG. 10 illustrates a non-limiting hypothetical relationship between target gap size and the relative number of reads of the repetitive region;

DETAILED DESCRIPTION

Figure 1:
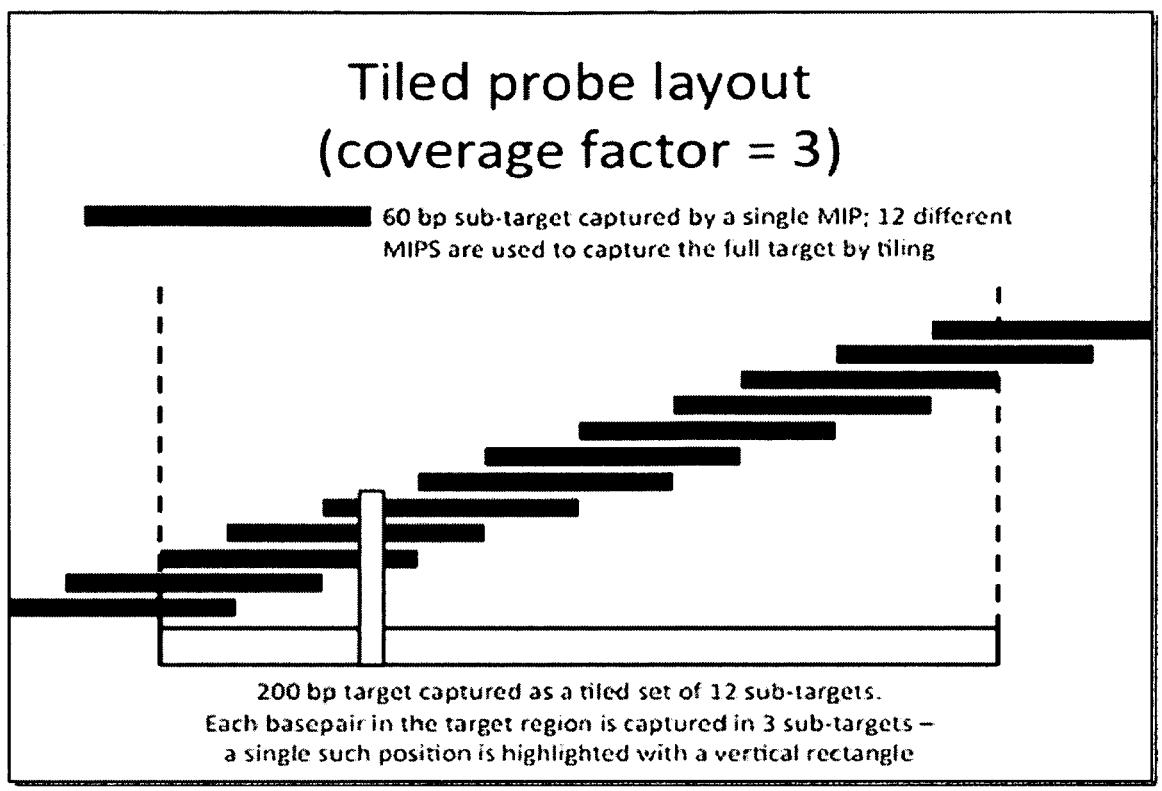
FIG. 1 illustrates a non-limiting embodiment of a tiled probe layout.

Aspects of the invention relate to preparative and analytical methods and compositions for evaluating genotypes, and in particular, for determining the allelic identity (or identities in a diploid organism) of one or more genetic loci in a subject.

Aspects of the invention are based, in part, on the identification of different sources of ambiguity and error in genetic analyses, and, in part, on the identification of one or more approaches to avoid, reduce, recognize, and/or resolve these errors and ambiguities at different stages in a genetic analysis. Aspects of the invention relate to methods and compositions for addressing bias and/or stochastic variation associated with one or more preparative and/or analytical steps of a nucleic acid evaluation technology. In some embodiments, preparative methods can be adapted to avoid or reduce the risk of bias skewing the results of a genetic analysis. In some embodiments, analytical methods can be adapted to recognize and correct for data variations that may give rise to misinterpretation (e.g., incorrect calls such as homozygous when the subject is actually heterozygous or heterozygous when the subject is actually homozygous). Methods of the invention may be used for any type of mutation, for example a single base change (e.g., insertion, deletion, transversion or transition, etc.), a multiple base insertion, deletion, duplication, inversion, and/or any other change or combination thereof.

In some embodiments, additional or alternative techniques may be used to address loci characterized by multiple repeats of a core sequence where the length of the repeat is longer than a typical sequencing read thereby making it difficult to determine whether a deletion or duplication of one or more core sequence units has occurred based solely on a sequence read.

In some embodiments, increased confidence in an assay result may be obtained by i) selecting two or more different preparative and/or analytical techniques that have different biases (e.g., known to have different biases), ii) evaluating a patient sample using the two or more different techniques, iii) comparing the results from the two or more different techniques, and/or iv) determining whether the results are consistent for the two or more different techniques. In some embodiments, if determining in step (iv) indicates that the results are consistent (e.g., the same) then increased confidence in the assay result is obtained. In other embodiments, if determining in step (iv) indicates that the results are inconsistent (e.g., that the results are ambiguous) then one or more additional preparative and/or analytical techniques, which have a different bias (e.g., known to have a different bias) compared with the two or more different preparative and/or analytical techniques selected in step (i), are used to evaluate the patient sample, and the results of the one or more additional preparative and/or analytical techniques are compared with the results from step (ii) to resolve the inconsistency.

In some embodiments, two or more independent samples may be obtained from a subject and independently analyzed. In some embodiments, two or more independent samples are obtained at approximately the same time point. In some embodiments, two or more independent samples are obtained at multiple different time points. In some embodiments, the use of two or more independent sample facilitates the elimination, normalization, and/or quantification of stochastic measurement noise. It is to be appreciated that two or more independent samples may be obtained in connection with any of the methods disclosed herein, including, for example, methods for pathogen profiling in a human or other animal subjects, monitoring tumor progression/regression, analyzing circulating tumor cells, analyzing fetal cells in maternal circulation, and analyzing/monitoring/profiling of environmental pathogens.

In some embodiments, one or more of the techniques described herein may be combined in a single assay protocol for evaluating multiple patient samples in parallel.

It should be appreciated that aspects of the invention may be useful for high throughput, cost-effective, yet reliable, genotyping of multiple patient samples (e.g., in parallel, for example in multiplex reactions). In some embodiments, aspects of the invention are useful to reduce the error frequency in a multiplex analysis. Certain embodiments may be particularly useful where multiple reactions (e.g., multiple loci and/or multiple patient samples) are being processed. For example, 10-25, 25-50, 50-75, 75-100 or more loci may be evaluated for each subject out of any number of subject samples that may be processed in parallel (e.g., 1-25, 25-50, 50-100, 100-500, 500-1,000, 1,000-2,500, 2,500-5,000 or more or intermediate numbers of patient samples). It should be appreciated that different embodiments of the invention may involve conducting two or more target capture reactions and/or two or more patient sample analyses in parallel in a single multiplex reaction. For example, in some embodiments a plurality of capture reactions (e.g., using different capture probes for different target loci) may be performed in a single multiplex reaction on a single patient sample. In some embodiments, a plurality of captured nucleic acids from each one of a plurality of patient samples may be combined in a single multiplex analysis reaction. In some embodiments, samples from different subjects are tagged with subject-specific (e.g., patient-specific) tags (e.g., unique sequence tags) so that the information from each product can be assigned to an identified subject. In some embodiments, each of the different capture probes used for each patient sample have a common patient-specific tag. In some embodiments, the capture probes do not have patient-specific tags, but the captured products from each subject may be amplified using one or a pair of amplification primers that are labeled with a patient-specific tag. Other techniques for associating a patient-specific tag with the captured product from a single patient sample may be used as aspects of the invention are not limited in this respect. It should be appreciated that patient-specific tags as used herein may refer to unique tags that are assigned to identified patients in a particular assay. The same tags may be used in a separate multiplex analysis with a different set of patient samples (e.g., from different patients) each of which is assigned one of the tags. In some embodiments, different sets of unique tags may be used in sequential (e.g., alternating) multiplex reactions in order to reduce the risk of contamination from one assay to the next and allow contamination to be detected on the basis of the presence of tags that are not expected to be present in a particular assay.

Embodiments of the invention may be used for any of a number of different settings: reproductive settings, disease screening, identifying subjects having cancer, identifying subjects having increased risk for a disease, stratifying a population of subjects according to one or more of a number of factors, for example responsiveness to a particular drug, lack or not of an adverse reaction (or risk therefore) to a particular drug, and/or providing information for medical records (e.g., homozygosity, heterozygosity at one or more loci). It should be appreciated that the invention is not limited to genomic analysis of patient samples. For example, aspects of the invention may be useful for high throughput genetic analysis of environment samples to detect pathogens.

In some embodiments, the methods disclosed herein are useful for diagnosis of one or more heritable disorders. In some embodiments, a heritable disorder that may be diagnosed with the methods disclosed herein is a genetic disorder that is prevalent in the Ashkenazi Jewish population. In some embodiments, the heritable disorders are selected from: 21-Hydroxylase-Defiocient Congenital Adrenal Hyperplasia; ABCC8-Related Hyperinsulinism; Alpha-Thalassemia, includes Constant Spring, & MR associated; Arylsulfatase A Deficiency-Metyachromatic Leukodystrophy; Biotinidase Deficiency Holocarboxylase Synthetase Deficiency; Bloom's Syndrome; Canavan Disease; CFTR-Related Disorders-cystic fibrosis; Citrullinemia Type 1; Combined MMA & Homocystinuria-db1C; Dystrophinopathies (DMD & BMD); Familial Dysautonomia; Fanconi Anemia-FANCC; Galactosemia-Classical: Galactokinase Defiency & Galactose Epimerase Deficiency; Gaucher Disease; GJB2-Related DFNB 1 Nonsyndromic Hearing Loss and Deafness; Glutaric acidemia Type 1; Hemoglobinopathies beta-chain disorders; Glycogen Storage Disease Type 1A; Maple Syrup Urine Disease; Types 1A, 1B, 2, 3; Medium Chain Acyl-Coenzyme A; Dehydrogenase Deficiency-MCADD; Methylmalonic Acidemia; Mucolipidosis IV; Nemaline Myopathy; Nieman-Pick Type A-Acid Sphingomyelinase Deficiency; Non-Ketotic Hyperglycinemia-Glycine Encephalopathy; Ornithine Transcarbamylase Deficiency; PKU Phenylalanine Hydroxylase Deficiency; Propionic Acidemia; Short Chain Acyl-CoA Dehydrogenase Deficiency-SCADD; Smith-Lemli-Opitz Syndrome; Spinal Muscular Atrophy (SMNI)-SMA; Tay Sachs-HexA Deficiency; Usher Synbdrome-Type I (Type IB, Type IC, Type ID, Type IF, Type IG); X-Linked Mental Retardation ARX-Related Disorders; X-Linked Mental Retardation with Cerebellar Cypoplasia and sistinctive Facial Appearance; X-Linked Mental Retardation; includes 9, 21, 30, 46, 58, 63, 88, 89; X linked mental retardation: FM1-Related Disorders—FRXA, Fragile X MR; X-linked SMR: Renpenning Syndrome 1; Zellweger Spectrum disorders—Peroxisomal Bifunctional Enzyme Deficiencies including Zellweger, NALD, and/or infantile Refsums. However, all of these, subsets of these, other genes, or combinations thereof may be used.

According to some aspects, the disclosure relates to multiplex diagnostic methods. In some embodiments, multiplex diagnostic methods comprise capturing a plurality of genetic loci in parallel (e.g., a genetic locus of Table 1). In some embodiments, genetic loci possess one or more polymorphisms (e.g., a polymorphism of Table 2) the genotypes of which correspond to disease causing alleles. Accordingly, in some embodiments, the disclosure provides methods for assessing multiple heritable disorders in parallel.

In some embodiments, methods are provided for diagnosing multiple heritable disorders in parallel at a pre-implantation, prenatal, perinatal, or postnatal stage. In some embodiments, the disclosure provides methods for analyzing multiple genetic loci (e.g., a plurality of target nucleic acids selected from Table 1) from a patient sample, such as a blood, pre-implantation embryo, chorionic villus or amniotic fluid sample. A patient or subject may be a human. However, aspects of the invention are not limited to humans and may be applied to other species (e.g., mammals, birds, reptiles, other vertebrates or invertebrates) as aspects of the invention are not limited in this respect. A subject or patient may be male or female. In some embodiments, in connection with reproductive genetic counseling, samples from a male and female member of a couple may be analyzed. In some embodiments, for example, in connection with an animal breeding program, samples from a plurality of male and female subjects may be analyzed to determine compatible or optimal breeding partners or strategies for particular traits or to avoid one or more diseases or conditions.

However, it should be appreciated that any other diseases may be studied and/or risk factors for diseases or disorders including, but not limited to allergies, responsiveness to treatment, cancer tumor profiling for treatment and prognosis, monitoring and identification of patient infections, and monitoring of environmental pathogens.

1. Reducing Representational Bias in Multiplex Amplification Reactions:

In some embodiments, aspects of the invention relate to methods that reduce bias and increase reproducibility in multiplex detection of genetic loci, e.g., for diagnostic purposes.

Molecular inversion probe technology is used to detect or amplify particular nucleic acid sequences in potentially complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes. However, challenges associated with, for example, amplification efficiency (See, e.g., Turner E H, et al., Nat Methods. 2009 Apr. 6:1-2.) have limited the practical utility of the method in research and diagnostic settings.

Aspects of the disclosure are based, in part, on the discovery of effective methods for overcoming challenges associated with systematic errors (bias) in multiplex genomic capture and sequencing methods, namely high variability in target nucleic acid representation and unequal sampling of heterozygous alleles in pools of captured target nucleic acids (e.g., isolated from a biological sample). Accordingly, in some embodiments, the disclosure provides methods that reduce variability in the detection of target nucleic acids in multiplex capture methods. In other embodiments, methods improve allelic representation in a capture pool and, thus, improve variant detection outcomes. In certain embodiments, the disclosure provides preparative methods for capturing target nucleic acids (e.g., genetic loci) that involve the use of different sets of multiple probes (e.g., molecular inversion probes MIPs) that capture overlapping regions of a target nucleic acid to achieve a more uniform representation of the target nucleic acids in a capture pool compared with methods of the prior art. In other embodiments, methods reduce bias, or the risk of bias, associated with large scale parallel capture of genetic loci, e.g., for diagnostic purposes. In other embodiments, methods are provided for increasing reproducibility (e.g., by reducing the effect of polymorphisms on target nucleic acid capture) in the detection of a plurality of genetic loci in parallel. In further embodiments, methods are provided for reducing the effect of probe synthesis and/or probe amplification variability on the analysis of a plurality of genetic loci in parallel.

In some aspects, the disclosure provides probe sets that comprise a plurality of different probes. As used herein, a 'probe' is a nucleic acid having a central region flanked by a 5' region and a 3' region that are complementary to nucleic acids flanking the same strand of a target nucleic acid or subregion thereof. An exemplary probe is a molecular inversion probe (MIP). A 'target nucleic acid' may be a genetic locus.

Exemplary genetic loci are disclosed herein in Table 1 (RefSeqGene Column).

While probes have been typically designed to meet certain constraints (e.g. melting temperature, G/C content, etc.) known to partially affect capture/amplification efficiency (Ball et al (2009) Nat Biotech 27:361-8 AND Deng et al (2009) Nat Biotech 27:353-60), a set of constraints which is sufficient to ensure either largely uniform or highly reproducible capture/amplification efficiency has not previously been achieved.

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a bp refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids are too large to be captured with one probe. Consequently, it may be necessary to capture multiple subregions of a target nucleic acid in order to analyze the full target.

In some embodiments, a subregion of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid).

In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Aspects of the invention involve using multiple probes, e.g., MIPs, to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted ('dialed in') by changing the number of different MIPs used to capture a given molecule.

In some embodiments, the 'coverage factor', or number of probes used to capture a basepair in a molecule, is an important parameter to specify. Different numbers of probes per target are indicated depending on whether one is using the tiling approach (see, e.g., FIG. 1) or one of the staggered approaches (see, e.g., FIG. 2 or 3).

FIG. 1 illustrates a non-limiting embodiment of a tiled probe layout showing ten captured sub-targets tiled across a single target. Each position in the target is covered by three sub-targets such that MIP performance per base pair is averaged across three probes.

Figure 2:
FIG. 2 illustrates a non-limiting embodiment of a staggered probe layout.

FIG. 2 illustrates a non-limiting embodiment of a staggered probe layout showing the targets captured by a set of three MIPs. Each MIP captures the full target, shown in black, plus (in some cases) additional extra-target sequence, shown in gray, such that the targeting arms of each MIP fall on different sequence. Each position in the target is covered by three sub-targets such that MIP performance per basepair is averaged across three probes. Targeting arms land immediately adjacent to the black or gray regions shown. It should be appreciated that in some embodiments, the targeting arms (not shown) can be designed so that they do not overlap with each other.

Figure 3:
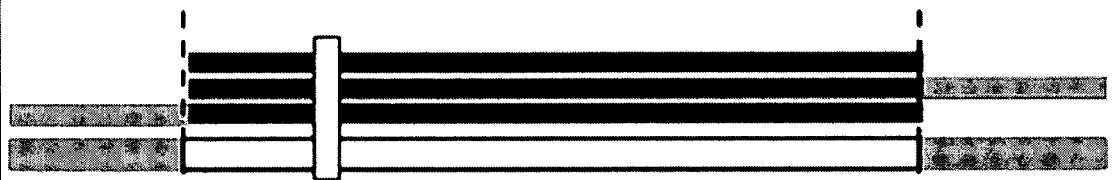
FIG. 3 illustrates a non-limiting embodiment of an alternating staggered probe layout.

FIG. 3 illustrates a non-limiting embodiment of an alternating staggered probe layout showing the targets captured by a set of three MIPs. Each MIP captures the full target, shown in black, plus (in some cases) additional extra-target sequence, shown in gray, such that the targeting arms of each MIP fall on different sequence. Each position in the target is covered by three sub-targets such that MIP performance per basepair is averaged across three probes. Targeting arms land immediately adjacent to the black or gray regions shown.

It should be appreciated that for any of the layouts, the targeting arms on adjacent tiled or staggered probes may be designed to either overlap, not overlap, or overlap for only a subset of the probes.

In certain embodiments for any of the layouts, a coverage factor of about 3 to about 10 is used. However, the methods are not so limited and coverage factors of up to 2, 3, 4, 5, 6, 7, 8, 9, 10, 20 or more may be used. It is to be appreciated that the coverage factor selected may depend the probe layout being employed. For example, in the tiling approach, for a desired coverage factor, the number of probes per target is typically a function of target length, sub-target length, and spacing between adjacent sub-target start locations (step size). For example, for a desired coverage factor of 3, a 200 bp target with a start-site separation of 20 bp and sub-target length of 60 bp may be encompassed with 12 MIPs (FIG. 1). Thus, a specific coverage factor may be achieved by varying the number of probes per target nucleic acid and the length of the molecules captured. In the staggered approach, a fixed-length target nucleic acid is captured as several subregions or as 'super-targets', which are molecules comprising the target nucleic acid and additional flanking nucleic acids, which may be of varying lengths. For example, a target of 50 bp can be captured at a coverage factor of 3 with 3 probes in either a 'staggered' (FIG. 2) or 'alternating staggered' configuration (FIG. 3).

The coverage factor will be driven by the extent to which detection bias is tolerable. In some cases, where the bias tolerance is small, it may be desirable to target more subregions of target nucleic acid with, perhaps, higher coverage factors. In some embodiments, the coverage factor is up to 2, 3, 4, 5, 6, 7, 8, 9, 10 or more.

In some embodiments, when a tiled probe layout is used, when the target length is greater than 1 bp and when a step size (distance between the 5'-end of a target and the 5' end of its adjacent target) is less than the length of a target or subregion thereof, it is possible to compute probe number for a particular target based on target length (T), sub target length (S), and coverage factor (C), such that probe number=T/(S/C)+(C−1).

In some aspects, the disclosure provides methods to increase the uniformity of amplification efficiency when multiple molecules are amplified in parallel; methods to increase the reproducibility of amplification efficiency; methods to reduce the contribution of targeting probe variability to amplification efficiency; methods to reduce the effect on a given target nucleic acid of polymorphisms in probe hybridization regions; and/or methods to simplify downstream workflows when multiplex amplification by MIPs is used as a preparative step for analysis by nucleic acid sequencing.

Polymorphisms in the target nucleic acid under the regions flanking a target can interfere with hybridization, polymerase fill-in, and/or ligation. Furthermore, this may occur for only one allele, resulting in allelic drop-out, which ultimately decreases downstream sequencing accuracy. In some embodiments, using a set of MIPs having multiple hybridization sites for the capture of any given target, the probability of loss from polymorphism is substantially decreased because not all targeting arms in the set of MIPs will cover the location of the mutation.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Multiplex amplification strategies disclosed herein may be used analytically, as in detection of SNPs, or preparatively, often for next-generation sequencing or other sequencing techniques. In the preparative setting, the output of an amplification reaction is generally the input to a shotgun library protocol, which then becomes the input to the sequencing platform. The shotgun library is necessary in part because next-generation sequencing yields reads significantly shorter than amplicons such as exons. In addition to the bias-reduction afforded by the multi-tiled approach described here, tiling also obviates the need for shotgun library preparation. Since the length of the capture molecule can be specified when the probes, e.g., MIPs, are designed, it can be chosen to match the readlength of the sequencer. In this way, reads can 'walk' across an exon by virtue of the start position of each capture molecule in the probe set for that exon. Reducing analytical errors associated with bias in nucleic acid preparations: In some embodiments, aspects of the invention relate to preparative steps in DNA sequencing-related technologies that reduce bias and increase the reliability and accuracy of downstream quantitative applications.

There are currently many genomics assays that utilize next-generation (polony-based) sequencing to generate data, including genome resequencing, RNA-seq for gene expression, bisulphite sequencing for methylation, and Immune-seq, among others. In order to make quantitative measurements (including genotype calling), these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. This may include chemical or biochemical treatment of the DNA (e.g., bisulphite treatment), capture of a specific subset of the genome (e.g., padlock probe capture, solution hybridization), and a variety of amplification techniques (e.g., polymerase chain reaction, whole genome amplification, rolling circle amplification).

Systematic and random errors are common problems associated with genome amplification and sequencing library construction techniques. For example, genomic sequencing library may contain an over- or under-representation of particular sequences from a source genome as a result of errors (bias) in the library construction process. Such bias can be particularly problematic when it results in target sequences from a genome being absent or undetectable in the sequencing libraries. For example, an under representation of particular allelic sequences (e.g., heterozygotic alleles) from a genome in a sequencing library can result in an apparent homozygous representation in a sequencing library. As most downstream sequencing library quantification techniques depend on stochastic counting processes, these problems have typically been addressed by sampling enough (over-sampling) to obtain a minimum number of observations necessary to make statistically significant decisions. However, the strategy of oversampling is generally limited to elimination of low-count Poisson noise, and the approach wastes resources and increases the expense required to perform such experiments. Moreover, oversampling can result in a reduced statistical confidence in certain conclusions (e.g., diagnostic calls) based on the data. Accordingly, new approaches are needed for overcoming bias in sequencing library preparatory methods.

Aspects of the disclosure are based, in part, on the discovery of methods for overcoming problems associated with systematic and random errors (bias) in genome capture, amplification and sequencing methods, namely high variability in the capture and amplification of nucleic acids and disproportionate representation of heterozygous alleles in sequencing libraries. Accordingly, in some embodiments, the disclosure provides methods that reduce variability in the capture and amplification of nucleic acids. In other embodiments, the methods improve allelic representation in sequencing libraries and, thus, improve variant detection outcomes. In certain embodiments, the disclosure provides preparative methods for capturing target nucleic acids (e.g., genetic loci) that involve the use of differentiator tag sequences to uniquely tag individual nucleic acid molecules. In some embodiments, the differentiator tag sequence permits the detection of bias based on the frequency with which pairs of differentiator tag and target sequences are observed in a sequencing reaction. In other embodiments, the methods reduce errors caused by bias, or the risk of bias, associated with the capture, amplification and sequencing of genetic loci, e.g., for diagnostic purposes.

Aspects of the invention relate to associating unique sequence tags (referred to as differentiator tag sequences) with individual target molecules that are independently captured and/or analyzed (e.g., prior to amplification or other process that may introduce bias). These tags are useful to distinguish independent target molecules from each other thereby allowing an analysis to be based on a known number of individual target molecules. For example, if each of a plurality of target molecule sequences obtained in an assay is associated with a different differentiator tag, then the target sequences can be considered to be independent of each other and a genotype likelihood can be determined based on this information. In contrast, if each of the plurality of target molecule sequences obtained in the assay is associated with the same differentiator tag, then they probably all originated from the same target molecule due to over-representation (e.g., due to biased amplification) of this target molecule in the assay. This provides less information than the situation where each nucleic acid was associated with a different differentiator tag. In some embodiments, a threshold number of independently isolated molecules (e.g., unique combinations of differentiator tag and target sequences) is analyzed to determine the genotype of a subject.

Figure 4A:
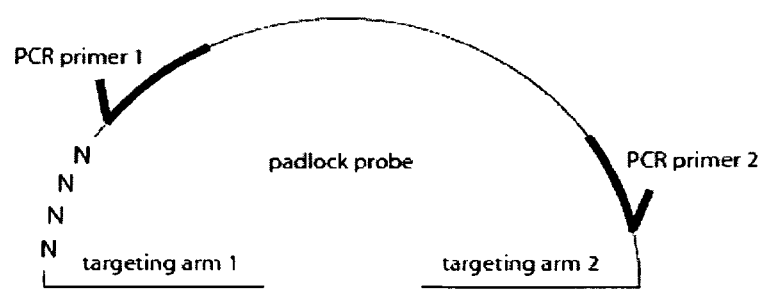
FIGS. 4A-C depict various non-limiting methods for combining differentiator tag sequence and target sequences (NNNN depicts a differentiator tag sequence)
Figure 4B:
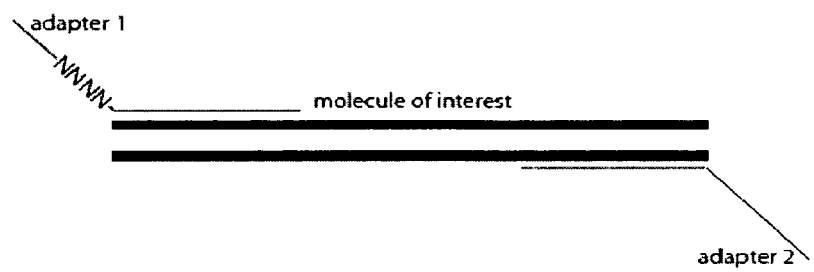
Figure 4C:
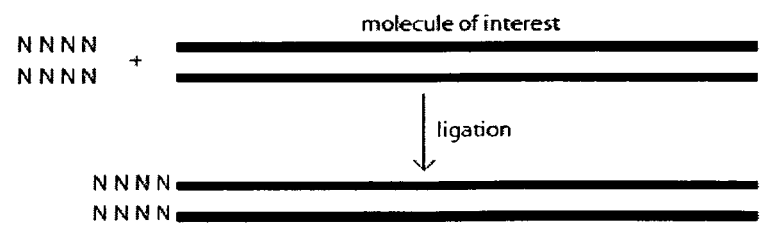

In some embodiments, the invention relates to compositions comprising pools (libraries) of preparative nucleic acids that each comprise "differentiator tag sequences" for detecting and reducing the effects of bias, and for genotyping target nucleic acid sequences. As used herein, a "differentiator tag sequence" is a sequence of a nucleic acid (a preparative nucleic acid), which in the context of a plurality of different isolated nucleic acids, identifies a unique, independently isolated nucleic acid. Typically, differentiator tag sequences are used to identify the origin of a target nucleic acid at one or more stages of a nucleic acid preparative method. For example, in the context of a multiplex nucleic acid capture reaction, differentiator tag sequences provide a basis for differentiating between multiple independent, target nucleic acid capture events. Also, in the context of a multiplex nucleic acid amplification reaction, differentiator tag sequences provide a basis for differentiating between multiple independent, primary amplicons of a target nucleic acid, for example. Thus, combinations of target nucleic acid and differentiator tag sequence (target:differentiator tag sequences) of an isolated nucleic acid of a preparative method provide a basis for identifying unique, independently isolated target nucleic acids. FIG. 4A-C depict various non-limiting examples of methods for combining differentiator tag sequence and target sequences.

It will be apparent to the skilled artisan that differentiator tags may be synthesized using any one of a number of different methods known in the art. For example, differentiator tags may be synthesized by random nucleotide addition.

Differentiator tag sequences are typically of a predefined length, which is selected to control the likelihood of producing unique target:differentiator tag sequences in a preparative reaction (e.g., amplification-based reaction, a circularization selection-based reaction, e.g., a MIP reaction). Differentiator tag sequences may be, up to 5, up to 6, up to 7 up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, or more nucleotides in length. For purposes of genotyping, isolated nucleic acids are identified as independently isolated if they comprise unique combinations of target nucleic acid and differentiator tag sequences, and observance of threshold numbers of unique combinations of target nucleic acid and differentiator tag sequences provide a certain statistical confidence in the genotype.

During a library preparation process, each nucleic acid molecule may be tagged with a unique differentiator tag sequence in a configuration that permits the differentiator tag sequence to be sequenced along with the target nucleic acid sequence of interest (the nucleic acid sequence for which the library is being prepared, e.g., a polymorphic sequence). The incorporation of the nucleic acid comprising a differentiator tag sequence at a particular step allows the detection and correction of biases in subsequent steps of the protocol.

A large library of unique differentiator tag sequences may be created by using degenerate, random-sequence polynucleotides of defined length. The differentiator tag sequences of the polynucleotides may be read at the final stage of the sequencing. The observations of the differentiator tag sequences may be used to detect and correct biases in the final sequencing read-out of the library. For example, the total possible number of differentiator tag sequences, which may be produced, e.g., randomly, is 4N, where N is the length of the differentiator tag sequence. Thus, it is to be understood that the length of the differentiator tag sequence may be adjusted such that the size of the population of MIPs having unique differentiator tag sequences is sufficient to produce a library of MIP capture products in which identical independent combinations of target nucleic acid and differentiator tag sequence are rare. As used herein combinations of target nucleic acid and differentiator tag sequences, may also be referred to as "target:differentiator tag sequences".

In the final readout of a sequencing process, each read may have an additional unique differentiator tag sequence. In some embodiments, when differentiator tag sequences are distributed randomly in a library, all the unique differentiator tag sequences will be observed about an equal number of times. Accordingly, the number of occurrences of a differentiator tag sequence may follow a Poisson distribution.

In some embodiments, overrepresentation of target:differentiator tag sequences in a pool of preparative nucleic acids (e.g., amplified MIP capture products) is indicative of bias in the preparative process (e.g., bias in the amplification process). For example, target:differentiator tag sequence combinations that are statistically overrepresented are indicative of bias in the protocol at one or more steps between the incorporation of the differentiator tag sequences into MIPs and the actual sequencing of the MIP capture products.

The number of reads of a given target:differentiator tag sequence may be indicative (may serve as a proxy) of the amount of that target sequence present in the originating sample. In some embodiments, the numbers of occurrence of sequences in the originating sample is the quantity of interest. For example, using the methods disclosed herein, the occurrence of differentiator tag sequences in a pool of MIPs may be predetermined (e.g., may be the same for all differentiator tag sequences). Accordingly, changes in the occurrence of differentiator tag sequences after amplification and sequencing may be indicative of bias in the protocol. Bias may be corrected to provide an accurate representation of the composition of the original MIP pool, e.g., for diagnostic purposes.

According to some aspects, a library of preparative nucleic acid molecules (e.g., MIPs, each nucleic acid in the library having a unique differentiator tag sequence, may be constructed such that the number of nucleic acid molecules in the library is significantly larger than the number prospective target nucleic acid molecules to be captured using the library. This ensures that products of the preparative methods include only unique target:differentiator tag sequence; e.g., in a MIP reaction the capture step would undersample the total population of unique differentiator tag sequences in the MIP library. For example, an experiment utilizing 1 ug of genomic DNA will contain about ~150,000 copies of a diploid genome. For a MIP library, each MIP in the library comprising a randomly produced 12-mer differentiator tag sequence (~1.6 million possible unique differentiator tag sequences), there would be more than 100 unique differentiator tag sequences per genomic copy. For a MIP library, each MIP in the library comprising a randomly produced 15-mer differentiator tag sequence (~1 billion possible unique differentiator tag sequences), there would be more than 7000 unique differentiator tag sequences per genomic copy. Therefore, the probability of the same differentiator tag sequence being incorporated multiple times is incredibly small. Thus, it is to be appreciated that the length of the differentiator tag sequence is to be selected based on the amount of target sequence in a MIP capture reaction and the desired probability for having multiple, independent occurrences of target:differentiator tag sequence combinations.

Figure 5:
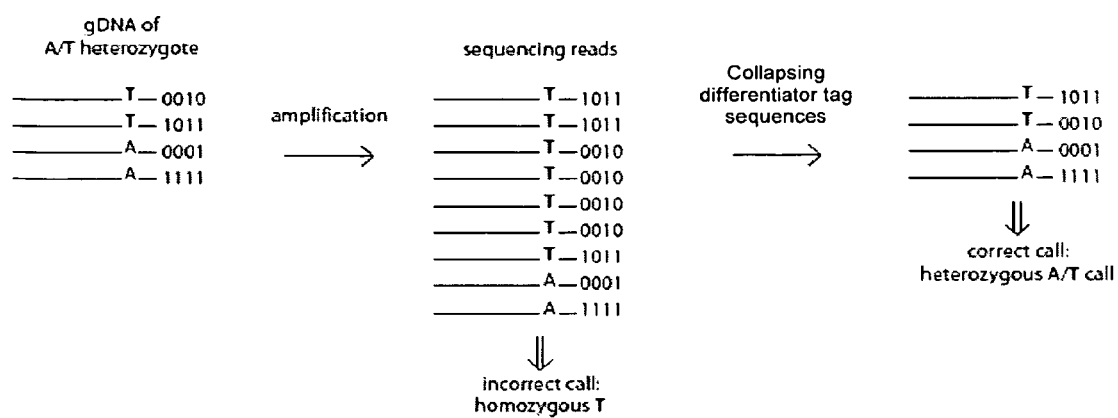
FIG. 5 depicts a non-limiting method for genotyping based on target and 5 differentiator tag sequences.
Figure 6:
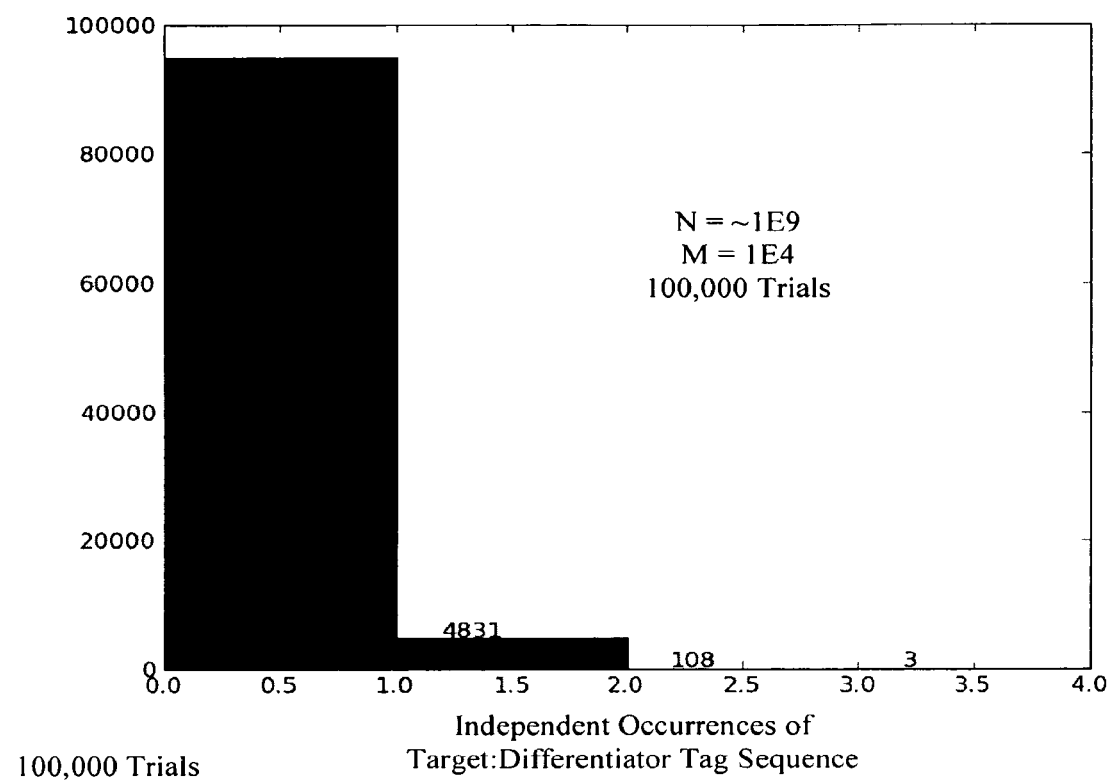
FIG. 6 depicts non-limiting results of a simulation of a MIP capture reaction.
Figure 7:
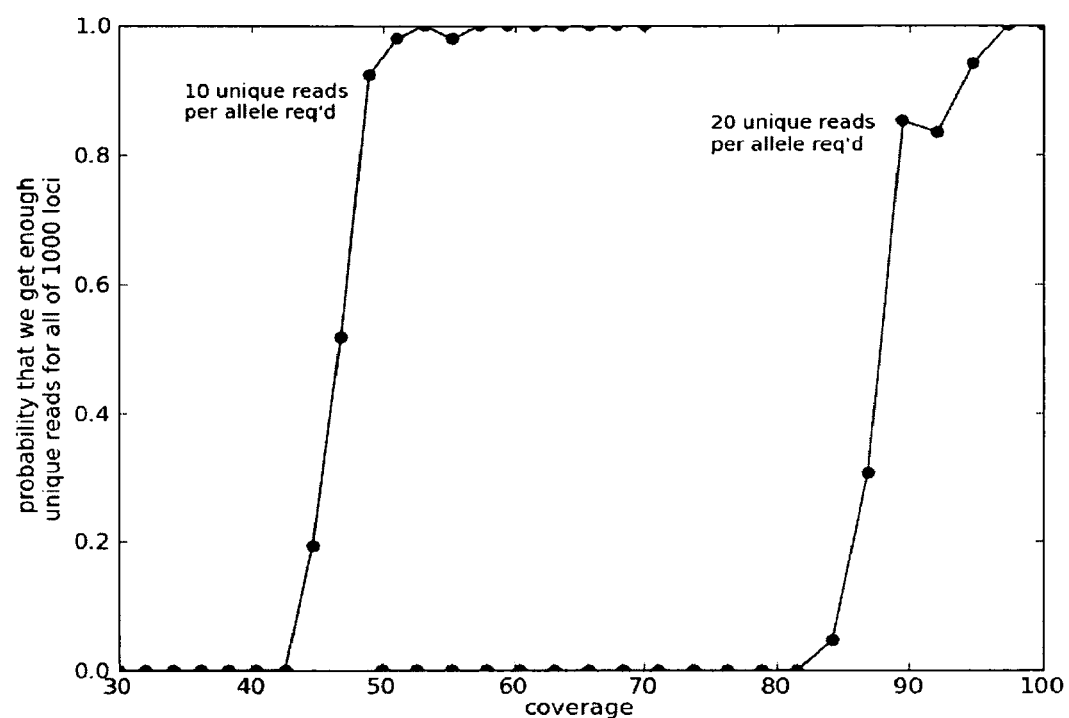
FIG. 7 depicts a non-limiting graph of sequencing coverage.

FIG. 5 depicts a non-limiting method for genotyping based on target and differentiator tag sequences. Sequencing reads of target and differentiator tags sequences are collapsed to make diploid genotype calls. FIG. 6 depicts non-limiting results of a simulation of a MIP capture reaction in which MIP probes, each having a differentiator tag sequence of 15 nucleotides, are combined with 10000 target sequence copies (e.g., genome equivalents). In this simulated reaction, the probability of capturing one or more copies of a target sequence having the same differentiator tag sequence is 0.05. The Y axis reflects the number of observations. The X axis reflects the number of independent occurrences of target:differentiator tag combinations. FIG. 7 depicts a non-limiting graph of sequencing coverage, which can help ensure that alleles are sampled to sufficient depth (e.g., either 10× or 20× minimum sampling per allele, assuming 1000 targets). In this non-limiting example, the X axis is total per-target coverage required, and the Y axis is the probability that a given total coverage will result in at least 10× or 20× coverage for each allele.

The skilled artisan will appreciate that as part of a MIP library preparation process, adapters may be ligated onto the ends of the molecules of interest. Adapters often contain PCR primer sites (for amplification or emulsion PCR) and/or sequencing primer sites. In addition, barcodes may be included, for example, to uniquely identify individual samples (e.g., patient samples) that may be mixed together. (See, e.g., USPTO Publication Number US 2007/0020640 A1 (McCloskey et al.)

The actual incorporation of the random differentiator tag sequences can be performed through various methods known in the art. For example, nucleic acids comprising differentiator tag sequences may be incorporated by ligation. This is a flexible method, because molecules having differentiator tag sequence can be ligated to any blunt-ended nucleic acids. The sequencing primers must be incorporated subsequently such that they sequence both the differentiator tag sequence and the target sequence. Alternatively, the sequencing adaptors can be synthesized with the random differentiator tag sequences at their 3' end (as degenerate bases), so that only one ligation must be performed. Another method is to incorporate the differentiator tag sequence into a PCR primer, such that the primer structure is arranged with the common adaptor sequence followed by the random differentiator tag sequence followed by the PCR priming sequence (in 5' to 3' order). A differentiator tag sequence and adaptor sequence (which may contain the sequencing primer site) are incorporated as tags. Another method to incorporate the differentiator tag sequences is to synthesize them into a padlock probe prior to performing a gene capture reaction. The differentiator tag sequence is incorporated 3' to the targeting arm but 5' to the amplification primer that will be used downstream in the protocol. Another method to incorporate the differentiator tag sequences is as a tag on a gene-specific or poly-dT reverse-transcription primer. This allows the differentiator tag sequence to be incorporated directly at the cDNA level.

In some embodiments, at the incorporation step, the distribution of differentiator tag sequences can be assumed to be uniform. In this case, bias in any part of the protocol would change the uniformity of this distribution, which can be observed after sequencing. This allows the differentiator tag sequence to be used in any preparative process where the ultimate output is sequencing of many molecules in parallel.

Differentiator tag sequences may be incorporated into probes (e.g., MIPs) of a plurality when they are synthesized on-chip in parallel, such that degeneracy of the incorporated nucleotides is sufficient to ensure near-uniform distribution in the plurality of probes. It is to be appreciated that amplification of a pool of unique differentiator tag sequences may itself introduce bias in the initial pool. However, in most practical cases, the scale of synthesis (e.g., by column synthesis, chip based synthesis, etc.) is large enough that amplification of an initial pool of differentiator tag sequences is not necessary. By avoiding amplification or selection steps on the pool of unique differentiator tag sequences, potential bias may be minimized. One example of the use of the differentiator tag sequences is in genome re-sequencing.

Considering that the raw accuracy of most next-generation sequencing instruments is relatively low, it is crucial to oversample the genomic loci of interest.

Furthermore, since there are two alleles at every locus, it is important to sample enough to ensure that both alleles have been observed a sufficient number of times to determine with a sufficient degree of statistical confidence whether the sample is homozygous or heterozygous. Indeed, the sequencing is performed to sample the composition of molecules in the originating sample. However, after multiple reads have been collected for a given locus, it is possible that due to bias (e.g., caused by PCR amplification steps), a large fraction of the reads are derived from a single originating molecule. This would skew the population of target sequences observed, and would affect the outcome of the genotype call. For example, it is possible that a locus that is heterozygous is called as homozygous, because there are only a few observations of the second allele out of many observations of that locus. However, if information is available on differentiator tag sequences, this situation could be averted, because the over-represented allele would be seen to also have an over-represented differentiator tag sequence (i.e., the sequences with the overrepresented differentiator tag sequence all originated from the same single molecule). Therefore, the sequences and corresponding distribution of differentiator tag sequences can be used as an additional input to the genotype-calling algorithm to significantly improve the accuracy and confidence of the genotype calls.

In some aspects, the disclosure provides methods for analyzing a plurality of target sequences which are genetic loci or portions of genetic loci (e.g., a genetic locus of Table 1). The genetic loci may be analyzed by sequencing to obtain a genotype at one or more polymorphisms (e.g., SNPs). Exemplary polymorphisms are disclosed in Table 2. The skilled artisan will appreciate that other polymorphisms are known in the art and may be identified, for example, by querying the Entrez Single Nucleotide Polymorphism database, for example, by searching with a GeneID from Table 1.

TABLE 1

Target Nucleic Acids

| Gene name | Gene ID | Description | Gene aliases | OMIM | RefSeqGene | Chromosome map position |
|---|---|---|---|---|---|---|
| CYP21 A2 | 1589 | cytochrome P450, family 21, subfamily A, polypeptide 2 | CAH1; CPS1; CA21H; CYP21; CYP21B; P450c21B; MGC150536; MGC150537; CYP21 A2 | 201910 | NG_008337,1 | 6p21.3 |
| ABCC8 | 6833 | ATP-binding cassette, sub-family C (CFTR/MRP), member 8 | HI; SUR; HHF1; MRP8; PHHI; SUR1; ABC36; HRINS; TNDM2; ABCC8 | 600509 | NG_008867.1 | 11p15.1 |

TABLE 1-continued

Target Nucleic Acids

| Gene name | Gene ID | Description | Gene aliases | OMIM | RefSeqGene | Chromosome map position |
|---|---|---|---|---|---|---|
| ATRX | 546 | alpha thalassemia/mental retardation syndrome X-linked (RAD54 homolog, *S. cerevisiae*) | SHS; XH2; XNP; ATR2; SFM1; RAD54; MRXHF1; RAD54L; ZNF-HX; MGC2094; ATRX | 300032 | NG_008838.1 | Xq13.1-q21.1 |
| ARSA | 410 | arylsulfatase A | MLD; ARSA | 607574 | NG_009260.1 | 22q13.31-qter; 22q13.33 |
| PSAP | 5660 | Prosaposin | GLBA; SAP1; FLJ00245; MGC110993; PSAP | 176801 | NG_008835.1 | 10q21-q22 |
| BTD | 686 | Biotinidase | BTD | 609019 | NG_008019.1 | 3p25 |
| HLCS | 3141 | holocarboxylase synthetase (biotin-(proprionyl-Coenzyme A-carboxylase (ATP-hydrolysing)) ligase) | HCS; HLCS | 609018 | NC_000021.7 | 21q22.1; 21q22.13 |
| BLM | 641 | Bloom syndrome, RecQ helicase-like | BS; RECQ2; RECQL2; RECQL3; MGC126616; MGC131618; MGC131620; BLM | 604610 | NG_007272.1 | 15q26.1 |
| ASPA | 443 | aspartoacylase (Canavan disease) | ASP; ACY2; ASPA | 608034 | NG_008399.1 | 17pter-P13 |
| CFTR | 1080 | cystic fibrosis transmembrane conductance regulator (ATP-binding cassette sub-family C, member 7) | CF; MRP7; ABC35; ABCC7; CFTR/MRP; TNR-CFTR; dJ760C5.1; CFTR | 602421 | NC_000007.12 | 7q31.2 |
| ASS1 | 445 | argininosuccinate synthetase 1 | ASS; CTLN1; ASS1 | 603470 | NG_011542.1 | 9q34.1 |
| MMACHC | 25974 | methylmalonic aciduria (cobalamin deficiency) cblC type, with homocystinuria | cblC; FLJ25671; DKFZp564I122; RP11-291L19.3; MMACWC | 609831 | NC_000001.9 | 1p34.1 |
| IKBKAP | 8518 | inhibitor of kappa light polypeptide gene enhancer in B-cells, kinase complex-associated protein | FD; DYS; ELP1; IKAP; IKI3; TOT1; FLJ12497; DKFZp781H1425; IKBKAP | 603722 | NG_008788.1 | 9q31 |
| FANCC | 2176 | Fanconi anemia, complementation group C | FA3; FAC; FACC; FLJ14675; FANCC | 227645 | NG_011707.1 | 9q22.3 |
| GALK1 | 2584 | galactokinase 1 | GK1; GALK; GALK1 | 604313 | NG_008079.1 | 17q24 |
| GALT | 2592 | galactose-1-phosphate uridylyltransferase | GALT | 606999 | NC_000009.10 | 9p13 |
| GALE | 2582 | UDP-galactose-4-epimerase | SDR1E1; FLJ95174; FLJ97302; GALE | 606953 | NG_007068.1 | 1p36-p35 |
| GBA | 2629 | glucosidase, beta; acid (includes glucosylceramidase) | GCB; GBA1; GLUC; GBA | 606463 | NG_009783.1 | 1q21 |
| GJB2 | 2706 | gap junction protein, beta 2, 26 kDa | HID; KID; PPK; CX26; DFNA3; DFNB1; NSRD1; DFNA3A; DFNB1A; GJB2 | 121011 | NG_008358.1 | 13q11-q12 |

TABLE 1-continued

Target Nucleic Acids

| Gene name | Gene ID | Description | Gene aliases | OMIM | RefSeqGene | Chromosome map position |
|---|---|---|---|---|---|---|
| GCDH | 2639 | glutaryl-Cocnzyme A dehydrogenase | GCD; ACAD5; GCDH | 608801 | NG_009292.1 | 19p13.2 |
| G6PC | 2538 | glucose-6-phosphatase, catalytic subunit | G6PT; GSD1; GSD1a; MGC163350; G6PC | 232200 | NG_011808.1 | 17q21 |
| HBB | 3043 | hemoglobin, beta | CD113t-C; beta-globin; HBB | 141900 | NG_000007.3 | 11p15.5 |
| BCKDHA | 593 | branched chain keto acid dehydrogenase E1, alpha polypeptide | MSU; MSUD1; OVD1A; BCKDE1A; FLJ45695; BCKDHA | 608348 | NC_000019.8 | 19q13.1-q13.2 |
| BCKDHB | 594 | branched chain keto acid dehydrogenase E1, beta polypeptide | E1B; FLJ17880; dJ279A18.1; BCKDHB | 248611 | NG_009775.1 | 6q13-q15 |
| DBT | 1629 | dihydrolipoamide branched chain transacylase E2 | E2; E2B; BCATE2; MGC9061; DBT | 248610 | NG_011852.1 | 1p31 |
| DLD | 1738 | dihydrolipoamide dehydrogenase | E3; LAD; DLDH; GCSL; PHE3; DLD | 238331 | NG_008045.1 | 7q31-q32 |
| ACADM | 34 | acyl-Coenzyme A dehydrogenase, C-4 to C-12 straight chain | MCAD; ACAD1; MCADH; FLJ18227; FLJ93013; FLJ99884; ACADM | 607008 | NG_007045.1 | 1p31 |
| MMAA | 166785 | methylmalonic aciduria (cobalamin deficiency) cblA type | cblA; MGC120010; MGC120011; MGC120012; MGC120013; MMAA | 607481 | NG_007536.1 | 4q31.22 |
| MMAB | 326625 | methylmalonic aciduria (cobalamin deficiency) cblB type | ATR; cblB; MGC20496; MMAB | 607568 | NG_007096.1 | 12q24 |
| MUT | 4594 | methylmalonyl Coenzyme A mutase | MCM; MUT | 609058 | NG_007100.1 | 6p12.3 |
| MCOLN1 | 57192 | mucolipin 1 | ML4; MLIV; MST080; TRPML1; MSTP080; TRP-ML1; TRPM-L1; MCOLN1 | 605248 | NC_000019.8 | 19p13.3-p13.2 |
| ACTA1 | 58 | actin, alpha 1, skeletal muscle | ACTA; ASMA; CFTD; MPFD; NEM1; NEM2; NEM3; CFTD1; CFTDM; ACTA1 | 102610 | NG_006672.1 | 1q42.13 |
| TPM3 | 7170 | tropomyosin 3 | TM3; TRK; NEM1; TM-5; TM30; TM30 nm; TPMsk3; hscp30; MGC3261; FLJ41118; MGC14582; MGC72094; OK/SW-cl.5; TPM3 | 191030 | NG_008621.1 | 1q21.2 |
| TNNT1 | 7138 | troponin T type 1 (skeletal, slow) | ANM; TNT; STNT; TNTS; FLJ98147; MGC104241; TNNT1 | 191041 | NG_011829.1 | 19q13.4 |
| NEB | 4703 | nebulin | NEM2; NEB177D; FLJ11505; FLJ36536; FLJ39568; FLJ39584; DKFZp686C1456; NEB | 161650 | NG_009382.1 | 2q22 |
| SMPD1 | 6609 | sphingomyelin phosphodiesterase 1, acid lysosomal | ASM; NPD; SMPD1 | 607608 | NG_011780.1 | 11p15.4-p15.1 |
| GLDC | 2731 | glycine dehydrogenase (decarboxylating) | GCE; NKH; GCSP; HYGN1; MGC138198; MGC138200; GLDC | 238300 | NC_000009.10 | 9p22 |

TABLE 1-continued

Target Nucleic Acids

| Gene name | Gene ID | Description | Gene aliases | OMIM | RefSeqGene | Chromosome map position |
|---|---|---|---|---|---|---|
| GCSH | 2653 | glycine cleavage system protein H (aminomethyl carrier) | GCE; NKH; GCSH | 238330 | NC_000016.8 | 16q23.2 |
| AMT | 275 | aminomethyltransferase | GCE; NKH; GCST; AMT | 238310 | NC_000003.10 | 3p21.2-p21.1 |
| OTC | 5009 | ornithine carbamoyltransferase | OCTD; MGC129967; MGC129968; MGC138856; OTC | 300461 | NG_008471.1 | Xp21.1 |
| PAH | 5053 | phenylalanine hydroxylase | PH; PKU; PKU1; PAH | 612349 | NG_008690.1 | 12q22-q24.2 |
| DHPR | 5860 | quinoid dihydropteridine reductase | DHPR; PKU2; SDR33C1; FLJ42391; QDPR | 612676 | NG_008763.1 | 4p15.31 |
| PTS | 5805 | 6-pyruvoyltetrahydropterin synthase | PTPS; FLJ97081; PTS | 261640 | NG_008743.1 | 11q22.3-q23.3 |
| PCCA | 5095 | propionyl Coenzyme A carboxylase, alpha polypeptide | PCCA | 232000 | NG_008768.1 | 13q32 |
| PCCB | 5096 | propionyl Coenzyme A carboxylase, beta polypeptide | DKFZp451E113; PCCB | 232050 | NG_008939.1 | 3q21-q22 |
| ACADS | 35 | acyl-Coenzyme A dehydrogenase, C-2 to C-3 short chain | SCAD; ACAD3; ACADS | 606885 | NG_007991.1 | 12q22-qter |
| DHCR7 | 1717 | 7-dehydrocholesterol reductase | SLOS; DHCR7 | 602858 | NC_000011.8 | 11q13.2-q13.5 |
| SMNT | 6606 | survival of motor neuron 1, telomeric | SMA; SMN; SMA1; SMA2; SMA3; SMA4; SMA@; SMNT; BCD541; T-BCD541; SMN1 | 600354 | NG_008691.1 | 5q13 |
| HEXA | 3073 | hexosaminidase A (alpha polypeptide) | TSD; MGC99608; HEXA | 606869 | NG_009017.1 | 15q23-q24 |
| MYO7A | 4647 | myosin VIIA | DFNB2; MYU7A; NSRD2; USH1B; DFNA11; MYOVIIA; MYO7A | 276903 | NG_009086.1 | 11q13.5 |
| USH1C | 10083 | Usher syndrome 1 C (autosomal recessive, severe) | PDZ73; AIE-75; DFNB18; PDZ-45; PDZ-73; NY-CO-37; NY-CO-38; ush1cpst; PDZ-73/NY-CO-38; USH1C | 605242 | NC_000011.8 | 11p15.1-p14 |
| CDH23 | 64072 | cadherin-like 23 | USH1D; DFNB12; FLJ00233; FLJ36499; KIAA1774; KIAA1812; MGC102761; DKFZp434P2350; CDH23 | 605516 | NG_008835.1 | 10q21-q22 |
| PCDH15 | 65217 | protocadherin 15 | USH1F; DFNB23; DKFZp667A1711; PCDH15 | 605514 | NG_009191.1 | 10q21.1 |
| SANS | 124590 | Usher syndrome 1G (autosomal recessive) | SANS; ANKS4A; FLJ33924; USH1G | 607696 | NG_007882.1 | 17q25.1 |

TABLE 1-continued

Target Nucleic Acids

| Gene name | Gene ID | Description | Gene aliases | OMIM | RefSeqGene | Chromosome map position |
|---|---|---|---|---|---|---|
| ARX | 170302 | aristaless related homeobox | ISSX; PRTS; MRX29; MRX32; MRX33; MRX36; MRX38; MRX43; MRX54; MRX76; MRX87; MRXS1; ARX | 300382 | NG_008281.1 | Xp21 |
| OPHN1 | 4983 | oligophrenin 1 | OPN1; MRX60; OPHN1 | 300127 | NG_008960.1 | Xq12 |
| JAR1DIC | 8242 | lysine (K)-specific demethylase 5C | MRXJ; SMCX; MRXSJ; XE169; JARID1C; DXS1272E; KDM5C | 314690 | NG_008085.1 | Xp11.22-p11.21 |
| FTSJ1 | 24140 | FtsJ homolog 1 (*E. coli*) | JM23; MRX9; SPB1; TRM7; CDLIV; MRX44; FTSJ1 | 300499 | NG_008879.1 | Xp11.23 |
| SLC6A8 | 6535 | solute carrier family 6 (neurotransmitter transporter, creatine), member 8 | CRT; CT1; CRTR; MGC87396; SLC6A8 | 300036 | NC_000023.9 | Xq28 |
| DLG3 | 1741 | discs, large homolog 3 (*Drosophila*) | MRX; MRX90; NEDLG; NE-Dlg; SAP102; SAP-102; KIAA1232; DLG3 | 300189 | NC_000023.9 | Xq13.1 |
| TM4SF2 | 7102 | letraspanin 7 | A15; MXS1; CD231; MRX58; CCG-B7; TM4SF2; TALLA-1; TM4SF2b; DXS1692E; TSPAN7 | 300096 | NG_009160.1 | Xp11.4 |
| ZNF41 | 7592 | zinc finger protein 41 | MRX89; MGC8941; ZNF41 | 314995 | NG_008238.1 | Xp11.23 |
| FACL4 | 2182 | acyl-CoA synthetase long-chain family member 4 | ACS4; FACL4; LACS4; MRX63; MRX68; ACSL4 | 300157 | NG_008053.1 | Xq22.3-q23 |
| PQBP1 | 10084 | polyglutamine binding protein 1 | SHS; MRX55; MRXS3; MRXS8; NPW38; RENS1; PQBP1 | 300463 | NC_000023.9 | Xp11.23 |
| PEX1 | 5189 | peroxisomal biogenesis factor 1 | ZWS1; PEX1 | 602136 | NG_008341.1 | 7q21.2 |
| PXMP3 | 5828 | peroxisomal membrane protein 3, 35 kDa | PAF1; PEX2; PMP3; PAF-1; PMP35; RNF72; PXMP3 | 170993 | NG_008371.1 | 8q21.1 |
| PEX6 | 5190 | peroxisomal biogenesis factor 6 | PAF2; PAF-2; PXAAA1; PEX6 | 601498 | NG_008370.1 | 6p21.1 |
| PEX10 | 5192 | peroxisomal biogenesis factor 10 | NALD; RNF69; MGC1998; PEX10 | 602859 | NG_008342.1 | 1p36.32 |
| PEX12 | 5193 | peroxisomal biogenesis factor 12 | PAF-3; PEX12 | 601758 | NG_008447.1 | 17q12 |

TABLE 1-continued

Target Nucleic Acids

| Gene name | Gene ID | Description | Gene aliases | OMIM | RefSeqGene | Chromosome map position |
|---|---|---|---|---|---|---|
| PEX5 | 5830 | peroxisomal biogenesis factor 5 | PXR1; PTS1R; PTS1-BP; FLJ50634; FLJ50721; FLJ51948; PEX5 | 600414 | NG_008448.1 | 12p13.31 |
| PEX26 | 55670 | peroxisomal biogenesis factor 26 | FLJ20695; PEX26M1T; Pex26pM1T; PEX26 | 608666 | NG_008339.1 | 22q11.21 |

The mutations listed in Table 2 are documented polymorphisms in several disease-associated genes (CFTR is mutated in cystic fibrosis, GBA is mutated in Gaucher disease, ASPA is mutated in Canavan disease, HEXA is mutated in Tay Sachs disease). The polymorphisms are of several types: insertion/deletion polymorphisms which will cause frameshifts (and thus generally interrupt protein function) unless the insertion/deletion length is a multiple of 3 bp, and substitutions which can alter the amino acid sequence of the protein and in some cases cause complete inactivation by introduction of a stop codon.

TABLE 2

Non-limiting examples of polymorphisms

| Gene name | GeneID | SNP ID | Mutation | SEQ ID NO: |
|---|---|---|---|---|
| CFTR | 1080 | rs63500661 | TCACATCACCAAGTTAAAAAAAAAAA[A/G]GGGGCGGGGGGGCAGAATGAAAATT | 1 |
| CFTR | 1080 | rs63107760 | AAACAAGGATGAATTAAGTTTTTTTT[-/T]AAAAAAGAAACATTTGGTAAGGGGA | 2 |
| CFTR | 1080 | rs62469443 | ATCACCAAGTTAAAAAAAAAAAGGG[A/G]CGGGGGGGCAGAATGAAAATTGCAT | 3 |
| CFTR | 1080 | rs62469442 | CTATTGAACCAGAACCAAACAGGAAT[A/G]CCATAGCATTTTGTAAACTAAACTG | 4 |
| CFTR | 1080 | rs62469441 | CAGGAGTTCAAGACCAGCCTACTAAA[A/C]CACACACACACACACACACACAC | 5 |
| CFTR | 1080 | rs62469439 | GATTAAATAATAGTGTTTATGTACCC[C/G]GCTTATAGGAGAAGAGGGTGTGTGT | 6 |
| CFTR | 1080 | rs62469438 | ATTGTTATCTTTTCATATAAGGTAAC[A/T]GAGGCCCAGAGAGATTAAATAACAT | 7 |
| CFTR | 1080 | rs62469437 | TAATTTTAATTAAGTAAATTTAATTG[A/G]TAGATAAATAAGTAGATAAAAATA | 8 |
| CFTR | 1080 | rs62469436 | GTATAAAAAAAAAAAAAAAAAAGTT[A/T]GAATGTTTTCTTGCATTCAGAGCCT | 9 |
| CFTR | 1080 | rs62469435 | ATACTAAAAATTTAAAGTTCTCTTGC[A/G]ATATATTTTCTTAATATCTTACATC | 10 |
| CFTR | 1080 | rs62469434 | TGCTGGGATTACAGGCGTGAGCCACC[A/G]CGCCTGGCCTGATGGGACATATTTT | 11 |
| CFTR | 1080 | rs62469433 | CTACAATATAAGTATAGTATTGCAAA[A/C]CCATCAGGAAGGGTGTTAACTATTT | 12 |
| CFTR | 1080 | rs61763210 | GTTGTCTCCAAACTTTTTTTCAGGTG[-/AGA]AGGTGGCCAACCGAGCTTCGGAAAG | 13 |
| CFTR | 1080 | rs61720488 | TTTTTTCATAAAAGATTATATAAAGG[A/C]TATTGCTTTTGAATCACAAACACTA | 14 |
| CFTR | 1080 | rs61481156 | ATCTAGTGAGCAGTCAGGAAAGAGAA[C/T]TTCCAGATCCTGGAAATCAGGGTTA | 15 |
| CFTR | 1080 | rs61443875 | TAGAGTATAAAAAAAAAAAAAAAAAA[-/A]GTTTGAATGTTTTCTTGCATTCAGA | 16 |
| CFTR | 1080 | rs61312222 | TGCAAATGCCAACTATCAAAGATATT[C/G]GAGTATACTGTCAATAAACTTCATA | 17 |

TABLE 2-continued

Non-limiting examples of polymorphisms

| Gene name | GeneID | SNP ID | Mutation | SEQ ID NO: |
|---|---|---|---|---|
| CFTR | 1080 | rs61159372 | TCCTCAACAGTTAGAAACAATATTTT[C/G]AGTGATTTCCCATGCCAACTTTACT | 18 |
| CFTR | 1080 | rs61094145 | TTTTTGGTATTGTTGTTAAATAAGTG[A/G]GAATTCAATACAGTATAATGTCTGT | 19 |
| CFTR | 1080 | rs61086387 | CTTGAAATCGGATATATATATATATA[-/TGTATATATATATATATATATATATATACATATATATATATA]GTATTATCCCTGTTTTCACAGTTTT | 20 |
| CFTR | 1080 | rs60996744 | AGAGGGGCTGTGAAGGACACCAAGGA[A/G]GAGACTAAGAGCCAGGAGGGAAAAC | 21 |
| CFTR | 1080 | rs60960860 | TAGAGTTTATTAGCTTTTACTACTCT[A/G]CTTAGTTACTTTGTGTTACAGAATA | 22 |
| CFTR | 1080 | rs60923902 | ACTAGTGATGATGAGCTTCTTTTCAT[-/AT]GTTTGTTGGCTGCATAAATGTCTTC | 23 |
| CFTR | 1080 | rs60912824 | GCAGAGAAAAGAGGGGCTGTGAAGGA[C/G]ACCAAGGAGGAGACTAAGAGCCAGG | 24 |
| CFTR | 1080 | rs60887846 | TTCAGAGGTCTACCACTGGTGCATAC[G/T]CTAATCACAGTGTCGAAAATTTTAC | 25 |
| CFTR | 1080 | rs60793174 | AAGAAAGAGCAAAAGAGGGCAAACTT[C/T]TCATACATTTTTGATGTCGAAACCA | 26 |
| CFTR | 1080 | rs60788575 | CCTAAAGTTTAAAAAGAAAAAAAAAA[-/A]GGAAGAAGGAATTAAAAATCCAAAG | 27 |
| CFTR | 1080 | rs60760741 | GTGTGTGTGTGTATATATATATATAT[A/T]TATATATTTTTTTTTCCTGAGCCA | 28 |
| CFTR | 1080 | rs60456599 | AAACTGTTGATGTTTTCATTTATTTA[C/G]ATCATTGGAAAACTTTAGATTCTAG | 29 |
| CFTR | 1080 | rs60363249 | TTTATCCATTCTTAACCAGAACAGAC[A/G]TTTTTTCAGAGCTGGTCCAGGAAAA | 30 |
| CFTR | 1080 | rs60355115 | TTGAAATCGGATATATATATATATAT[A/G]TATATATATATATATATATATAT | 31 |
| CFTR | 1080 | rs60308689 | TAGTTTTTTATTTCCTCATATTATTT[-/T]CAGTGGCTTTTTTCTTCCACATCTTT | 32 |
| CFTR | 1080 | rs60271242 | ACATAGTTCTCAGTGGTACAACTACA[A/G]GTGATTTCTCTTTTCTTATTTCTGG | 33 |
| CFTR | 1080 | rs60010318 | AGAGCAATGGCATCCCTTGTCTTGTG[C/T]TATACAGGATGCAGCAATTTATAGG | 34 |
| CFTR | 1080 | rs59961323 | TTCTGTCTACATAAGATGTCATACTA[A/G]ATTATCTTTTCCAGCATGCATTCAG | 35 |
| CFTR | 1080 | rs59961270 | CAGGGTGGCATGTTAGGCAGTGCTTA[A/G]AATAAATGAGTTGGTTATACAAGTA | 36 |
| CFTR | 1080 | rs59837506 | AGGACACACACACACACACACACACA[-/CA]TGCACACACATTTAAATAGATGCAT | 37 |
| CFTR | 1080 | rs59572090 | TAAAAAATTGGTATAATGAAATTGCA[C/T]TTGTAGTCTTTGGACATTTAAATCC | 38 |
| CFTR | 1080 | rs59548252 | TTTCAATACTTAAGAGGTACGCAGAG[A/G]AAAGAGGGGCTGTGAAGGACACCAA | 39 |
| CFTR | 1080 | rs59519859 | CAGCAATGAATATTTTGAGGCTGAGG[C/T]GCTGAGGGGTAAAATTGCAGCCTGG | 40 |
| CFTR | 1080 | rs59509837 | TTATGGTTTATATTTTGTGTCTTCT[-/CTTT]AACACATCTTTTCTAGCAGAATTCA | 41 |

TABLE 2-continued

Non-limiting examples of polymorphisms

| Gene name | GeneID | SNP ID | Mutation | SEQ ID NO: |
|---|---|---|---|---|
| CFTR | 1080 | rs59417037 | GTATTTTAGTTTTTTTTTTGTTTG[-/T]TTTGTTTTGTTTTGTTTTGTTTTTG | 42 |
| CFTR | 1080 | rs59159458 | TGGGTGACTCCATTTTACTTTTAGT[C/T]TGGTCTGTTGAGGCCTCGTGAGAGA | 43 |
| CFTR | 1080 | rs59048119 | TATTTTCATGTATTTTAGTTTTTTTT[-/TTTT]GTTTGTTTTGTTTTGTTTTGTTTTG | 44 |
| CFTR | 1080 | rs58970500 | GTGTGTGTGTATATATATATATATAT[A/T]TATATTTTTTTTTCCTGAGCCAAA | 45 |
| CFTR | 1080 | rs58942292 | AACCTATTAGCATGTCTGGCAGAAAA[-/A]TAGATACTTAATAAATTTCTTAAAT | 46 |
| CFTR | 1080 | rs58917054 | GAGGCTTAGACAGTTTAAGTAACTCA[A/G]GCATGGTTACACAACTAGCTAGGGC | 47 |
| CFTR | 1080 | rs58837484 | GTGTGAGTATTATGAGACCATATGTT[A/G]GGAGATTTTATTTGGTATTGAGGAT | 48 |
| CFTR | 1080 | rs58829491 | GAAACCCCACCCCTTCTATAGTTTTC[C/T]CTTTAATATTTACAATGGAACCATT | 49 |
| CFTR | 1080 | rs58805195 | CATATATATATAGTGTGTGTGTGTGT[A/G]TATATATATATATATATATATTTTT | 50 |
| GBA | 2629 | rs60866785 | CGAGCGAGAGAGAGAGAGAGAGAGAG[-/AG]GAGCCGGCGCGAGAACTACGCATGC | 51 |
| GBA | 2629 | rs60239603 | GGCAGGTAATATCTAGTACCTTACTT[A/T]TATTTCCTGAGCACATTCTACATTT | 52 |
| GBA | 2629 | rs56310840 | GGCCAGGAATGGGAGTGCTTAGGTGC[A/G]GAGGTGGCACTGTTCCCGCAGCTGC | 53 |
| GBA | 2629 | rs41264927 | GAAAACTCCATCCCCTCAGGGTCAT[C/T]AGATGAAGAGAAGACCACAGGGGTT | 54 |
| GBA | 2629 | rs41264925 | TGTAGGTAAGGGTCACATGTGGGAGA[C/G]GCAGCTGTGGGTAGGTCAGCCCTGT | 55 |
| GBA | 2629 | rs36024691 | CCAAGAAGGCGCCATTACACTCCAGC[-/C]TGGGCGACAGGGCGAGACTCCCTCA | 56 |
| GBA | 2629 | rs36024092 | TGCCACACCCAGCTAATTTGTGTGTG[-/G]TATGTGTGTATGTATGTGTGTGT | 57 |
| GBA | 2629 | rs35682967 | GTTCCTCCAGTAATTTTTTTTTTTTT[-/T/]GGTTTTGAGACAGAGTCTTGCCCTG | 58 |
| GBA | 2629 | rs35033592 | ATCATGCCCAGATAATTTTTTTTTTT[-/T]GTATTTTAGTAGACACAGGGTTTCA | 59 |
| GBA | 2629 | rs34732744 | CGAGCGAGAGAGAGAGAGAGAGAGAG[-/AG]GAGCCGGCGCGAGAACTACGCATGC | 60 |
| GBA | 2629 | rs34620635 | CCTGTGAGGGGCACATTCCTTAGTAG[-/C]TAAGGAGTTGGGGGTGTGAAGATCC | 61 |
| GBA | 2629 | rs34302637 | ACAGGCTACTGGCTGGGCCCAGGCAA[-/A]GGGGGCCTTGGCAGGAAAAGTTCCT | 62 |
| GBA | 2629 | rs33949225 | GCGAGAGAGAGAGAGAGAGAGAGAGG[-/AG]AGCCGGCGCGAGAACTACGCATGCG | 63 |
| GBA | 2629 | rs28678003 | AAGAAGAAAATAAAAAGAAAGTGGG[C/T]CAGACCGAGAGAACAGGAAGCCTGA | 64 |
| GBA | 2629 | rs28559737 | AAGGACAAAGGCAAAGAGACAAAGGC[G/T]CAACACTGGGGGTCCCCAGAGAGTG | 65 |
| GBA | 2629 | rs28373017 | TACCTAGTCACTTCCTGCCTCCATGG[C/T]GCAAAAGGGGATGGGTGTGCCTCTT | 66 |

TABLE 2-continued

Non-limiting examples of polymorphisms

| Gene name | GeneID | SNP ID | Mutation | SEQ ID NO: |
|---|---|---|---|---|
| GBA | 2629 | rs12752133 | CTCTTCCGAGGTTCCACCCTGAACAC[C/T]TTCCTGCTCCCTCGTGGTGTAGAGT | 67 |
| GBA | 2629 | rs12747811 | TTCTGACTGGCAACCAGCCCCACTCT[C/T]TGGGAGCCCTCAGGAATGAACTTGC | 68 |
| GBA | 2629 | rs12743554 | gctcagcctcccaggctggagtgcag[A/T]ggcgcgatctcggctcaccgcaacc | 69 |
| GBA | 2629 | rs12041778 | CATGAACCACATCAAATGAGATTTAG[C/T]GGGAGTGGCACACACAGTCATGACC | 70 |
| GBA | 2629 | rs12034326 | AAGCAGCCCTGGGGAGTCGGGGCGGG[A/G]CCTGGATTGGAAAAGAGACGGTCAC | 71 |
| GBA | 2629 | rs11558184 | CTCCAAGTTCTGGGAGCAGAGTGTGC[A/G]GCTAGGCTCCTGGGATCGAGGGATG | 72 |
| GBA | 2629 | rs11430678 | GTTCCTCCAGTAAtttttttttttt[-/G/T]gttttgagacagagtcttgccctgt | 73 |
| GBA | 2629 | rs11264345 | CTAGTACCTTACTTCCCTCAAGTTCA[A/T]TCATCTCACAGATATTTCCTGAGCA | 74 |
| GBA | 2629 | rs10908459 | aattagccgtgcgtggtggcgggtgc[C/T]tgtaatcccacgtacttgggaggct | 75 |
| GBA | 2629 | rs10796940 | CCATGGCCAGCCGGGGAGGGGACGGG[A/C]ACACACAGACCCACACAGAGACTCA | 76 |
| GBA | 2629 | rs10668496 | agcgagagagagagagagagagagag[-/AG]gagCCGGCGCGAGAACTACGCATGC | 77 |
| GBA | 2629 | rs7416991 | CGTAGCAGTTAGCAGATGATAGGCGG[C/G/T]GAAATCTTATTTCACAGGGCATTAA | 78 |
| GBA | 2629 | rs4024049 | CTGGCCCTGGTGACAGTGGGGCTGTG[C/T]GTGGGGCCAGAGCCTTCTCAGAGGT | 79 |
| GBA | 2629 | rs4024048 | CAGATACTGGCCCTGGTGACAGTGGG[A/G]CTGTGCGTGGGGCCAGAGCCTTCTC | 80 |
| GBA | 2629 | rs4024047 | GACAGATACTGGCCCTGGTGACAGTG[G/T]GGCTGTGCGTGGGGCCAGAGCCTTC | 81 |
| GBA | 2629 | rs3841430 | GGCTCctctctctctctctctctctc[-/TC]gctcgctctctcgctctctcgctct | 82 |
| GBA | 2629 | rs3754485 | GTTTCAGACCAGCCTGGCCAACATAG[C/T]GAAACCCCATCTCTACTAAAAATAA | 83 |
| GBA | 2629 | rs3205619 | AGTGGGCGATTGGATGGAGCTGAGTA[C/T]GGGGCCCATCCAGGCTAATCACACC | 84 |
| GBA | 2629 | rs2990227 | CCGGGCTCCGTGAATGTTTGTCACAT[C/G]TCTGAAGAACGTATGAATTACATAA | 85 |
| GBA | 2629 | rs2990226 | GAATCCCAACCCCGACGCTCGTCGCC[C/G]GGCTCCGTGAATGTTTGTCACATGT | 86 |
| GBA | 2629 | rs2990225 | GCGAATCCCAACCCCGACGCTCGTCG[C/T]CGGGCTCCGTGAATGTTTGTCACAT | 87 |
| GBA | 2629 | rs2990224 | TGGGCAGAAGTCAGGGTCCAAAGAAA[G/T]GGCAAAGAAAGTGTcagtggctca | 88 |
| ASPA | 443 | rs63751297 | TAAGAAAGACGTTTTTGATTTTTTC[A/G]GACTTCTCTGGCTCCACTACCCTGC | 89 |
| ASPA | 443 | rs62071301 | CTGATTCCTGGCCAGGAGCGGTGGCT[C/T]ACGCCTGTAATCCCAGCGCTTTGGG | 90 |
| ASPA | 443 | rs62071300 | TAAAAATGCTGATTCCTGGCCAGGAG[C/T]GGTGGCTCACGCCTGTAATCCCAGC | 91 |

TABLE 2-continued

Non-limiting examples of polymorphisms

| Gene name | GeneID | SNP ID | Mutation | SEQ ID NO: |
|---|---|---|---|---|
| ASPA | 443 | rs62071299 | TTTAAAAATGCTGATTCCTGGCCAGG[A/C]GC GGTGGCTCACGCCTGTAATCCCA | 92 |
| ASPA | 443 | rs62071297 | CAAGACCTGTCAAAGATCTGAGAAAT[A/T]TT ACCCGACTTACAAGCTAACCATT | 93 |
| ASPA | 443 | rs61697033 | ACTGTAATAAGTGCTGTAAAAGAAAT[A/G]C ACAAAATAATATAGCAGAGGGTAT | 94 |
| ASPA | 443 | rs60743592 | CTTGAGGTCAGGAGTTCAAGACCAGT[C/T]TG GGCAACATGGGGAAAACCTTGTC | 95 |
| ASPA | 443 | rs60666840 | AGGTTGCAGTGAGCCGAGATCATGCC[A/G]TT GCACTCCAGCCGGGGCAACAAAA | 96 |
| ASPA | 443 | rs60147514 | ACAAGTGTCTTGAAATTATCTGTGAT[C/T]TG CTATAGAGCAATACTTTTGTAAA | 97 |
| ASPA | 443 | rs59930743 | GTGGGTATATGCAGCTCTATGCACTA[C/T]CT GCTCATTTATTTGGTAAATCTAA | 98 |
| ASPA | 443 | rs59690349 | TGTGTGTGTGTGCGTGTGTGTGTGTG[-/T GTGTGTG]ATCATAAGAGTGGCTGCAGCAA ACT | 99 |
| ASPA | 443 | rs59676360 | AGTCTGGAGTGCAATGGTGCAATCTC[A/G]GC TCACTGCAGCCTCCACCTCCGGG | 100 |
| ASPA | 443 | rs59335404 | CTCCTAATGGATATTTCCTAAATTTT[G/T]CTG AACAGAATTTAACTTGAGCTGG | 101 |
| ASPA | 443 | rs58879097 | ATTTAAAAATGGATTTCTAGAAAAAC[A/G]AT CACATACTTGAATATTTTAGCAA | 102 |
| ASPA | 443 | rs58686774 | CTATAAATGGGTAGCATGAGGGATTC[A/G]A GGAGGTGGCTGAAAGAAGCACGTA | 103 |
| ASPA | 443 | rs57511162 | AAGAAACCAAGCATAGTAGAGTGTTA[A/G]A AAACCAAAGCAACTAAACAACTGT | 104 |
| ASPA | 443 | rs55859596 | CGGGGCTCAGAACTTGTAACAGAAAA[A/T]T AAAATATACTCCACTCAAGGGAAT | 105 |
| ASPA | 443 | rs55742972 | TACTACACTTCACGGATACTGTACTT[-/G TACTT]TTTTTCCAAATTGAAGGTTTTGGC | 106 |
| ASPA | 443 | rs55640436 | TTGTTTTGTTTTTGTTTTTGTTTTT[-/G TTTTTGTTTTT]TGAGATGGAGTCTCGCTCT GTCGCC | 107 |
| ASPA | 443 | rs36225687 | TTTGCCTTACTACACTTCACGGATAC[-/T GTACT]TGTACTTTTTTTCCAAATTGAAGGT | 108 |
| ASPA | 443 | rs36051310 | GAGGTGGCTGAAAGAAGCACGTATCC[-/C] TGATGGCATGGTTGCGGGTATATG | 109 |
| ASPA | 443 | rs36034906 | GAGAAAAGCAGTTCCTGGAACACCCC[-/C] ACCCCTTAACCCCTTATCTCTGCTT | 110 |
| ASPA | 443 | rs36033666 | TTACATATGTATACATGTGCCATGTT[-/T] GGTGTGCCGCACCCATTAACTCGTC | 111 |
| ASPA | 443 | rs35730123 | CTTTTTCCAGATTTTTTTTTTTTT[-/T] GAGACAGAGTTTCACTCTTGTTGCC | 112 |
| ASPA | 443 | rs35629100 | TTTGGAAATCTTAAGCTTTTATTTGG[-/G] TGTCACAGAGAAACAGGATCTGTAT | 113 |
| ASPA | 443 | rs35614631 | TACTTTAAGTTTTAGGGTACATGTGC[-/A] CCATGTGCAGGTTTGTTACATATGT | 114 |

TABLE 2-continued

Non-limiting examples of polymorphisms

| Gene name | GeneID | SNP ID | Mutation | SEQ ID NO: |
|---|---|---|---|---|
| ASPA | 443 | rs35225782 | ATTCATGACCAGCCACATAAATGCAC[-/A]GTATTACTTCGCAAGCATGCCAATG | 115 |
| ASPA | 443 | rs35178659 | GTGCACTAGAATTAGCTAAAGTGGGG[-/G]AAAAAAAGATGCATTTGATGGTCTA | 116 |
| ASPA | 443 | rs35095578 | AACCTCCACCTCCCAGGTTCAAGAGA[-/A]TTCTCCTGCCTCAGCCTCCCAAGTA | 117 |
| ASPA | 443 | rs35002210 | CCTCCCTGTGATCCGAAGTAGCAGAC[A/G]TACTTAACTTCCATGGTGGATTGTT | 118 |
| ASPA | 443 | rs34744839 | AAAACATTATTATATCTAGAAAAAAA[-/A]TGTATCTTAACCATTGTGGGAAGTG | 119 |
| ASPA | 443 | rs34680506 | TTGAAGGTAAAATCATAGGGAGTTGG[-/G]AGCTGTCCTCTTGCGCTGAATCAGT | 120 |
| ASPA | 443 | rs34365618 | ACTTGTGGCCTTTTTGGAGAGGTTAG[-/CA]ACTCTGAAAACTCTGTCCCTGGACC | 121 |
| ASPA | 443 | rs34275920 | GAAGGAGAAAAAGAGAGGAAATAAGT[-/T]AAAATAATAAACACAATTAATAAAG | 122 |
| ASPA | 443 | rs34109510 | TGTATACATGTGCCATGTTGGTGTGC[C/T]GCACCCATTAACTCGTCATTTAGCA | 123 |
| ASPA | 443 | rs34054576 | TCACCTGTCACCTCCTATAGAACTTT[-/C]CCCTGACCCTCCTCTATAGCATTAA | 124 |
| ASPA | 443 | rs34015272 | ATAAATGATCATCATTCACAGTAGGG[-/G]TTTTGTTTTGTTTTTTTCTGGAAA | 125 |
| ASPA | 443 | rs34002091 | ACAGACATATCTACAAACACACTTTT[-/T]CACATATTTGTGTAAGTCATTTATG | 126 |
| ASPA | 443 | rs28940574 | AAAGACAACTAAACTAACGCTCAATG[A/C]AAAAAGTATTCGCTGCTGTTTACAT | 127 |
| ASPA | 443 | rs28940279 | TACCGTGTACCCCGTGTTTGTGAATG[A/C]GGCCGCATATTACGAAAAGAAAGAA | 128 |
| ASPA | 443 | rs17850703 | CAGGGCTGGAGGTAAAACCATTTATT[A/G]CTAACCCCAGAGCAGTGAAGAAGTG | 129 |
| ASPA | 443 | rs17222495 | TTCTTCATTGCCTATTGAAGAGAGAG[C/T]GGAATGCTTTGGTTGCCAGATATGG | 130 |
| ASPA | 443 | rs17175228 | CACAAGATCTCATTACTCAGGAGCTG[C/T]CCAAGTGTCTAATGTACTTAGTTAA | 131 |
| ASPA | 443 | rs16953074 | TTCTGTGTAACATTTCATTTAAGCAA[A/G]GGATTCGGCAAATCAAAAATTGTCA | 132 |
| ASPA | 443 | rs16953070 | TAAAACGTATTGAAGGTATTATTGAC[G/T]CTGTTGAAGCAAAGAGAACAAAACA | 133 |
| HEXA | 3073 | rs62022858 | ATCTGCTCTTCCAGTTGGATGACAAG[C/T]CTTGCTGTCTAACACCTGCTGCAGA | 134 |
| HEXA | 3073 | rs62022857 | CCATTTTTGTTGTATTTTTTTTTC[C/T]TGAATACTTTTATCGCAGTTGGTT | 135 |
| HEXA | 3073 | rs62017872 | CCCTGTCTCTAAAAGAAAAAAAAAAA[A/G]AAAAAAAAAGAAAACAAAACCCAA | 136 |
| HEXA | 3073 | rs62017871 | AGTGGCTCCAAAAAGGTCATGGAACC[C/T]CTTGAGGATGATGCAAATTGACTCT | 137 |
| HEXA | 3073 | rs61662730 | TAAAGTTACTTTTCTTTTATTGACTT[C/T]CCCTTATTTTTAACCTTATGCTTT | 138 |
| HEXA | 3073 | rs61329913 | CAGAGTTAAAAAAAAAAAAAAAAAA[-/A]GGAAGTAGCAGCAACAGCTTGGAAA | 139 |

TABLE 2-continued

Non-limiting examples of polymorphisms

| Gene name | GeneID | SNP ID | Mutation | SEQ ID NO: |
|---|---|---|---|---|
| HEXA | 3073 | rs60920713 | GTTGCCCAGGGTTGAGTGCAGAGGCA[C/T]ATTTGGCTCACAGCAACCTCTGCC | 140 |
| HEXA | 3073 | rs60783213 | AAGGCTTTTTTTTTTTTTTTTTTT[-/TTTT]GAGACAGAGTCTTGCTGTGTCACCC | 141 |
| HEXA | 3073 | rs60644867 | GCCTACATTCTGCAAAGAGGAGGGAA[C/G]ATTCACAGCTCCATACTTGAACCCT | 142 |
| HEXA | 3073 | rs60288568 | CCAAAGGAGAATAGCTCTAGGGGAGG[C/G]AGGTGGATGAGTATGCATGGGGGAG | 143 |
| HEXA | 3073 | rs59888548 | GACTCCATCTCAAAAAAAAAAAAAA[-/A]TGCAGTCTAATGGCAGAATTAGACT | 144 |
| HEXA | 3073 | rs59733856 | TTATTTATTTATTTATTTTTGA[A/G]ACAGGGTCTCTGTTGTCCAGGCTGG | 145 |
| HEXA | 3073 | rs59427837 | TTTTGAGGCAGGGTCTCACTCTGTTG[C/T]CCAGGGTTGAGTGCAGAGGCACATC | 146 |
| HEXA | 3073 | rs59171976 | CGCCTTGCGAAGGCCCCACAGCTTGC[C/T]TGTGACAAACGTTCATAGGCAAATG | 147 |
| HEXA | 3073 | rs58706602 | GGAGGTCTGTACAAAGCACCACCTAC[C/T]TCATGGGTCAGTTTCCACAGCAGAA | 148 |
| HEXA | 3073 | rs58696963 | GAATCTTATAATTCACTGTGTACCTC[-/CCTC]TGTTTCATATTTTCGCAATTGAACT | 149 |
| HEXA | 3073 | rs58610850 | AACATAGTATCTAATATAGCTTTACA[C/T]CCAAAGCCAAAATATGAATACACTG | 150 |
| HEXA | 3073 | rs58016062 | TTGTTTTGTTTTGTTTGGGGGGGGGG[-/G]TTGTTTTTCTGAGAGGGAGTCTTGC | 151 |
| HEXA | 3073 | rs57733983 | CATACCAAAGGGCAGCTGGAGGGATAC[C/T]AGACGGAAGTCATGTGGAGAGTGAA | 152 |
| HEXA | 3073 | rs57476645 | CAGGTGTGAGCCACCACGACCACCAA[A/T]TTAGCTCTTTTTACTCCTTCCCTTC | 153 |
| HEXA | 3073 | rs56870003 | AGTGGTAGCTGATTTTGCTTCTGGAT[A/C]CTTTGCCACCTTCCCACTCTTTAAT | 154 |
| HEXA | 3073 | rs56338339 | AAAGACCTGTTTCTTAAAAAAAAAAA[-/AGAAAAAAAAAAA]GAAAGAAAAGAAAAGAAAAAAACAG | 155 |
| HEXA | 3073 | rs55995352 | TAAAAAATCTTTCAATGAGGAGATGT[C/T]CCCAGAGCAAGACAGCTGTAGGATG | 156 |
| HEXA | 3073 | rs55860138 | AAAAGAAAAAAAAAAAAAAAAAAAA[-/A]GAAAACAAAACCCAAACCCATAAAG | 157 |
| HEXA | 3073 | rs55743646 | CCTGTCTCTAAAAGAAAAAAAAAAAA[A/G]AAAAAAAAGAAAACAAAACCCAAA | 158 |
| HEXA | 3073 | rs55665666 | GTTATCATAGAAAAATATCACACTCT[-/GT]CTGTATCCCCACTTCCAGAAACTGT | 159 |
| HEXA | 3073 | rs36106892 | CAGGAGCTCATAGAATTACATACAAT[-/C]TTTTTTTTTTTTTTTGAGACAGCG | 160 |
| HEXA | 3073 | rs36091525 | TTGAGAATCTTATAATTCACTGTGTA[-/CCTC]CCTCTGTTTCATATTTTCGCAATTG | 161 |
| HEXA | 3073 | rs35949555 | CCACTACCACAGTGCCTAGAGAACAA[C/T]ATGTGTTTAATAATATTTAAATAAT | 162 |
| HEXA | 3073 | rs35827424 | CCCTGTCTCTAAAAGAAAAAAAAAAA[-/A]AAAAAAAAAGAAAACAAAACCCAA | 163 |
| HEXA | 3073 | rs35729578 | CCATTATATCATTCATTTCCCACTCA[-/T]TTTCTTCATTCCAACCAAGATATAT | 164 |

TABLE 2-continued

Non-limiting examples of polymorphisms

| Gene name | GeneID | SNP ID | Mutation | SEQ ID NO: |
|---|---|---|---|---|
| HEXA | 3073 | rs35649102 | TCCGTCTCAAAAAAAAAAAAAAAAG[-/A]GAAAGGAATTATTCTCATGTATACA | 165 |
| HEXA | 3073 | rs35118677 | CTGGGGCAGTTAAAAAGAAAAACAAA[-/C]CCCTGGTCCCTGCCCTTGAGGAGAT | 166 |
| HEXA | 3073 | rs35005352 | CTCCAGGGTCCCATTCCAGGACCACA[-/C]GCCTGCTACCTCTGCAGCTCACTCA | 167 |
| HEXA | 3073 | rs34736306 | GGATTGACATATACCAGTTAGACGGA[-/T]TTTTTTTTTCCATAAACCAGGCTCA | 168 |
| HEXA | 3073 | rs34607939 | ACAAATAATTACTACATATCTACAAC[A/G]TTCCAGATACAGAAGAAATGGCCAA | 169 |
| HEXA | 3073 | rs34496117 | TAAACACACTTGAAACATCATATAAA[-/ATG]ATATTACTACAAGACTTAACCGTAA | 170 |
| HEXA | 3073 | rs34300017 | ACACAGGTAATCCATGTTTATTATAG[-/A]AAAATGCCACATTACTCTTTATTGA | 171 |
| HEXA | 3073 | rs34206496 | AGTTATCATAGAAAAATATCACACTC[-/TG]TCTGTATCCCCACTTCCAGAAACTG | 172 |
| HEXA | 3073 | rs34110830 | AATGAACTTACAGGAAGGTAATATAT[-/G]GGAAATAAACATCTTATTGAATTTA | 173 |
| HEXA | 3073 | rs34093438 | GGACCCCTGAAAGGCACAAGACACCC[-/T]TTCAGGTTCACACTTCCTGAAAGCT | 174 |
| HEXA | 3073 | rs34085965 | CCACCAATCACCAGAGCCTTCTGCTC[A/G]GGGGTACCTGAGGGAAAACAAGCAA | 175 |
| HEXA | 3073 | rs34004907 | AAAGACTGAAAAAACATTCATAACTA[-/T]TTTTCTTGTTATCCTCGGAAATGTC | 176 |
| HEXA | 3073 | rs28942072 | TATCTTCATCTTGGAGGAGATGAGGT[C/T]GATTTCACCTGCTGGAAGTCCAACC | 177 |
| HEXA | 3073 | rs28942071 | TTGCCTATGAACGTTTGTCACACTTC[C/T]GCTGTGAGTTGCTGAGGCGAGGTGT | 178 |
| HEXA | 3073 | rs28941771 | GCTTGCTGTTGGATACATCTCGCCAT[C/T]ACCTGCCACTCTCTAGCATCCTGGA | 179 |
| HEXA | 3073 | rs28941770 | CCGGGGCTTGCTGTTGGATACATCTC[G/T]CCATTACCTGCCACTCTCTAGCATC | 180 |

3. Nucleic Acid Target Length Evaluation:

In some embodiments, aspects of the invention relate to methods for detecting nucleic acid deletions or insertions in regions containing nucleic acid sequence repeats.

Genomic regions that contain nucleic acid sequence repeats are often the site of genetic instability due to the amplification or contraction of the number of sequence repeats (e.g., the insertion or deletion of one or more units of the repeated sequence). Instability in the length of genomic regions that contain high numbers of repeat sequences has been associated with a number of hereditary and non hereditary diseases and conditions.

For example, "Fragile X syndrome, or Martin-Bell syndrome, is a genetic syndrome which results in a spectrum of characteristic physical, intellectual, emotional and behavioral features which range from severe to mild in manifestation. The syndrome is associated with the expansion of a single trinucleotide gene sequence (CGG) on the X chromosome, and results in a failure to express the FMR-1 protein which is required for normal neural development. There are four generally accepted forms of Fragile X syndrome which relate to the length of the repeated CGG sequence; Normal (29-31 CGG repeats), Premutation (55-200 CGG repeats), Full Mutation (more than 200 CGG repeats), and Intermediate or Gray Zone Alleles (40-60 repeats)."

Other examples include cancer, which has been associated with microsatellite instability (MSI) involving an increase or decrease in the genomic copy number of nucleic acid repeats at one or more microsatellite loci (e.g., BAT-25 and/or BAT-26). The are currently many sequencing-based assays for determining the number of nucleic acid sequence repeats at a particular locus and identifying the presence of nucleic acid insertions or deletions. However, such techniques are not useful in a high throughput multiplex analysis where the entire length of a region may not be sequenced.

In contrast, in some embodiments, aspects of the invention relate to detecting the presence of an insertion or deletion at a genomic locus without requiring the locus to be sequenced (or without requiring the entire locus to be sequenced). Aspects of the invention are particularly useful for detecting an insertion or deletion in a nucleic acid region that contains high levels of sequence repeats. The presence of sequence repeats at a genetic locus is often associated with relatively high levels of polymorphism in a population due to insertions or deletions of one or more of the sequence repeats at the locus. The polymorphisms can be associated with diseases or predisposition to diseases (e.g., certain polymorphic alleles are recessive alleles associated with a disease or condition). However, the presence of sequence repeats often complicates the analysis of a genetic locus and increases the risk of errors when using sequencing techniques to determine the precise sequence and number of repeats at that locus.

In some embodiments, aspects of the invention relate to determining the size of a genetic locus by evaluating the capture frequency of a portion of that locus suspected of containing an insertion or deletion (e.g., due to the presence of sequence repeats) using a nucleic acid capture technique (e.g., a nucleic acid sequence capture technique based on molecular inversion probe technology). According to aspects of the invention, a statistically significant difference in capture efficiency for a genetic locus of interest in different biological samples (e.g., from different subjects) is indicative of different relative lengths in those samples. It should be appreciated that the length differences may be at one or both alleles of the genetic locus. Accordingly, aspects of the invention may be used to identify polymorphisms regardless of whether biological samples being interrogated at heterozygous or homozygous for the polymorphisms. According to aspects of the invention, subjects that contain one or more loci with an insertion or deletion can be identified by analyzing capture efficiencies for nucleic acids obtained from one or more biological samples using appropriate controls (e.g., capture efficiencies for known nucleic acid sizes, capture efficiencies for other regions that are not suspected of containing an insertion or deletion in the biological sample(s), or predetermined reference capture efficiencies, or any combination thereof. However, it should be appreciated that aspects of the invention are not limited by the nature or presence of the control. In some embodiments, if a statistically significant variation in capture efficiency is detected, a subject may be identified as being at risk for a disease or condition associated with insertions or deletions at that genetic locus. In some embodiments, the subject may be analyzed in greater detail in order to determine the precise nature of the insertion or deletion and whether the subject is heterozygous or homozygous for one or more insertions or deletions. For example, gel electrophoresis of an amplification (e.g., PCR) product of the locus, or Southern blotting, or any combination thereof can be used as an orthogonal approach to verify the length of the locus. In some embodiments, a more exhaustive and detailed sequence analysis of the locus can be performed to identify the number and types of insertions and deletions. However, other techniques may be used to further analyze a locus identified as having an abnormal length according to aspects of the invention.

Accordingly, aspects of the invention relate to detecting abnormal nucleic acid lengths in genomic regions of interest. In some embodiments, the invention aims to estimate the size of genomic regions that are hard to be accessed, such as repetitive elements. However, it should be appreciated that methods of the invention do not require that the precise length be estimated. In some embodiments, it is sufficient to determine that one or more alleles with abnormal lengths are present at a locus of interest (e.g., based on the detection of abnormal capture efficiencies).

In a non-limiting example, fragile X can be used to illustrate aspects of the invention where the size of trinucleotide repeats (genotype) is linked to a symptom (phenotype). However, it should be appreciated that fragile X is a non-limiting example and similar analyses may be performed for other genetic loci (e.g., independently or simultaneously in multiplex analyses).

Use of molecular inversion probes (MIPs) has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). In both cases, oligonucleotide probes are designed which have ends ('targeting arms') that hybridize up-stream and down-stream of the locus that is to be amplified.

Figure 8:
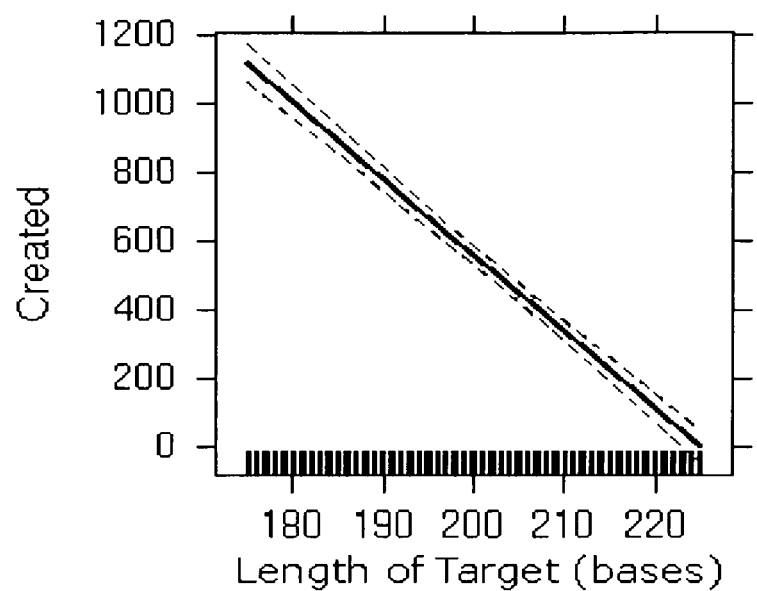
FIG. 8 illustrates that shorter sequences are captured with higher efficiency that longer sequences using MIPs.

In some embodiments, aspects of the invention are based on the recognition that the effect of length on probe capturing efficiency can be used in the context of an assay (e.g., a high throughput and/or multiplex assay) to allow the length of sequences to be determined without requiring sequencing of the entire region being evaluated. This is particularly useful for repeat regions that are prone to changes in size. As illustrated in FIG. 8, which is reproduced from Deng et al., Nature Biotech. 27:353-60, (see Supplemental FIG. 1G of Deng et al.,) illustrates that shorter sequences are captured with higher efficiency that longer sequences using MIPs. The statistical package R and its effects module were used for this analysis. A linear model was used, and each individual factor was assumed to be independent. The dashed lines represent a 95% confidence interval. Shorter target sequences were captured with higher efficiency than long target sequences ($p<2\times10^{-16}$). However, the use of this differential capture efficiency for systematic sequence length analysis was not previously recognized.

In some embodiments, following probe hybridization, polymerase fill-in and ligation reactions are performed to convert the hybridized probe to a covalently-closed, circular molecule containing the desired target. PCR or rolling circle amplification plus exonuclease digestion of non-circularized material is performed to isolate and amplify the circular targets from the starting nucleic acid pool. Since one of the main benefits of the method is the potential for a high degree of multiplexing, generally thousands of targets are captured in a single reaction containing thousands of probes.

According to aspects of the invention, repetitive regions are surrounded by non repetitive unique sequences, which can be used to amplify the repeat-containing regions using, for example, PCR or padlock (MIP)-based method.

Figure 9:
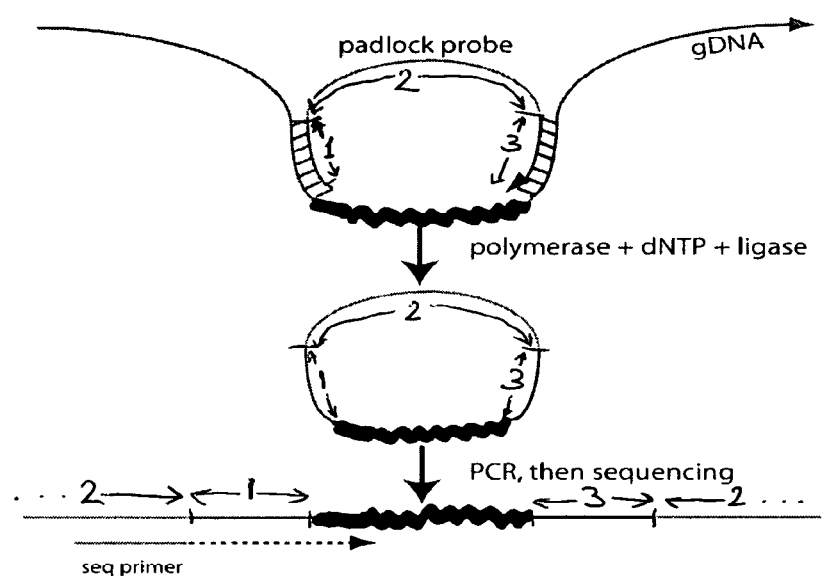
FIG. 9 illustrates a non-limiting scheme of padlock (MIP) capture of a region that includes both repetitive regions (thick wavy line) and the adjacent unique sequence (thick strait line)

In addition to the repetitive regions, a probe (e.g., a MIP or padlock probe) can be designed to include at least a sequence that is sufficient to be uniquely identified in the genome (or target pool). After the probe is circularized and amplified, the amplicon can be end-sequenced so that the unique sequence can be identified and served as the "representative" of the repetitive region as illustrated in FIG. 9. FIG. 9 illustrates a non-limiting scheme of padlock (MIP) capture of a region that includes both repetitive regions (thick wavy line) and the adjacent unique sequence (thick strait line). The regions of the probe are indicated with the targeting arms shown as regions "1" and "3." An intervening region that may be, or include, a sequencing primer binding site is shown as "2." After the padlock is circularized and amplified, it can be end-sequenced to obtain the sequence of the unique sequence, which represents the repetitive region of interest.

Although capturing efficiency is overall negatively correlated with target length, different probe sequences may have unique features. Therefore, multiple probes could be designed and tested so that an optimal one is chosen to be sensitive enough to differentiate repetitive sizes of roughly 0-150 bp, 150-600 bp, and beyond, which represent normal, premutation and full mutation of fragile X syndrome, respectively. However, it should be appreciated that other probe sizes and sequences can be designed, and optionally optimized, to distinguish a range of repeat region size differences (e.g., length differences of about 3-30 bases, about 30-60 bases, about 60-90 bases, about 90-120 bases, about 120-150 bases, about 150-300 bases, about 300-600 bases, about 600-900 bases, or any intermediate or longer length difference). It should be appreciated that a length difference may be an increase in size or a decrease in size.

In some embodiments, an initial determination of an unexpected capture frequency is indicative of the presence of size difference. In some embodiments, an increase in capture frequency is indicative of a deletion. In some embodiments, a decrease in capture frequency is indicative of an insertion. However, it should be appreciated that depending on specific sequence parameters and the relative sizes of the capture probes, the target region, and the deletions or insertions, a change in capture frequency can be associated with either an increase or decrease in target region length. In some embodiments, the precise nature of the change can be determined using one or more additional techniques as described herein.

Accordingly, in some aspects a MIP probe includes a linear nucleic acid strand that contains two hybridization sequences or targeting arms, one at each end of the linear probe, wherein each of the hybridization sequences is complementary to a separate sequence on a the same strand of a target nucleic acid, and wherein these sequences on the target nucleic acid flank the two ends of the target nucleic acid sequence of interest. It should be appreciated that upon hybridization, the two ends of the probe are inverted with respect to each other in the sense that both 5' and 3' ends of the probe hybridize to the same strand to separate regions flanking the target region (as illustrated in FIG. 9 for example).

In some embodiments, the hybridization sequences are between about 10-100 nucleotides long, for example between about 10-30, about 30-60, about 60-90, or about 20, about 30, about 40, or about 50 nucleotides long. However, other lengths may be used depending on the application. In some embodiments, the hybridization Tms of both targeting arms of a probe are designed or selected to be similar. In some embodiments, the hybridization Tms of the targeting arms of a plurality of probes designed to capture different target regions are selected or designed to be similar so that they can be used together in a multiplex reaction. Accordingly, a typical size of a MIP probe prior to fill in is about 60-80 nucleotides long. However, other sizes can be used depending on the sizes of the targeting arms and any other sequences (e.g., primer binding or tag sequences) that are present in the MIP probe. In some embodiments, MIP probes are designed to avoid sequence-dependent secondary structures. In some embodiments, MIP probes are designed such that the targeting arms do not overlap with known polymorphic regions. In some embodiments, targeting arms that can be used for capturing the repeat region of the Fragile X locus can have the following sequences or complementary to these sequences depending on the strand that is captured.

left: CTCCUITYCGGTITCACTTC (SEQ ID NO: 181)
right: ATCTTCTCTTCAGCCCTGCT (SEQ ID NO: 182)

The typical captured size using these targeting arms is about 100 nucleotides in length (e.g., about 30 repeats of a tri-nucleotide repeat).

In some embodiments, the number of reads obtained for the "representative" of the repetitive region is not informative to estimate the target length because it is dependent on the total number of reads obtained. To overcome this, it is useful to include one or more probes that target other "control" regions where no or minimal polymorphism exists among populations. Because of the systematic consistency of capturing efficiency (see, e.g., FIG. 9), the ratio of reads obtained for the repetitive "representative" to reads obtained for the control region(s) will be tuned using DNA with defined numbers of repeats. Ultimately, the ratio can serve as a measure of the repeat length as illustrated in FIG. 10. FIG. 10 illustrates a non-limiting hypothetical relationship between target gap size and the relative number of reads of the repetitive region, which is measured by the ratio of the repeat "representative" reads vs. the "control" region reads. The unit of y-axis is arbitrary.

In some embodiments, to better tell targets with similar size range apart, the whole repetitive region can be sequenced by making a shotgun library (e.g., by making a shotgun library from a captured sequence, for example a sequence captured using a MIP probe). The longer the repeat is, the more short reads of repeats will be obtained. Therefore, the target length will contribute twice to the relative number of "repetitive" reads, which will gain better resolution of differentiating targets. In some embodiments, the expectation is that the number of reads from any given repeat will be a direct function of the number of repeats present. However, in some embodiments, a Poisson sampling induced spread may need to be considered and in some embodiments may be sufficiently large to limit the resolution.

Figure 11A:
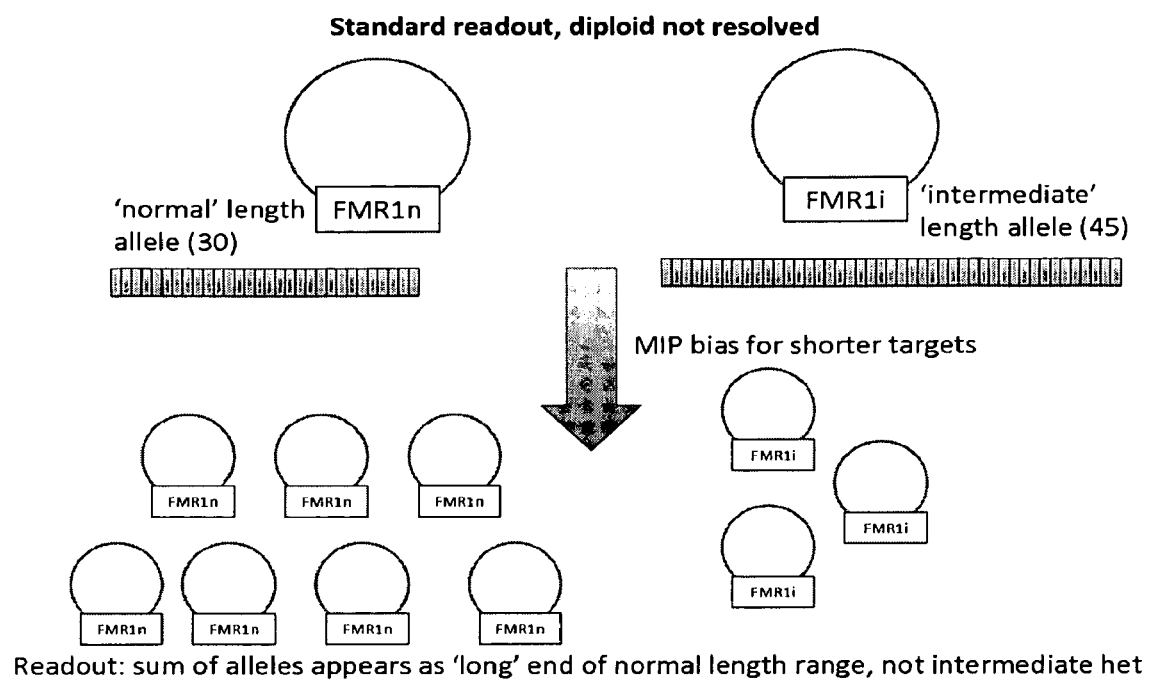
FIG. 11A depicts MIP capture of FMR1 repeat regions from a diploid genome.
Figure 11B:
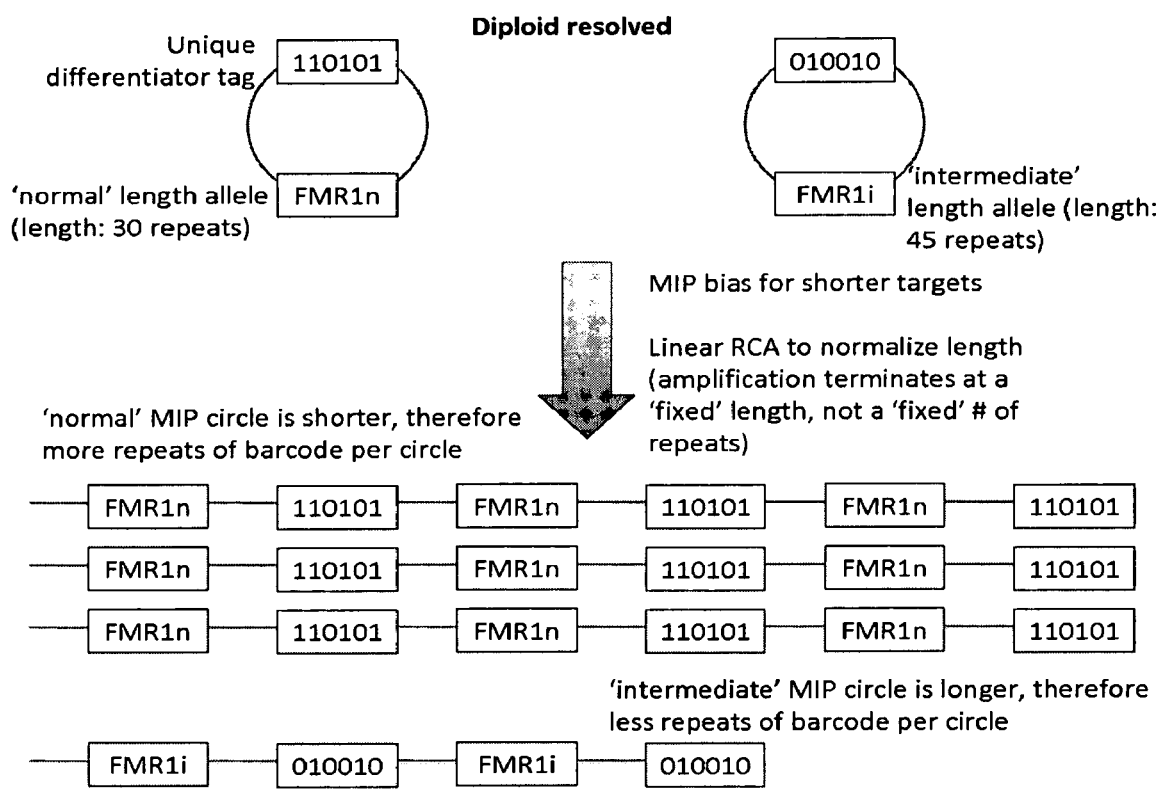
FIG. 11B depicts preparative methods for biallelic resolution of FMR I repeat region lengths in a diploid genome using MIP capture probes and unique differentiator tags.
Figure 11C:
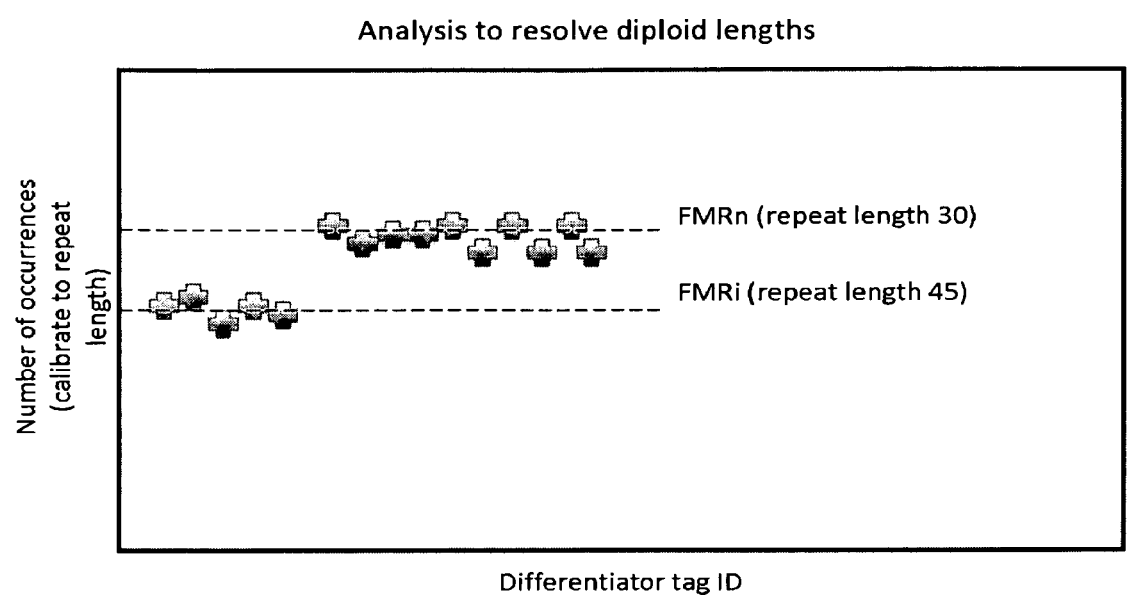
FIG. 11C depicts an analysis of FMR1 repeat region lengths in a diploid genome.

When a precise measurement of the length of both alleles from a diploid sample is desired, further manipulations may be required. This is because the capture efficiency measured will actually be the average efficiency of the two alleles. To effectively achieve separate measurements for each allele, barcodes (e.g., sequence tags) can be used that allow the efficiency of individual capture events (from individual genomic loci) to be followed. FIG. 11A-C shows the approach. For a given locus, MIPs are synthesized to contain one of a large number differentiator tags in their backbone such that the probability of any two MIPs in a reaction having the same differentiator tag sequence is low. MIP capture is performed on the sample; the reaction will be biased for shorter target lengths, and therefore the reaction product will be comprised of more 'short' circles than 'long' circles. Each circle should bear a unique differentiator tag sequence. Then, linear RCA (1RCA) is performed on the circles. In the 1RCA reaction, circles are converted into long, linear concatemers of themselves. The 1RCA reaction for a given circle stops when the concatemer has reached a 'fixed' length (based on the processivity/error rate of the polymerase). Concatemers derived from smaller circles will therefore contain more copies of the differentiator tag, and concatemers derived from larger circles will contain fewer copies of the differentiator tag. The number of each differentiator tag sequence is counted, for example, by next-generation sequencing.

When number of occurrences is plotted against differentiator tag ID, the data will naturally cluster into two groups reflecting the lengths of the two alleles in the diploid sample. The allele lengths can therefore be read directly off this graph, after absolute length calibration using known standards. In some embodiments, a sequencing technique (e.g., a next-generation sequencing technique) is used to sequence part of one or more captured targets (e.g., or amplicons thereof) and the sequences are used to count the number of different barcodes that are present. Accordingly, in some embodiments, aspects of the invention relate to a highly-multiplexed qPCR reaction.

Other non-limiting examples of loci at which insertions or deletions or repeat sequences may be associated with a disease or condition are provided in Tables 3 and 4. It should be appreciated that the presence of an abnormal length at any one or more of these loci may be evaluated according to aspects of the invention. In some embodiments, two or more of these loci or other loci may be evaluated in a single multiplex reaction using different probes designed to hybridize under the same reaction conditions to different target nucleic acid in a biological sample.

TABLE 3

Polyglutamine (PolyQ) Diseases

| Type | Gene | Normal/wildtype | Pathogenic |
|---|---|---|---|
| DRPLA (Dentatorubropallidoluysian atrophy) | ATN1 or DRPLA | 6-35 | 49-88 |
| HD (Huntington's disease) | HTT (Huntingtin) | 10-35 | 35+ |
| SBMA (Spinobulbar muscular atrophy or Kennedy disease) | Androgen receptor on the X chromosome. | 9-36 | 38-62 |
| SCA1 (Spinocerebellar ataxia Type 1) | ATXN1 | 6-35 | 49-88 |
| SCA2 (Spinocerebellar ataxia Type 2) | ATXN2 | 14-32 | 33-77 |
| SCA3 (Spinocerebellar ataxia Type 3 or Machado-Joseph disease) | ATXN3 | 12-40 | 55-86 |
| SCA6 (Spinocerebellar ataxia Type 6) | CACNA1A | 4-18 | 21-30 |
| SCA7 (Spinocerebellar ataxia Type 7) | ATXN7 | 7-17 | 38-120 |
| SCA17 (Spinocerebellar ataxia Type 17) | TBP | 25-42 | 47-63 |

TABLE 4

Non-Polyglutamine Diseases

| Type | Gene | Codon | Normal/wildtype | Pathogenic |
|---|---|---|---|---|
| FRAXA (Fragile X syndrome) | FMR1, on the X-chromosome | CGG | 6-53 | 230+ |
| FXTAS (Fragile X-associated tremor/ataxia syndrome) | FMR1, on the X-chromosome | CGG | 6-53 | 55-200 |
| FRAXE (Fragile XE mental retardation) | AFF2 or FMR2, on the X-chromosome | GCC | 6-35 | 200+ |
| FRDA (Friedreich's ataxia) | FXN or X25, (frataxin) | GAA | 7-34 | 100+ |

TABLE 4-continued

Non-Polyglutamine Diseases

| Type | Gene | Codon | Normal/ wildtype | Pathogenic |
|---|---|---|---|---|
| DM (Myotonic dystrophy) | DMPK | CTG | 5-37 | 50+ |
| SCA8 (Spinocerebellar ataxia Type 8) | OSCA or SCA8 | CTG | 16-37 | 110-250 |
| SCA12 (Spinocerebellar ataxia Type 12) | PPP2R2B or SCA12 | CAG On 5' end | 7-28 | 66-78 |

The following examples illustrate aspects and embodiments of the invention and are not intended to be limiting or restrictive. Many variations of the invention will become apparent to those skilled in the art upon review of this specification. The full scope of the invention should be determined by reference to the claims, along with their full scope of equivalents, and the specification, along with such variations.

4. Increasing Detection Sensitivity:

In some embodiments, aspects of the invention relate to methods for increasing the sensitivity of nucleic acid detection assays.

There are currently many genomic assays that utilize next-generation (e.g., polony-based) sequencing to generate data, including genome resequencing, RNA-seq for gene expression, bisulphite sequencing for methylation, and Immune-seq, among others. In order to make quantitative measurements (including genotype calling), these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. Current assays use one of several alternative nucleic acid preparative techniques (e.g., amplification, for example PCR-based amplification; sequence-specific capture, for example, using immobilized capture probes; or target capture into a circularized probe followed by a sequence analysis step. In order to reduce errors associated with the unpredictability (stochastic nature) of nucleic acid isolation and sequence analysis techniques, current methods involve oversampling a target nucleic acid preparation in order to increase the likelihood that all sequences that are present in the original nucleic acid sample will be represented in the final sequence data. For example, a genomic sequencing library may contain an over- or under-representation of particular sequences from a source nucleic acid sample (e.g., genome preparation) as a result of stochastic variations in the library construction process. Such variations can be particularly problematic when they result in target sequences from a genome being absent or undetectable in a sequencing library. For example, an under-representation of particular allelic sequences (e.g., heterozygotic alleles) from a genome in a sequencing library can result in an apparent homozygous representation in a sequencing library.

In contrast, aspects of the invention relate to basing a nucleic acid sequence analysis on results from two or more different nucleic acid preparatory techniques that have different systematic biases in the types of nucleic acids that they sample rather than simply oversampling the target nucleic acid. According to some embodiments, different techniques have different sequence biases that are systematic and not simply due to stochastic effects during nucleic acid capture or amplification. Accordingly, in some embodiments, the degree of oversampling required to overcome variations in nucleic acid preparation needs to be sufficient to overcome the biases. In some embodiments, the invention provides methods that reduce the need for oversampling by combining nucleic acid and/or sequence results obtained from two or more different nucleic acid preparative techniques that have different biases.

According to the invention, different techniques have different characteristic or systematic biases. For example, one technique may bias a sample analysis towards one particular allele at a genetic locus of interest, whereas a different technique would bias the sample analysis towards a different allele at the same locus. Accordingly, the same sample may be identified as being different depending on the type of technique that is used to prepare nucleic acid for sequence analysis. This effectively represents a sensitivity issue, because each technique has a different relative sensitivities for polymorphic sequences of interest.

According to aspects of the invention, the sensitivity of a nucleic acid analysis can be increased by combining the sequences from different nucleic acid preparative steps and using the combined sequence information for a diagnostic assay (e.g., for a making a call as to whether a subject is homozygous or heterozygous at a genetic locus of interest).

Currently, the ability of DNA sequencing to detect mutations is limited by the ability of the upstream sample isolation (e.g., by amplification, immobilization enrichment, circularization capture, etc.) methods to reliably isolate the locus of interest.

If one wishes to make heterozygote base-calls for a diploid genome (e.g. a human sample presented for molecular diagnostic sequencing), it is important in some embodiments that the isolation method produces near- or perfectly-uniform amounts of the two alleles to be sequenced (at least sufficiently uniform to be "called" unambiguously as a heterozygote or a homozygote for a locus of interest).

Sample preparative methods may fall into three classes: 1) single- or several target amplification (e.g., uniplex PCR, 'multiplex' PCR), 2) multi-target hybridization enrichment (e.g., Agilent SureSelect 'hybrid capture' [Gnirke et al 2009, *Nature methods* 27:182-9], Roche/Nimblegen 'sequence capture' [Hodges et al 2007, *Nature genetics* 39:1522-7], and 3) multi-target circularization selection (e.g. molecular inversion probes or padlock probes, [Porreca et al 2007, *Nature methods* 4:931-6, Turner et al 2009, *Nature methods*

6:315-6], 'selectors' [Dahl et al 2005, *Nucleic acids research* 33:e71]). Each of these methods can result in a pool of isolated product that does not adequately represent the input abundance distribution. For example, the two alleles at a heterozygous position can become skewed far from their input 50:50 ratio to something that results in a missed basecall during downstream sequencing. For example, if the ratio was skewed from 50:50 to 10:90, and the sample was sequenced to 10×average coverage, there is a high probability that one of the two alleles would not be observed once in the ten sequencing reads. This would reduce the sensitivity of the sequencing method by converting a heterozygous position to homozygous (where potentially the 'mutant' allele was the one not observed). In some embodiments, a skewed ratio is a particular issue that decreases the sensitivity of detecting mutations present in a heterogeneous tumor tissue. For example, if only 10% of the cells analyzed in a heterogeneous sample harbored a heterozygous mutation, the mutation would be expected to be present in 5% of sequence reads, not 50%. In this scenario, the need for robust, sensitive detection may be even more acute.

The methods disclosed herein are based, in part, on the discovery that certain classes of isolation methods have different modes of bias. The disclosure provide methods for increasing the sensitivity of the downstream sequencing by using a combination of multiple isolation methods (e.g., one or more from at least two of the classes disclosed herein) for a sample. This is particularly important in molecular diagnostics where high sensitivity is required to minimize the chances of 'missing' a disease-associated mutation. For example, given a nominal false-negative error rate of $1\times10^{-3}$ for sequencing following circularization selection, and a false-negative error rate of $1\times10^{-3}$ for sequencing following hybridization enrichment, one can achieve a final false-negative rate of $1\times10^{-6}$ by performing both techniques on the sample (assuming failures in each method are fully independent). For a recessive disease with carrier frequency of 0.1, caused by a single fully-penetrant mutant allele, the number of missed carrier diagnoses would decrease from 1000 per million patients tested to 1 per million patients tested. Furthermore, if the testing was used in the context of prenatal carrier screening, the number of affected children born as a result of missing the carrier call in one parent would decrease from 25 per million to 25 per billion born.

Additionally, the disclosure provides combinations of preparative methods to effectively increase sequencing coverage in regions containing disease-associated alleles. Since heterozygote error rate is largely tied to both deviations from 50:50 allele representation, and in the case of next-generation DNA sequencing deviations from average abundance (such that less abundant isolated targets are more likely to be undersampled at one or both alleles), selectively increasing coverage in these regions will also selectively increase sensitivity. Furthermore, MIPs that detect presence or absence of specific known disease-associated mutations can be used to increase sensitivity selectively. In some embodiments, these MIPs would have a targeting arm whose 3'-most region is complementary to the expected mutation, and has a fill-in length of 0 or more bp. Thus, the MIP will form only if the mutation is present, and its presence will be detected by sequencing.

Additionally, algorithms disclosed herein may be used to determine base identity with varying levels of stringency depending on whether the given position has any known disease-associated alleles. Stringency can be reduced in such positions by decreasing the minimum number of observed mutant reads necessary to make a consensus base-call. This will effectively increase sensitivity for mutant allele detection at the cost of decreased specificity.

Figure 12:
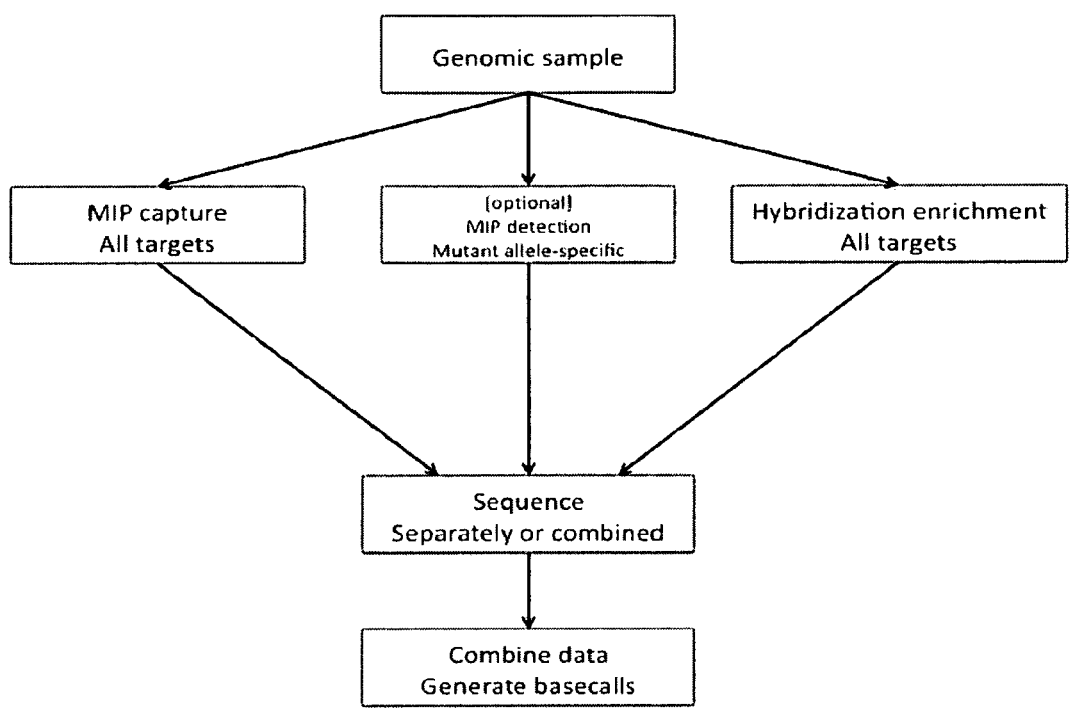
FIG. 12 is a schematic of an embodiment of an algorithm of the invention.

An embodiment of the invention combines MIPs plus hybridization enrichment, plus optionally extra MIPs targeted to specific known, common disease-associated loci, e.g., to detect the presence of a polymorphism in a target nucleic acid. A non-limiting example is illustrated in FIG. 12 that illustrates a schematic using MIPs plus hybridization enrichment, plus optionally extra MIPs targeted to specific known, common disease-associated loci, e.g., to detect the presence of a polymorphism in a target nucleic acid.

Figure 13:
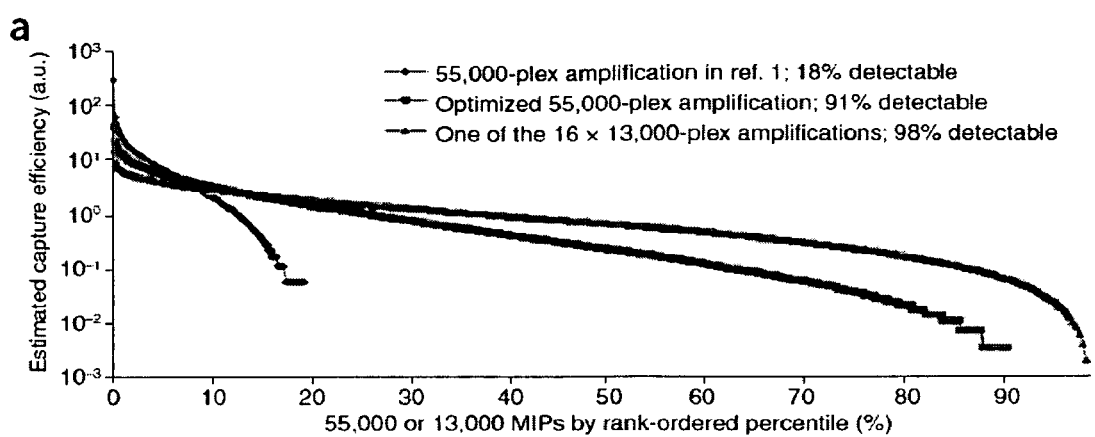
FIG. 13 illustrates a non-limiting example of a graph of per-target abundance with MIP capture; and, FIG. 14 shows a non-limiting a graph of correlation between two MIP capture reactions.
Figure 14:
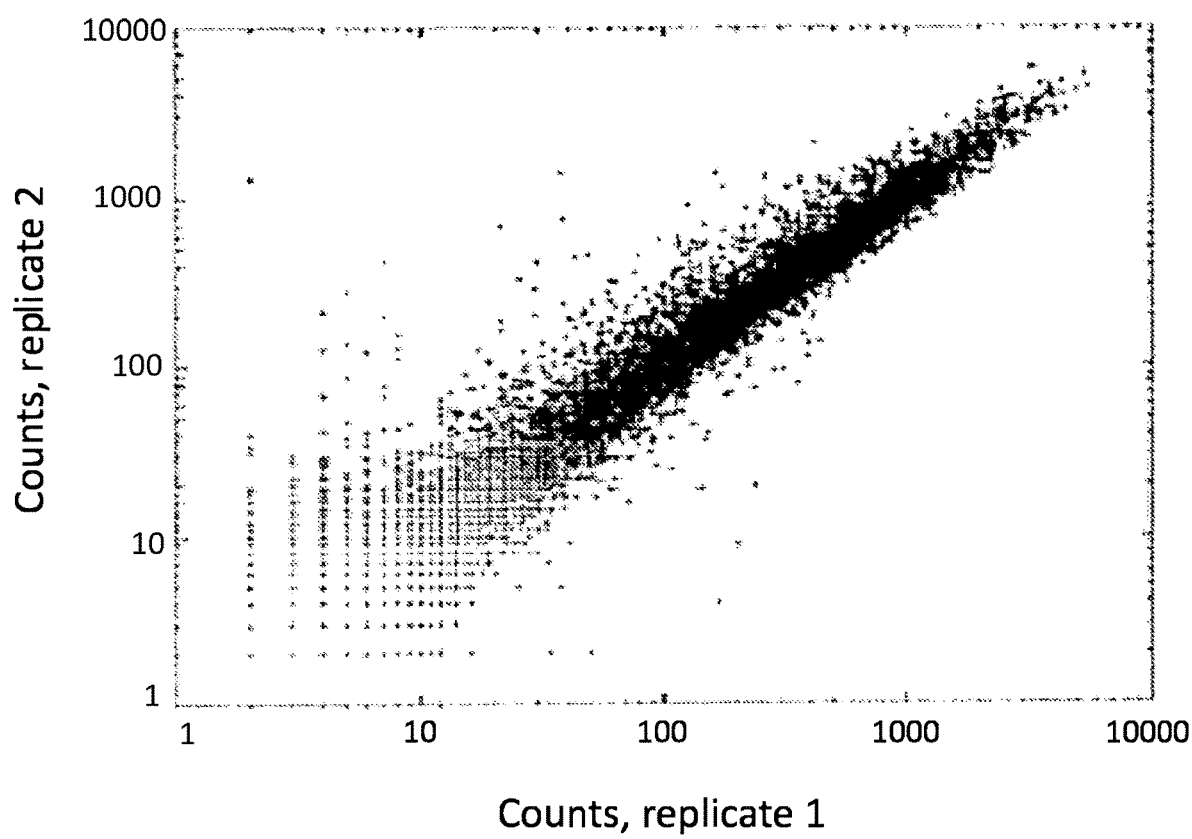

FIGS. 13 and 14 illustrate different capture efficiencies for MIP-based captures. FIG. 13 shows a graph of per-target abundance with MIP capture. In this graph, bias largely drives the heterozygote error rate, since targets which are less abundant here are less likely to be covered in sufficient depth during sequencing to adequately sample both alleles. This is from Turner et al 2009, Nature methods 6:315-6. Hybridization enrichment results in a qualitatively similar abundance distribution, but the abundance of a given target is likely not correlated between the two methods. FIG. 14 shows a graph of correlation between two MIP capture reactions from Ball et al 2009, Nature biotechnology 27:361-8. Each point represents the target abundance in replicate 1 and replicate 2. Pearson correlation r=0.956. This indicates that MIP capture reproducibly biases targets to specific abundances. Hybridization enrichment is similarly correlated from one capture to the next.

According to aspects of the invention, such biases can be detected or overcome by systematically combining different capture and/or analytical techniques in an assay that interrogates a plurality of loci in a plurality of subject samples.

Accordingly, it should be appreciated that in any of the embodiments described herein (e.g., tiling/staggering, tagging, size-detection, sensitivity enhancing algorithms, or any combination thereof), aspects of the invention involve preparing genomic nucleic acid and/or contacting them with one or more different probes (e.g., capture probes, hybridization probes, MIPs, others etc.). In some embodiments, the amount of genomic nucleic acid used per subject ranges from 1 ng to 10 micrograms (e.g., 500 ng to 5 micrograms). However, higher or lower amounts (e.g., less than 1 ng, more than 10 micrograms, 10-50 micrograms, 50-100 micrograms or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured (e.g., on a MIP or other probe or in another form), it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed have a sufficient number of mismatches with any genomic sequence (e.g., at least 5, 10, 15, or more mismatches out of 30 bases) or as having a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments probes or regions of probes or other nucleic acids are described herein as comprising or including certain sequences or sequence characteristics (e.g., length, other properties, etc.). However, it should be appreciated that in some embodiments, any of the probes or regions of probes or other nucleic acids consist of those regions (e.g., arms, central regions, tags, primer sites, etc., or any combination thereof) of consist of those sequences or have sequences with characteristics that consist of one or more characteristics (e.g., length, or other properties, etc.) as described herein in the context of any of the embodiments (e.g., for tiled or staggered probes, tagged probes, length detection, sensitivity enhancing algorithms or any combination thereof).

It should be appreciated that probes, primers, and other nucleic acids designed or used herein may be synthetic, natural, or a combination thereof. Accordingly, as used herein, the term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" may be used interchangeably and refer to oligoribonucleotides as well as oligodeoxyribonucleotides. The terms shall also include polynucleosides (i.e., a polynucleotide minus a phosphate) and any other organic base containing nucleic acid.

The organic bases include adenine, uracil, guanine, thymine, cytosine and inosine. Unless otherwise stated, nucleic acids may be single or double stranded. The nucleic acid may be naturally or non-naturally occurring. Nucleic acids can be obtained from natural sources, or can be synthesized using a nucleic acid synthesizer (i.e., synthetic).

Harvest and isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, or a combination thereof. Non-naturally occurring nucleic acids such as bacterial artificial chromosomes (BACs) and yeast artificial chromosomes (YACs) can also be used.

The invention also contemplates the use of nucleic acid derivatives. As will be described herein, the use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they include nucleic acids having backbone sugars which are covalently attached to low molecular weight organic groups other than a hydroxyl group at the 3' position and other than a phosphate group at the 5' position (e.g., an 2'-0-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc), chemically-reactive groups including carboxyl, NHS, thiol, etc., or any combination thereof.

A nucleic acid may be a peptide nucleic acid (PNA), locked nucleic acid (LNA), DNA, RNA, or co-nucleic acids of the same such as DNA-LNA co-nucleic acids. PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides in some cases.

PNA are synthesized from monomers connected by a peptide bond (Nielsen, P. E. et al. *Peptide Nucleic Acids, Protocols and Applications*, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA. Several types of PNA designs exist, and these include single strand PNA (ssPNA), bisPNA and pseudo-complementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., *Biochemistry* 36:7973 (1997)).

A locked nucleic acid (LNA) is a modified RNA nucleotide. An LNA form hybrids with DNA, which are at least as stable as PNA/DNA hybrids (Braasch, D. A. et al., *Chem & Biol.* 8(1):1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. *Peptide Nucleic Acids, Protocols and Applications*, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

These and other aspects of the invention are illustrated by the following non-limiting examples.

EXAMPLES

The following examples illustrate non-limiting embodiments of the invention.

Example 1: Design a Set of Capture Probes for a Human Target Exon

All targets are captured as a set of partially-overlapping subtargets. For example, in the tiling approach, a 200 bp target exon might be captured as a set of 12 subtargets, each 60 bp in length (FIG. 1). Each subtarget is chosen such that it partially overlaps two or three other targets.

In some embodiments, all probes are composed of three regions: 1) a 20 bp 'targeting arm' comprised of sequence which hybridizes immediately upstream from the sub-target, 2) a 30 bp 'constant region' comprised of sequence used as a pair of amplification priming sites, and 3) a second 20 bp 'targeting arm' comprised of sequence which hybridizes immediately downstream from the sub-target. Targeting arm sequences will be different for each capture probe in a set, while constant region sequence will be the same for all probes in the set, allowing all captured targets to be amplified with a single set of primers. Targeting arm sequences should be designed such that any given pair of 20 bp sequences is unique in the target genome (to prevent spurious capture of undesired sites). Additionally, melting temperatures should be matched for all probes in the set such that hybridization efficiency is uniform for all probes at a constant temperature (e.g., 60 C). Targeting arm sequences should be computationally screened to ensure they do not form strong secondary structure that would impair their ability to basepair with the genomic target.

Hybridize Capture Probes to Human Genomic Sample
Assemble Hybridization Reaction:
1.0 ul capture probe mix (~2.5 μmol)
2.0 ul 10× Ampligase buffer (Epicentre)
6.0 ul 500 ng/ul human genomic DNA (~16.7 fmol)
11 ul dH20
In a thermal cycler, heat reaction to 95 C for 5 min to denature genomic DNA, then cool to 60 C. Allow to incubate at 60 C for 40 hours.

Convert Hybridized Probes into Covalently-Closed Circular Products Containing Subtargets
Prepare Fill-In/Ligation Reaction Mixture:
0.25 ul 2 mM dNTP mix (Invitrogen)
2.5 ul 10×Ampligase buffer (Epicentre)
5.0 ul 5 U/ul Taq Stoffel fragment (Applied Biosystems)
12.5 ul 5 U/ul Ampligase (Epicentre)
4.75 ul dH20
Add 1.0 ul of this mix to the hybridized probe reaction, and incubate at 60 C for 10 hours.

Purify Circularized Probe/Subtarget Products from Un-Reacted Probes and Genomic DNA
Prepare Exonuclease Reaction Mixture:
21 ul fill-in/ligation reaction product
2.0 ul 10×exonuclease I buffer (New England Biolabs)
2.0 ul 20 U/ul exonuclease I (New England Biolabs)
2.0 ul 100 U/ul exonuclease III (New England Biolabs)
Incubate at 37 C for 60 min, then heat-inactivate by incubating at 80 C for 15 min. Immediately cool to 4 C for storage.

Amplify Circular Material by PCR Using Primers Specific to the 'Constant Region' of the Probes
Prepare PCR Mixture:
5.0 ul 10×Accuprime reaction buffer (Invitrogen)
1.5 ul 10 uM CP-2-FA (5'-GCAC-GATCCGACGGTAGTGT-3') (SEQ ID NO:183)
1.5 ul 10 uM CP-2-RA (5'-CCGTAATCGGGAAGCT-GAAG-3') (SEQ ID NO:184)
0.4 ul 25 mM dNTP mix (Invitrogen)
2.0 ul heat-inactivated exonuclease reaction mix
1.5 ul 10×SybrGreen (Invitrogen)
0.4 ul 2.5 U/ul Accuprime Pfx polymerase (Invitrogen)
37.7 ul dH20

Thermal cycle in real-time thermal cycler according to the following protocol, but stop cycling before amplification yield plateaus (generally 8-12 cycles):
1. 95 C for 5 min
2. 95 C for 30 sec
3. 58 C for 60 sec
4. 72 C for 60 sec
5. goto 2, N more times Prepare a Shotgun Next-Generation Sequencing Library for Analysis
  Purify desired amplicon population from non-specific amplification products by gel extraction.
  Concatemerize amplicons into high-molecular weight products suitable for shearing
  Mechanically shear, using either a nebulizer, BioRuptor, Hydroshear, Covaris, or similar instrument. DNA should be sheared into fragments several hundred basepairs in length.
  Ligate adapters required for amplification by the sequencing platform used. If necessary, purify ligated product from unligated product and adapters.

Example 2: Use of Differentiator Tag Sequences to Detect and Correct Bias in a MIP-Capture Reaction of a Set of Exon Targets The first step in performing the detection/correction is to determine how many differentiator tag sequences are necessary for the given sample. In this example, 1000 genomic targets corresponding to 1000 exons were captured. Since the differentiator tag sequence is part of the probe, it will measure/report biases that occur from the earliest protocol steps. Also, being located in the backbone, the differentiator tag sequence can easily be sequenced from a separate priming site, and therefore not impact the total achievable read-length for the target sequence.

MIP probes are synthesized using standard column-based oligonucleotide synthesis by any number of vendors (e.g. IDT), and differentiator tag sequences are introduced as 'degenerate' positions in the backbone. Each degenerate position increases the total number of differentiator tag sequences synthesized by a factor of 4, so a 10 nt degenerate region implies a differentiator tag sequence complexity of ~1e6 species.

Hybridize Capture Probes to Human Genomic Sample
Assemble Hybridization Reaction:
  1.0 ul capture probe mix (~2.5 pmol)
  2.0 ul 10×Ampligase buffer (Epicentre)
  6.0 ul 500 ng/ul human genomic DNA (~16.7 fmol)
  11 ul dH20

In a thermal cycler, heat reaction to 95 C for 5 min to denature genomic DNA, then cool to 60 C. Allow to incubate at 60 C for 40 hours.

Convert Hybridized Probes into Covalently-Closed Circular Products Containing Subtargets
Prepare Fill-In/Ligation Reaction Mixture:
  0.25 ul 2 mM dNTP mix (Invitrogen)
  2.5 ul 10×Ampligase buffer (Epicentre)
  5.0 ul 5 U/ul Taq Stoffel fragment (Applied Biosystems)
  12.5 ul 5 U/ul Ampligase (Epicentre)
  4.75 ul dH20
Add 1.0 ul of this mix to the hybridized probe reaction, and incubate at 60 C for 10 hours.

Purify Circularized Probe/Subtarget Products from Un-Reacted Probes and Genomic DNA
Prepare Exonuclease Reaction Mixture:
  21 ul fill-in/ligation reaction product
  2.0 ul 10×exonuclease I buffer (New England Biolabs)
  2.0 ul 20 U/ul exonuclease I (New England Biolabs)
  2.0 ul 100 U/ul exonuclease III (New England Biolabs)
Incubate at 37 C for 60 min, then heat-inactivate by incubating at 80 C for 15 min. Immediately cool to 4 C for storage.

Amplify Circular Material by PCR Using Primers Specific to the 'Constant Region' of the Probes
Prepare PCR Mixture:
  5.0 ul 10×Accuprime reaction buffer (Invitrogen)
  1.5 ul 10 uM CP-2-FA (5'-GCAC-GATCCGACGGTAGTGT-3') (SEQ ID NO: 183)
  1.5 ul 10 uM CP-2-RA (5'-CCGTAATCGGGAAGCT-GAAG-3') (SEQ ID NO: 184)
  0.4 ul 25 mM dNTP mix (Invitrogen)
  2.0 ul heat-inactivated exonuclease reaction mix
  1.5 ul 10×SybrGreen (Invitrogen)
  0.4 ul 2.5 U/ul Accuprime Pfx polymerase (Invitrogen)
  37.7 ul dH20

Thermal cycle in real-time thermal cycler according to the following protocol, but stop cycling before amplification yield plateaus (generally 8-12 cycles):
6. 95 C for 5 min
7. 95 C for 30 sec
8. 58 C for 60 sec
9. 72 C for 60 sec
10. goto 2, N more times Prepare a Shotgun Next-Generation Sequencing Library for Analysis
  Purify desired amplicon population from non-specific amplification products by gel extraction.
  Concatemerize amplicons into high-molecular weight products suitable for shearing
  Mechanically shear, using either a nebulizer, BioRuptor, Hydroshear,
  Covaris, or similar instrument. DNA should be sheared into fragments several hundred basepairs in length.
  Ligate adapters required for amplification by the sequencing platform used. If necessary, purify ligated product from unligated product and adapters.

Perform Sequencing of Library According to Manufacturer's Directions (e.g. Illumina, ABI, Etc), Reading Both the Target Sequence and the Differentiator Tag Sequence.

Analyze Data by Correcting for any Biases Detected by Quantitation of Differentiator Tag Sequence Abundance Construct a table of target: differentiator tag abundances from the read data, e.g.:

| Target ID | Differentiator Tag sequence ID | Count |
|---|---|---|
| 1 | 3547 | 1 |
| 2 | 4762 | 1 |
| 1 | 9637 | 1 |
| 1 | 1078 | 5 |
| 3 | 4762 | 1 |
| 1 | 2984 | 1 |

All 'count' entries should be '1', since any particular target:differentiator tag mapping will not occur more than once by chance, and therefore will only be observed if bias was present somewhere in the sample preparation process. For any target:differentiator tag combination observed more than once, all such reads are 'collapsed' into a single read before consensus basecalls are determined. This will cancel the effect of bias on consensus basecall accuracy. FIG. 5 depicts a method for making diploid genotype calls in which repeat target:differentiator tag combination are collapsed.

Example 3: Differentiator Tag Sequence Design for MIP Capture Reactions

For a set of targets, the number of differentiator tag sequences necessary to be confident (within some statistical bounds) that a certain differentiator tag sequence will not be observed more than once by chance in combination with a certain target sequence was determined. The total number of unique differentiator tag sequences for a certain differentiator tag sequence length is determined as $4^{(Length\ in\ nucleotides\ of\ the\ differentiator\ tag\ sequence)}$. For a molecular inversion probe capture reaction that uses MIP probes having differentiator tag sequences, the probability of performing the capture reaction and capturing one or more copies of a target sequence having the same differentiator tag sequence is calculated as: $p=1-[N!/(N-M)!]/[N^AM]$, wherein N is the total number of possible unique differentiator tag sequences and M is the number of target sequence copies in the capture reaction. Thus, by varying the differentiator tag sequence length it is possible to perform a MIP capture reaction in which the probability of capturing one or more copies of a target sequence having the same differentiator tag sequence is set at a predetermined probability value.

For example, for a differentiator tag sequence of 15 nucleotides in length, there are 1,073,741,824 possible differentiator tag sequences. A MIP capture reaction in which MIP probes, each having a differentiator tag sequence of 15 nucleotides, are combined with 10000 target sequence copies (e.g., genome equivalents), the probability of capturing one or more copies of a target sequence having the same differentiator tag sequence is 0.05. In this example, the MIP reaction will produce very few (usually 0, but occasionally 1 or more) targets where multiple copies are tagged with the same differentiator tag sequence. FIG. 6 depicts results of a simulation for 100000 capture reactions having 15 nucleotide differentiator tag sequences and 10000 target sequences.

Example 4: Assessment of the Probability for Obtaining Enough Sequencing Reads to Make Accurate Base-Calls at Multiple Independent Loci, as a Function of Sequencing Coverage Monte Carlo simulations were performed to determine sequencing coverage requirements. The simulations assume 10000 genomic copies of a given locus (target) half mom alleles and half dad alleles. The simulations further assume 1% efficiency of capture for the MIP reaction. The simulation samples from a capture mix 100 times without replacement to create a set of 100 capture products. The simulation then samples from the set of 100 capture products with replacement (assuming unbiased amplification) to generate 'reads' from either mom or dad. The number of reads sampled depends on the coverage. The number of independent reads from both mom and dad necessary to make a high-quality base-call (assumed to be 10 or 20 reads) were then determined. The process was repeated 1000 times for each coverage level, and the fraction of times that enough reads from both parents were successfully obtained was determined. This fraction was raised to the power 1000, assuming we have 1000 independent loci that must obtain successful base-calls, plotted (See FIG. 7). Result show that roughly 50× coverage is required to capture each allele >=10× with >0.95 probability.

Example 5: MIP Capture of 'Target' Locus and 'Control' Loci

In some embodiments, to accurately quantify the efficiency of target locus capture, at least three sets of control loci are captured in parallel that have a priori been shown to serve as proxies for various lengths of target locus. For example, if the target locus is expected to have a length between 50 and 1000 bp, then sets of control loci having lengths of 50, 250, and 1000 bp could be captured (e.g. 20 loci per set should provide adequate protection from outliers), and their abundance digitally measured by sequencing. These loci should be chosen such that minimal variation in efficiency between samples and on multiple runs of the same sample is observed (and are therefore 'efficiency invariant'). These will serve as 'reference' points that define the shape of the curve of abundance-vs-length. Determining the length of the target is then simply a matter of 'reading' the length from the appropriate point on the calibration curve.

In some embodiments, the statistical confidence one has in the estimate of target length from this method is driven largely by three factors: 1) reproducibility/variation of the abundance data used to generate the calibration curve; 2) goodness of fit of the regression to the 'control' datapoints; 3) reproducibility of abundance data for the target locus being measured. Statistical bounds on 1) and 2) will be known in advance, having been measured during development of the assay. Additionally, statistical bounds on 3) will be known in general in advance, since assay development should include adequate population sampling and measure of technical reproducibility. Standard statistical methods should be used to combine these three measures into a single P value for any given experimental measure of target abundance.

In some embodiments, given the set of calibration observations, and a linear regression fit to that data, the regression can be used to predict the length value for n observations of the target locus whose length is unknown. First, choose an acceptable range for the confidence interval of the length estimate. For example, in the case of distinguishing "normal" (87-93 bp) from "premutation" (165-600 bp) potential cases of Fragile X, the goal is to measure length to sufficient precision to distinguish 93 bp from 165 bp. The predicted response value, computed when n observations is substituted into the equation for the regressed line, will have arbitrary precision. However, if for example a 95% confidence level is desired, that 95% confidence interval must be sufficiently short that it does not overlap both the "normal" and "premutation" length ranges. Continuing the example, if one calculates a length of 190 from n=400 MIP observations, and based on the regression from calibration data, the 95% confidence interval is 190+/−20 bp, one can conclude the sample represents a "premutation" length with 95% certainty. Conversely, if the calibration data were less robust, error estimates of the regression would be higher, leading to larger confidence intervals on the predicted response value. In some embodiments, if the 95% CI were calculated as 190+/−100 bp from n=400, one could not determine whether the predicted response value corresponds to a "normal" or "premutation" length.

In some embodiments, the confidence interval for a predicted response is calculated as:

The estimate for the response ŷ is identical to the estimate for the mean of the reponse: $\hat{y}=b_0+b_1x^*$. The confidence interval for the predicted value is given by $\hat{y} \pm t^* s\hat{y}$, where ŷ is the fitted value corresponding to x*. The value t* is the upper $(1-C)/2$ critical value for the $t(n-2)$ distribution.

In some embodiments, a technique for analyzing a locus of interest can involve the following steps.

Convert Hybridized Probes into Covalently-Closed Circular Products Containing Subtargets Prepare Fill-In/Ligation Reaction Mixture:
0.25 ul 2 mM dNTP mix (Invitrogen)
2.5 ul 10×Ampligase buffer (Epicentre)
5.0 ul 5 U/ul Taq Stoffel fragment (Applied Biosystems)
12.5 ul 5 U/ul Ampligase (Epicentre)
4.75 ul dH20

Add 1.0 ul of this mix to the hybridized probe reaction, and incubate at 60 C for 10 hours.

Purify Circularized Probe/Subtarget Products from Un-Reacted Probes and 30 Genomic DNA Prepare Exonuclease Reaction Mixture:
21 ul fill-in/ligation reaction product
2.0 ul 10×exonuclease I buffer (New England Biolabs)
2.0 ul 20 U/ul exonuclease I (New England Biolabs)
2.0 ul 100 U/ul exonuclease III (New England Biolabs)

Incubate at 37 C for 60 min, then heat-inactivate by incubating at 80 C for 15 min. Immediately cool to 4 C for storage.

Amplify Circular Material by PCR Using Primers Specific to the 'Constant Region' of the Probes Prepare PCR Mixture:
5.0 ul 10×Accuprime reaction buffer (Invitrogen)
1.5 ul 10 uM CP-2-FA-Ilmn (platform-specific amplification sequence plus 'circle constant region'-specific sequence)
1.5 ul 10 uM CP-2-RA-Ilmn (platform-specific amplification sequence plus 'circle constant region'-specific sequence)
0.4 ul 25 mM dNTP mix (Invitrogen)
2.0 ul heat-inactivated exonuclease reaction mix
1.5 ul 10×SybrGreen (Invitrogen)
0.4 ul 2.5 U/ul Accuprime Pfx polymerase (Invitrogen)
37.7 ul dH20

Thermal cycle in real-time thermal cycler according to the following protocol, but stop cycling before amplification yield plateaus (generally 8-12 cycles):
11. 95 C for 5 min
12. 95 C for 30 sec
13. 58 C for 60 sec
14. 72 C for 60 sec
15. goto 2, N more times Perform Sequencing (e.g., Next-Generation Sequencing) on Sample for Digital Quantitation According to Manufacturer's Instructions (e.g., Illumina, ABI)

Example 6: MIP-capture reaction of a set of exon target nucleic acids

MIP probes are synthesized using standard column-based oligonucleotide synthesis by any number of vendors (e.g. IDT).

Hybridize Capture Probes to Human Genomic Sample
Assemble Hybridization Reaction:
1.0 ul capture probe mix (~2.5 pmol)
2.0 ul 10×Ampligase buffer (Epicentre)
6.0 ul 500 ng/ul human genomic DNA (~16.7 fmol)
11 ul dH20

In a thermal cycler, heat reaction to 95 C for 5 min to denature genomic DNA, then cool to 60 C. Allow to incubate at 60 C for 40 hours.

Convert Hybridized Probes into Covalently-Closed Circular Products Containing Target Nucleic Acids Prepare Fill-In/Ligation Reaction Mixture:
0.25 ul 2 mM dNTP mix (Invitrogen)
2.5 ul 10×Ampligase buffer (Epicentre)
5.0 ul 5 U/ul Taq Stoffel fragment (Applied Biosystems)
12.5 ul 5 U/ul Ampligase (Epicentre)
4.75 ul dH20

Add 1.0 ul of this mix to the hybridized probe reaction, and incubate at 60 C for 10 hours.

Purify, Circularized Probe/Target Nucleic Acid Products from Un-Reacted Probes and Genomic DNA Prepare Exonuclease Reaction Mixture:
21 ul fill-in/ligation reaction product
2.0 ul 10×exonuclease I buffer (New England Biolabs)
2.0 ul 20 U/ul exonuclease I (New England Biolabs)
2.0 ul 100 U/ul exonuclease III (New England Biolabs)

Incubate at 37 C for 60 min, then heat-inactivate by incubating at 80 C for 15 min. Immediately cool to 4 C for storage.

Amplify Circular Material by PCR Using Primers Specific to the 'Constant Region' Of the Probes Prepare PCR Mixture:
5.0 ul 10×Accuprime reaction buffer (Invitrogen)
1.5 ul 10 uM CP-2-FA (5'-GCAC-GATCCGACGGTAGTGT-3') (SEQ ID NO: 183)
1.5 ul 10 uM CP-2-RA (5'-CCGTAATCGGGAAGCT-GAAG-3') (SEQ ID NO: 184)
0.4 ul 25 mM dNTP mix (Invitrogen)
2.0 ul heat-inactivated exonuclease reaction mix
1.5 ul 10×SybrGreen (Invitrogen)
0.4 ul 2.5 U/ul Accuprime Pfx polymerase (Invitrogen)
37.7 ul dH20

Thermal cycle in real-time thermal cycler according to the following protocol, but stop cycling before amplification yield plateaus (generally 8-12 cycles):
16. 95 C for 5 min
17. 95 C for 30 sec
18. 58 C for 60 sec
19. 72 C for 60 sec
20. goto 2, N more times Prepare a Shotgun Next-Generation Sequencing Library for Analysis Purify desired amplicon population from non-specific amplification products by gel extraction.

Concatemerize amplicons into high-molecular weight products suitable for shearing Mechanically shear, using either a nebulizer, BioRuptor, Hydroshear, Covaris, or similar instrument. DNA should be sheared into fragments several hundred basepairs in length.

Ligate adapters required for amplification by the sequencing platform used. If necessary, purify ligated product from unligated product and adapters.

Perform Sequencing of Library According to Manufacturer's Directions (e.g. Illumina, ABI, Etc), Reading the Target Sequence to Determine Abundance of the Target Nucleic Acid.

Example 7: Use of MIPs, Hybridization, and Mutation-Detection MIPs to Genotype a Set of 1000 Targets MIPs, hybridization, and mutation-detection MIPs are used to genotype a set of 1000 targets. The protocol permits detection of any of 50 specific known point mutations First, separate MIP, hybridization, and mutation-detection MIP reactions are performed on a biological sample. A MIP capture reaction is performed essentially as described in Turner et al 2009, Nature methods 6:315-6. A set of MIPs is designed such that each probe in the set flanks one of the 1000 targets. Separately, a hybridization enrichment reaction is performed using the Agilent SureSelect procedure. Prior to selection, the genomic DNA to be enriched is converted into a shotgun sequencing library using Illumina's 'Fragment Library' kit and protocol. Agilent's web interface is used to design a set of probes which will hybridize to the target nucleic acids. Separately, a set of probes are designed (mutation-detection MIPs) which will form MIPs only if mutations (e.g., specific polymorphisms) are present. Each mutation-detection MIP has a 3'-most base identity that is specific for a single known mutation. A reaction with this set of mutation-detection MIPs is performed to selectively detect the presence of any mutant alleles.

Once all three reactions have been performed, the two MIP reactions are combined (e.g., at potentially non-equimolar ratios to further increase sensitivity of mutation detection) into a single tube, and run as one sample on the next-generation DNA sequencing instrument. The hybridization-enriched reaction is run as a separate sample on the next-generation DNA sequencing instrument. Reads from each 'sample' are combined by a software algorithm which forms a consensus diploid genotype at each position in the target set by evaluating the total coverage at each position, the origin of each read in that total coverage, the quality score of each individual read, and the presence (or absence) of any reads derived from mutation-specific MIPs overlapping the region.

It should be appreciated that the preceding examples are non-limiting and aspects of the invention may be implemented as described herein using alternative techniques and/or protocols that are available to one or ordinary skill in the art.

It will be clear that the methods may be practiced other than as particularly described in the foregoing description and examples. Numerous modifications and variations of the present disclosure are possible in light of the above teachings and, therefore, are within the scope of the claims. Preferred features of each aspect of the Disclosure are as for each of the other aspects mutatis mutandis. The documents including patents, patent applications, journal articles, or other disclosures mentioned herein are hereby incorporated by reference in their entirety. In the event of conflict, the disclosure of present application controls, other than in the event of clear error.

What is claimed is:

1. A method for correcting for errors or bias introduced during nucleic acid analysis workflow, the method comprising the steps of:
   obtaining a biological sample comprising a plurality of target nucleic acid molecules from more than one locus of origin;
   introducing a set of differentiator tags, wherein members of said set of differentiator tags are associated with members of said plurality, such that one or more of said loci of origin are associated with more than one differentiator tag;
   amplifying each of the plurality of tagged target nucleic acid molecules to generate amplicons;
   sequencing the amplicons obtained in said amplifying step to obtain sequence reads of each of the amplicons, wherein each of the sequence reads comprises a target nucleic acid molecule sequence and a differentiator tag sequence; and
   correcting for error or bias introduced during said workflow by collapsing target:differentiator tag combinations observed more than once into a single count.

2. The method of claim 1, wherein said correcting step further comprises collapsing all sequence reads comprising a same differentiator tag into a single read before determining a consensus base call for the target nucleic acid molecule sequences.

3. The method of claim 2, further comprising the step of determining the presence of a sequencing or amplification error based upon a number of said differentiator tag sequences.

4. The method of claim 1, wherein said biological sample is selected from the group consisting of blood and biopsy tissue.

5. The method of claim 1, wherein said plurality of target nucleic acid molecules comprises bacterial or viral nucleic acids isolated from said biological sample.

6. The method of claim 1, wherein said plurality of target nucleic acid molecules are circulating tumor nucleic acid molecules.

7. The method of claim 1, further comprising the step of determining the copy number of a genomic region or transcript in a patient from whom the sample is obtained.

8. The method of claim 1, wherein said plurality of target nucleic acid molecules are maternally-circulating fetal or placental nucleic acid molecules.

9. A method for correcting for errors or bias introduced during nucleic acid analysis workflow, the method comprising the steps of:
   obtaining a biological sample comprising a plurality of target nucleic acid molecules from more than one locus of origin;
   introducing a set of unique differentiator tags, wherein members of said set of unique differentiator tags are randomly associated with members of said plurality of target nucleic acid molecules, such that any given tag is uniquely associated with said locus of origin;
   amplifying each of the plurality of tagged target nucleic acid molecules to generate amplicons;
   sequencing the amplicons obtained in said amplifying step to obtain sequence reads of each of the amplicons, wherein each of the sequence reads comprises a target nucleic acid molecule sequence and a differentiator tag sequence; and
   correcting for error or bias introduced during said workflow by recognizing target/differentiator tags having the same sequence as being derived from the same input molecule.

* * * * *